United States Patent
Chen et al.

(10) Patent No.: US 10,710,959 B2
(45) Date of Patent: *Jul. 14, 2020

(54) SULFIDE ALKYL COMPOUNDS FOR HBV TREATMENT

(71) Applicant: NOVIRA THERAPEUTICS, INC., Doylestown, PA (US)

(72) Inventors: Austin Chen, San Marcos, CA (US); Yalda Bravo, San Diego, CA (US); Nicholas Stock, Encinitas, CA (US); Bijan Pedram, San Diego, CA (US); Jason Jacintho, San Diego, CA (US); Ryan C. Clark, San Diego, CA (US)

(73) Assignee: NOVIRA THERAPEUTICS, INC., Doylestown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/235,167

(22) Filed: Dec. 28, 2018

(65) Prior Publication Data
US 2019/0202780 A1 Jul. 4, 2019

Related U.S. Application Data

(63) Continuation of application No. 15/416,222, filed on Jan. 26, 2017, now Pat. No. 10,196,351, which is a
(Continued)

(51) Int. Cl.
| | | |
|---|---|---|
| *C07C 323/53* | (2006.01) | |
| *C07C 323/22* | (2006.01) | |
| *C07C 323/23* | (2006.01) | |
| *C07C 323/62* | (2006.01) | |
| *C07D 213/81* | (2006.01) | |
| *C07D 213/82* | (2006.01) | |
| *C07D 295/084* | (2006.01) | |
| *C07D 295/155* | (2006.01) | |
| *C07D 295/192* | (2006.01) | |
| *C07D 307/10* | (2006.01) | |
| *C07D 307/16* | (2006.01) | |
| *C07D 309/04* | (2006.01) | |
| *C07D 309/08* | (2006.01) | |
| *C07D 487/10* | (2006.01) | |
| *A61K 31/5375* | (2006.01) | |
| *A61K 31/196* | (2006.01) | |
| *A61K 31/351* | (2006.01) | |
| *A61K 31/341* | (2006.01) | |
| *A61K 31/24* | (2006.01) | |

(Continued)

(52) U.S. Cl.
CPC ......... *C07C 323/53* (2013.01); *A61K 31/167* (2013.01); *A61K 31/18* (2013.01); *A61K 31/192* (2013.01); *A61K 31/196* (2013.01); *A61K 31/216* (2013.01); *A61K 31/24* (2013.01); *A61K 31/337* (2013.01); *A61K 31/341* (2013.01); *A61K 31/351* (2013.01); *A61K 31/397* (2013.01); *A61K 31/44* (2013.01); *A61K 31/4412* (2013.01); *A61K 31/4453* (2013.01); *A61K 31/495* (2013.01); *A61K 31/5375* (2013.01); *A61K 45/06* (2013.01); *C07C 323/22* (2013.01); *C07C 323/25* (2013.01); *C07C 323/52* (2013.01); *C07C 323/62* (2013.01); *C07D 213/81* (2013.01); *C07D 213/82* (2013.01); *C07D 295/084* (2013.01); *C07D 295/155* (2013.01); *C07D 295/192* (2013.01); *C07D 305/06* (2013.01); *C07D 307/10* (2013.01); *C07D 307/16* (2013.01); *C07D 307/18* (2013.01); *C07D 309/04* (2013.01); *C07D 309/08* (2013.01); *C07D 487/10* (2013.01); *C07C 2601/02* (2017.05); *C07C 2601/04* (2017.05); *C07C 2601/08* (2017.05); *C07C 2601/14* (2017.05); *C07C 2601/18* (2017.05); *C07C 2602/18* (2017.05); *C07C 2602/20* (2017.05)

(58) Field of Classification Search
CPC ... C07C 323/53; C07C 323/22; C07C 323/23; C07C 323/62; C07D 213/81; C07D 213/82; C07D 295/084; C07D 295/155; C07D 295/192; C07D 307/10; C07D 307/16; C07D 309/04; C07D 309/08; C07D 487/10

See application file for complete search history.

(56) References Cited

U.S. PATENT DOCUMENTS 9,597,332 B2 * 3/2017 Chen ................. A61K 31/5375
10,196,351 B2 * 2/2019 Chen ................. A61K 31/5375

FOREIGN PATENT DOCUMENTS

EP 0 148 725 A1 7/1985
WO 1999/032433 A1 7/1999
(Continued)

OTHER PUBLICATIONS

Database accession No. 1280388-44-4, (Apr. 15, 2011) "Benzamide, N-(4-fluorophenyl)-3-[(2-thienylsulfonyl)amino]-", Registry, Chemical Abstracts Service, Columbus, OH, US.
(Continued)

*Primary Examiner* — Rebecca L Anderson
(74) *Attorney, Agent, or Firm* — Brian C. Trinque; Lathrop GPM LLP

(57) ABSTRACT

The present invention includes a method of inhibiting, suppressing or preventing HBV infection in an individual in need thereof, comprising administering to the individual a therapeutically effective amount of at least one compound of the invention.

8 Claims, 4 Drawing Sheets

Related U.S. Application Data continuation of application No. 14/957,020, filed on Dec. 2, 2015, now Pat. No. 9,597,332.

(60) Provisional application No. 62/086,323, filed on Dec. 2, 2014.

(51) Int. Cl.

| | |
|---|---|
| C07D 305/06 | (2006.01) |
| A61K 31/337 | (2006.01) |
| A61K 31/18 | (2006.01) |
| A61K 31/4453 | (2006.01) |
| A61K 31/495 | (2006.01) |
| A61K 31/397 | (2006.01) |
| A61K 45/06 | (2006.01) |
| A61K 31/167 | (2006.01) |
| A61K 31/192 | (2006.01) |
| A61K 31/216 | (2006.01) |
| A61K 31/44 | (2006.01) |
| A61K 31/4412 | (2006.01) |
| C07C 323/25 | (2006.01) |
| C07C 323/52 | (2006.01) |
| C07D 307/18 | (2006.01) |

(56) References Cited

FOREIGN PATENT DOCUMENTS

| | | |
|---|---|---|
| WO | 2001/019788 A2 | 3/2001 |
| WO | 2013/096744 A1 | 6/2013 |
| WO | 2014/106019 A2 | 7/2014 |

OTHER PUBLICATIONS

Ogata et al. (1986) "Synthesis and Antiviral Activity of Sulfonamidobenzophenone Oximes and Sulfonamidobenzamides" J. Med. Chem. 29:417-423.

International Search Report corresponding to International Patent Application No. PCT/US2015/063417, dated Mar. 2, 2016.

Written Opinion corresponding to International Patent Application No. PCT/US2015/063417, dated Feb. 11, 2016.

Registry No. 896341-85-8, File Registry on STN, Jul. 27, 2006.

* cited by examiner

Intermediates    A      B      C      D      E      F

SULFIDE ALKYL COMPOUNDS FOR HBV TREATMENT

CROSS REFERENCE TO RELATED APPLICATION

This application is a continuation of U.S. application Ser. No. 15/416,222, filed Jan. 26, 2017, which is a continuation of U.S. application Ser. No. 14/957,020, filed on Dec. 2, 2015, now issued as U.S. Pat. No. 9,597,332 which claims priority to U.S. Provisional Patent Application No. 62/086,323, filed Dec. 2, 2014. The contents of this application are herein incorporated by reference in their entirety.

BACKGROUND OF THE INVENTION

Chronic hepatitis B virus (HBV) infection is a significant global health problem, affecting over 5% of the world population (over 350 million people worldwide and 1.25 million individuals in the U.S.).

Despite the availability of a prophylactic HBV vaccine, the burden of chronic HBV infection continues to be a significant unmet worldwide medical problem, due to suboptimal treatment options and sustained rates of new infections in most parts of the developing world. Current treatments do not provide a cure and are limited to only two classes of agents (interferon and nucleoside analogues/inhibitors of the viral polymerase); drug resistance, low efficacy, and tolerability issues limit their impact. The low cure rates of HBV are attributed at least in part to the presence and persistence of covalently closed circular DNA (cccDNA) in the nucleus of infected hepatocytes. However, persistent suppression of HBV DNA slows liver disease progression and helps to prevent hepatocellular carcinoma. Current therapy goals for HBV-infected patients are directed to reducing serum HBV DNA to low or undetectable levels, and to ultimately reducing or preventing the development of cirrhosis and hepatocellular carcinoma.

There is a need in the art for novel therapeutic agents that treat, ameliorate or prevent HBV infection. Administration of these therapeutic agents to an HBV infected patient, either as monotherapy or in combination with other HBV treatments or ancillary treatments, will lead to significantly improved prognosis, diminished progression of the disease, or enhanced seroconversion rates.

SUMMARY OF THE INVENTION

Provided herein are compounds useful for the treatment of HBV infection in a subject in need thereof.

In one aspect, provided herein are compounds of Formula I:

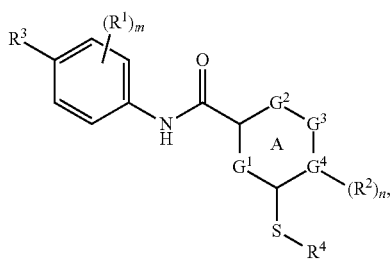

or a pharmaceutically acceptable salt thereof.

In another aspect, provided herein are compounds of Formula II:

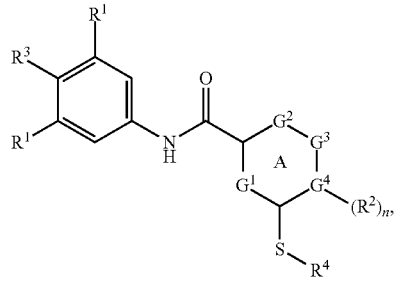

or a pharmaceutically acceptable salt thereof.

In another aspect, provided herein are compounds of Formula III:

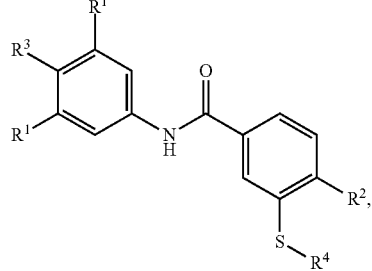

or a pharmaceutically acceptable salt thereof.

Also provided herein are compositions comprising a compound provided herein (also referred to herein as "a compound of the invention"), or a salt, solvate, or N-oxide thereof. In one embodiment, the composition is pharmaceutical and further comprises at least one pharmaceutically acceptable carrier.

In another aspect, provided herein is a method of treating an HBV infection in an individual in need thereof, comprising administering to the individual a therapeutically effective amount of a compound of the invention.

In still another aspect, provided herein is a method of reducing the viral load associated with an HBV infection in an individual in need thereof, comprising administering to the individual a therapeutically effective amount of a compound of the invention.

In yet another aspect, provided herein is a method of reducing reoccurrence of an HBV infection in an individual in need thereof, comprising administering to the individual a therapeutically effective amount of a compound of the invention.

Also provided herein are methods of reducing an adverse physiological impact of an HBV infection in an individual in need thereof, comprising administering to the individual a therapeutically effective amount of a compound of the invention.

In another aspect, provided herein is a method of inducing remission of hepatic injury from an HBV infection in an individual in need thereof, comprising administering to the individual a therapeutically effective amount of a compound of the invention.

In yet another aspect, provided herein is a method of reducing the physiological impact of long-term antiviral therapy for HBV infection in an individual in need thereof, comprising administering to the individual a therapeutically effective amount of a compound of the invention.

In still another aspect, provided herein is a method of prophylactically treating an HBV infection in an individual in need thereof, wherein the individual is afflicted with a latent HBV infection, comprising administering to the individual a therapeutically effective amount of a compound of the invention.

Any of the above methods may further comprise administration to the individual at least one additional therapeutic agent. In an embodiment, the additional therapeutic agent may be selected from, but not limited to, the group consisting of a HBV polymerase inhibitor, immunomodulatory agents, pegylated interferon, viral entry inhibitor, viral maturation inhibitor, capsid assembly modulator, reverse transcriptase inhibitor, a cyclophilin/TNF inhibitor, a TLR-agonist, an HBV vaccine, and agents of distinct or unknown mechanism, and a combination thereof.

In another embodiment, the at least one additional therapeutic agent is selected from the group consisting of an HBV vaccine, HBV polymerase inhibitor, interferon, pegylated interferon, viral entry inhibitor, viral maturation inhibitor, capsid assembly modulator, reverse transcriptase inhibitor, a TLR-agonist, and agents of distinct or unknown mechanism, and a combination thereof.

In still another embodiment, the additional therapeutic agent is selected from the group consisting of a HBV polymerase inhibitor, interferon, viral entry inhibitor, viral maturation inhibitor, capsid assembly modulator, reverse transcriptase inhibitor, a TLR-agonist, and agents of distinct or unknown mechanism, and a combination thereof.

In another embodiment, the pegylated interferon is pegylated interferon alpha (IFN-α), pegylated interferon lambda (IFN-λ), or pegylated interferon gamma (IFN-γ).

In yet another embodiment, the reverse transcriptase inhibitor is at least one of Zidovudine, Didanosine, Zalcitabine, ddA (2',3'-dideoxyadenosine), Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, cidofovir, Efavirenz, Nevirapine, Delavirdine, or Etravirine.

In still another embodiment, the compound and the at least one additional therapeutic agent are co-formulated.

In yet another embodiment, the compound and the at least one additional therapeutic agent are co-administered.

DETAILED DESCRIPTION OF THE INVENTION

Figure 1:
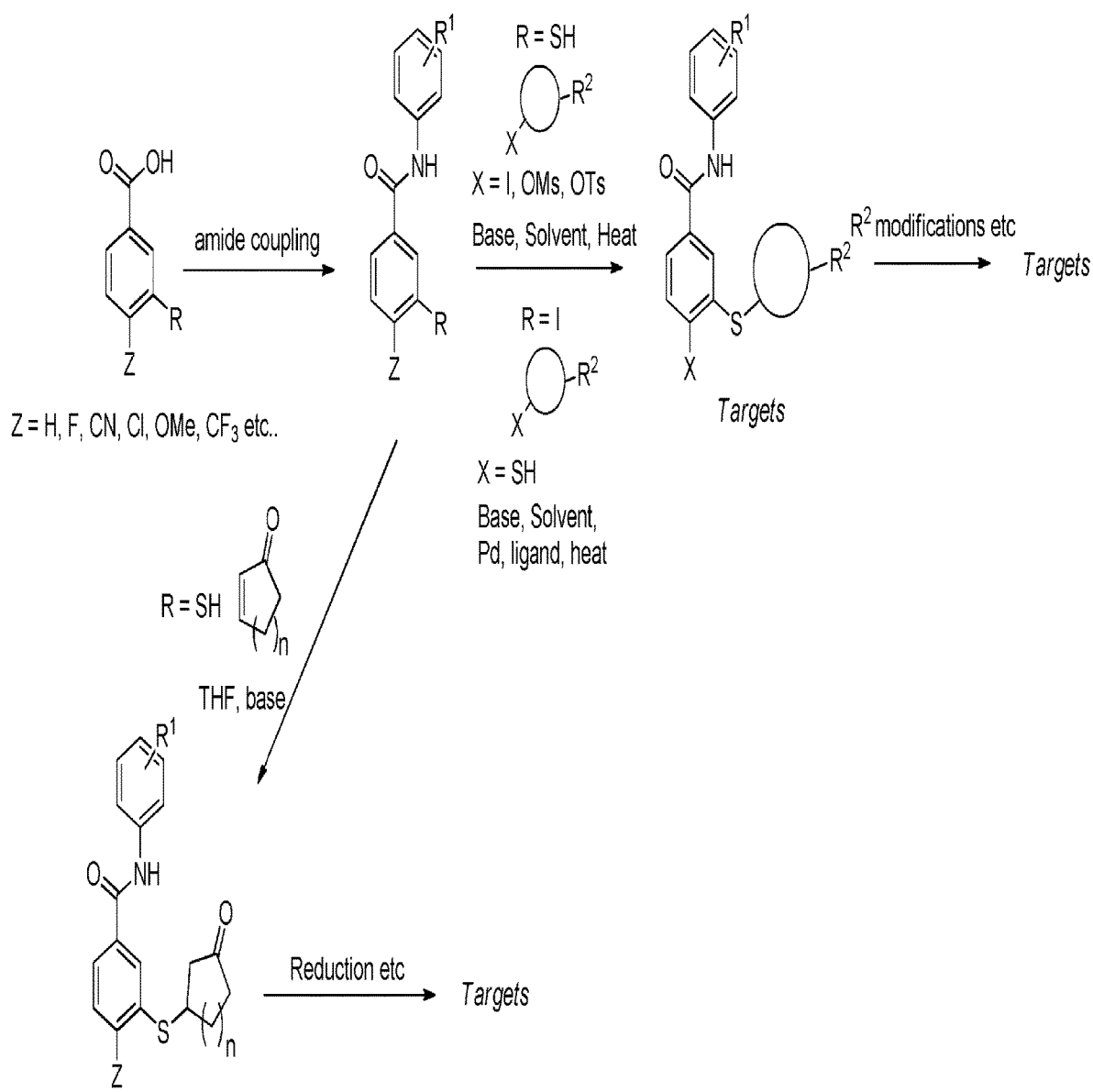
FIG. 1 shows a general scheme used to prepare selected compounds of the invention.

Provided herein are compounds that are useful in the treatment and prevention of HBV in man. In a non-limiting aspect, these compounds modulate or disrupt HBV viral replication to afford defective viral particles with greatly reduced virulence. The compounds of the invention have potent antiviral activity, exhibit favorable metabolic, tissue distribution, safety and pharmaceutical profiles, and are suitable for use in man.

HBV, a causative agent of acute/chronic hepatitis, consists of a partially double-stranded 3.2 kb circular DNA from which four proteins are synthesized: the core, polymerase, surface antigen, and X-gene product.

Four promoters with unique functions have been identified in the HBV genome. The pregenomic/core promoter directs the synthesis of 3.6 kb mRNA which contains all the genetic information encoded by the virus. This RNA serves as a replication intermediate and as a template for the synthesis of core and polymerase. The S promoter and the pre-S promoter direct the synthesis of 2.1 and 2.4 kb RNAs utilized for the generation of pre-S1, pre-S2, and S proteins. X promoter directs the transcription of 0.9 kb RNA specific for the synthesis of X gene product. Liver-specific and differentiation state-specific utilization of these promoters are regulated by the two enhancer elements, i.e., enhancer I (ENI) and enhancer II (ENII). These enhancers along with HNF-1 (hepatocyte nuclear factor-1) binding element are largely responsible for the restricted tropism of HBV to hepatocytes.

The mechanism of HBV replication differs from that of other DNA viruses in that, like retroviruses, the reverse transcription step is involved. Upon infection of the hepatocytes, a partially double-stranded genome is converted to a complete double-stranded circular, supercoiled DNA. Employing this as a template, 3.6 kb RNA, which is called the pregenome, is transcribed. The pregenome is packaged into a nucleocapsid and is reverse-transcribed using polymerase as an initiation primer to generate the minus-strand, single-stranded DNA. The polymerization of the second strand follows until approximately half of the genome is synthesized, resulting in the generation of partially double-stranded circular genome, which is coated and secreted by the infected cells.

In one aspect, the compounds of the invention are useful in HBV treatment by disrupting, accelerating, reducing, delaying or inhibiting normal viral replication, thereby inducing aberrant viral replication and leading to antiviral effects such as disruption of virion assembly or disassembly, virion maturation, or virus egress.

In one embodiment, the compounds of the invention disrupt viral replication when the virion is immature. In another embodiment, the compounds of the invention disrupt viral replication when the virion is mature. In yet another embodiment, the compounds of the invention disrupt viral replication during viral infectivity. In yet another embodiment, the disruption of viral replication attenuates HBV viral infectivity or reduces viral load. In yet another embodiment, disruption, inhibition, delay or reduction of viral replication eradicates the virus from the host organism. In yet another embodiment, eradication of the HBV from a host advantageously obviates the need for chronic long-term therapy or reduces the duration of long-term therapy.

In one embodiment, the compounds described herein are suitable for monotherapy and are effective against natural or native HBV strains and against HBV strains resistant to currently known drugs. In another embodiment, the compounds described herein are suitable for use in combination therapy.

In another embodiment, the compounds of the invention can be used in methods of modulating (e.g., inhibit, disrupt or accelerate) the activity, stability, function, and viral replication properties of HBV cccDNA. In yet another embodiment, the compounds of the invention can be used in methods of diminishing or preventing the formation of HBV cccDNA.

In another embodiment, the compounds of the invention can be used in methods of modulating (e.g., inhibit, disrupt or accelerate) the activity of HBV cccDNA. In yet another embodiment, the compounds of the invention can be used in methods of diminishing or preventing the formation of HBV cccDNA.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "capsid assembly modulator" refers to a compound that disrupts and/or accelerates and/or inhibits and/or hinders and/or delays and or reduces and/or modifies normal capsid assembly (e.g., during maturation) and/or normal capsid disassembly (e.g., during infectivity) and/or perturbs capsid stability, thereby inducing aberrant capsid morphology and function. In one embodiment, a capsid assembly modulator accelerates capsid assembly and/or disassembly, thereby inducing aberrant capsid morphology. In another embodiment, a capsid assembly modulator interacts (e.g. binds at an active site, binds at an allosteric site, modifies and/or hinders folding and the like) with the major capsid assembly protein (CA), thereby disrupting capsid assembly and/or disassembly. In yet another embodiment, a capsid assembly modulator causes a perturbation in structure and/or function of CA (e.g., ability of CA to assemble, disassemble, bind to a substrate, fold into a suitable conformation, or the like), which attenuates viral infectivity and/or is lethal to the virus.

As used herein, the term "literature-described capsid assembly modulator" refers a capsid assembly modulator that is not a compound of the present invention.

As used herein, the term "treatment" or "treating," is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has HBV infection, a symptom of HBV infection or the potential to develop HBV infection, with the purpose to heal, alleviate, relieve, alter, remedy, ameliorate, improve or affect HBV infection, the symptoms of HBV infection or the potential to develop HBV infection. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject or individual is human.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The term "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "alkyl," by itself or as part of another substituent means, unless otherwise stated, a straight or branched chain hydrocarbon having the number of carbon atoms designated (i.e., $C_{1-6}$ means one to six carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$. Preferred heteroalkyl groups have 1-10 carbons.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e., skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

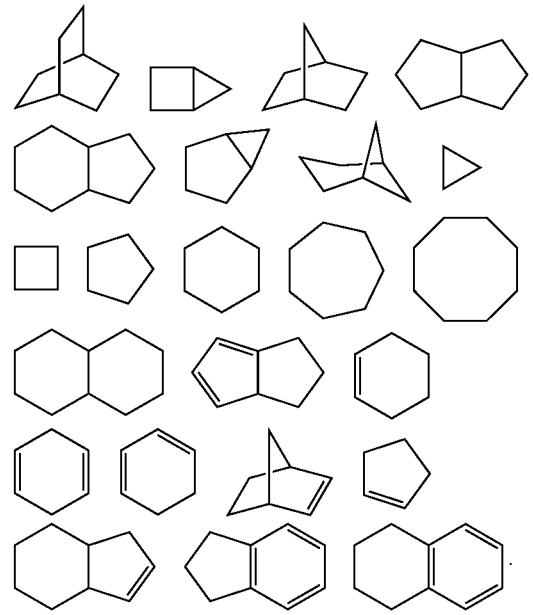

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

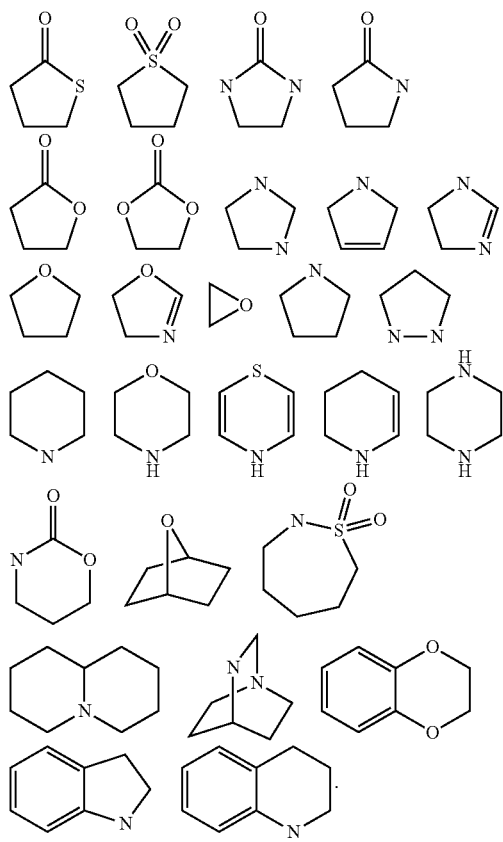

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "bridged $C_{n-n'}$-cycloalkyl" refers to a fused ring system comprising n-n' carbons, a bridged bicyclic ring system comprising n-n' carbons, or a spiro ring system comprising n-n' carbons, wherein n is 6, 7 or 8, and n' is 8, 9, 10, 11, 12, 13 or 14. Examples of n-n' include, but are not limited to, 6-14, 6-10, 6-8, 7-14, 7-10, 7-8, 8-14 or 8-10.

As used herein, the term "heteroaryl" or "heteroaromatic" refers to a heterocycle having aromatic character. A polycyclic heteroaryl may include one or more rings that are partially saturated. Examples include the following moieties:

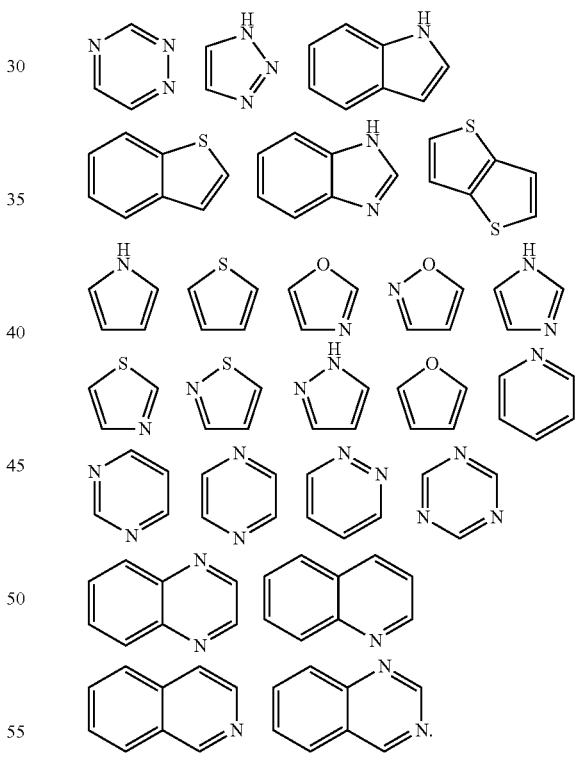

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

Compounds of the Invention

The present invention relates to the discovery of compounds that are useful in the treatment and prevention of HBV infection in man. In one aspect, the compounds of the invention are useful in HBV treatment by disrupting, accelerating, reducing, delaying or inhibiting normal HBV viral replication, thereby inducing aberrant viral replication and leading to antiviral effects such as disruption of virion assembly or disassembly, or virion maturation, or virus egress.

The viral replication disruptors disclosed herein may be used as monotherapy or in novel cross-class combination regimens for treating HBV infection in man. Combination therapy with drugs exhibiting different mechanism of action (MOA) that act at different steps in the virus life cycle may deliver greater efficacy due to additive or synergistic antiviral effects. Clinically evaluated HIV treatment regimens have shown that combination therapy improves the efficacy of viral load reduction, and dramatically reduces emergence of antiviral resistance. Combination therapy for the treatment of Hepatitis C (HCV) virus infection has also resulted in significant improvement in sustained antiviral response and eradication rates. Thus, use of the HBV viral replication inhibitors of the present invention in combination with, for example, NA drugs, is likely to deliver a more profound antiviral effect and greater disease eradication rates than current standards of care.

In one aspect, drug resistance poses a major threat to current therapies for chronic HBV infection, and cross-class combination therapy is a proven strategy for delaying emergence of drug resistance strains. The viral replication disruptors of the present invention can, when administered alone or in combination with other HBV therapy, offer enhanced drug resistant profiles and improved management of chronic HBV.

The compounds useful within the invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound of Formula I:

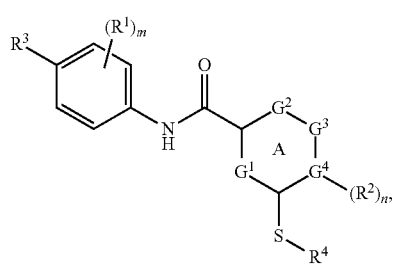

I or a pharmaceutically acceptable salt thereof;

wherein ring A is aryl or heteroaryl;

$G^{1-4}$ are each independently selected from C, CH, N, and NH, wherein at least two of $G^{1-4}$ are independently C or CH;

each $R^1$ is independently selected from H, halo, $C_{1-6}$-alkyl, and $C_{1-6}$-alkoxy;

$R^2$ is selected from H, halo, OH, CN, $C_{1-6}$-alkyl, $C_{1-6}$-alkoxy, halo-($C_{1-6}$-alkyl), di-halo-($C_{1-6}$-alkyl), tri-halo-($C_{1-6}$-alkyl), and (=O);

$R^3$ is halo;

$R^4$ is selected from $C_{1-6}$-alkyl, $C_{1-6}$-heteroalkyl, $C_{3-7}$-cycloalkyl, $C_{3-7}$-heterocycloalkyl, ($C_{1-6}$-alkyl)-($C_{3-7}$-cycloalkyl), ($C_{3-7}$-cycloalkyl)-($C_{1-6}$-alkyl), bridged $C_{7-8}$-cycloalkyl, ($C_{1-6}$-alkyl)-C(O)O—($C_{1-6}$-alkyl), and ($C_{1-6}$-alkyl)-($C_{3-7}$-heterocycloalkyl), all of which may be optionally independently substituted with one or two groups selected from (=O), OH, $C_{1-6}$-alkyl, $C_{3-7}$-cycloalkyl, halo-($C_{1-6}$-alkyl), di-halo-($C_{1-6}$-alkyl), tri-halo-($C_{1-6}$-alkyl), C(O)OH, ($C_{1-6}$-alkyl)-C(O)OH, aryl, and halo;

or $R^4$ is selected from ($C_{3-7}$-cycloalkyl)-C(O)$R^5$ and (bridged $C_{7-8}$-cycloalkyl)-C(O)$R^5$, wherein $R^5$ is selected from N(H)$C_{1-6}$-alkyl, N($C_{1-6}$-alkyl)$_2$, NS(O)$_2$—($C_{1-6}$-alkyl), and $C_{3-7}$-heterocycloalkyl;

m is 1 or 2; and n is 0 or 1.

In one embodiment, ring A is

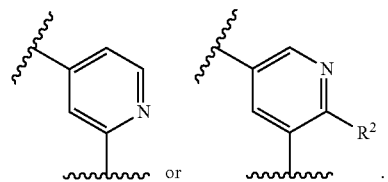

In another embodiment, ring A is

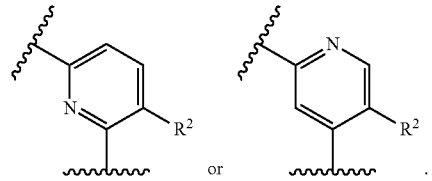

In still another embodiment, $R^2$ is selected from H, halo, OH, CN, and $C_{1-6}$-alkyl.

In yet another embodiment, $R^4$ is selected from $C_{1-6}$-alkyl, $C_{1-6}$-heteroalkyl, $C_{3-7}$-cycloalkyl, $C_{3-7}$-heterocycloalkyl, all of which may be optionally independently substituted with one or two groups selected from OH and $C_{1-6}$-alkyl.

In another aspect, the compound of the invention is a compound of Formula II:

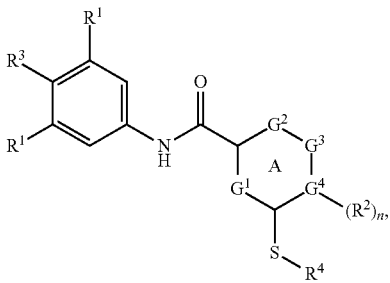

or a pharmaceutically acceptable salt thereof;
wherein
ring A is heteroaryl;
three of $G^{1-4}$ are selected from C and CH, and one of $G^{1-4}$ is selected from N and NH;
each $R^1$ is independently selected from H and halo;
$R^2$ is selected from H and (=O);
$R^3$ is halo;
$R^4$ is $C_{3-7}$-cycloalkyl optionally substituted with OH; and
n is 0 or 1.
In one embodiment, ring A is

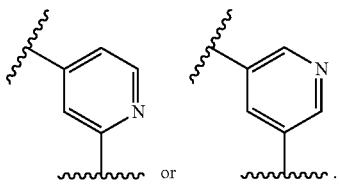 [SMILES: *c1ccnc(*)c1 ; *c1cncc(*)c1]

In another embodiment ring A is

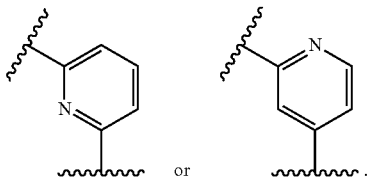 [SMILES: *c1cccc(*)n1 ; *c1ccnc(*)c1]

In still another aspect, the compound of the invention is a compound of Formula III:

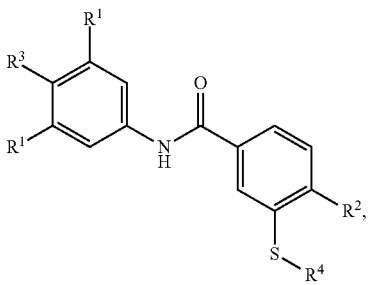

or a pharmaceutically acceptable salt thereof;
wherein
each $R^1$ is independently selected from H, halo and $C_{1-6}$-alkyl;

$R^2$ is selected from H, halo, OH, CN, $C_{1-6}$-alkyl, $C_{1-6}$-alkoxy, halo-($C_{1-6}$-alkyl), di-halo-($C_{1-6}$-alkyl), and tri-halo-($C_{1-6}$-alkyl);
$R^3$ is halo; and
$R^4$ is selected from $C_{1-6}$-alkyl, $C_{1-6}$-heteroalkyl, $C_{3-7}$-cycloalkyl, $C_{3-7}$-heterocycloalkyl, ($C_{1-6}$-alkyl)-($C_{3-7}$-cycloalkyl), ($C_{3-7}$-cycloalkyl)-($C_{1-6}$-alkyl), bridged $C_{7-8}$-cycloalkyl, ($C_{1-6}$-alkyl)-C(O)O—($C_{1-6}$-alkyl), and ($C_{1-6}$-alkyl)-($C_{3-7}$-heterocycloalkyl), all of which may be optionally independently substituted with one or two groups selected from (=O), OH, $C_{1-6}$-alkyl, $C_{3-7}$-cycloalkyl, halo-($C_{1-6}$-alkyl), di-halo-($C_{1-6}$-alkyl), tri-halo-($C_{1-6}$-alkyl), C(O)OH, phenyl, and halo;
or $R^4$ is selected from ($C_{3-7}$-cycloalkyl)-C(O)$R^5$ and (bridged $C_{7-8}$-cycloalkyl)-C(O)$R^5$, wherein $R^5$ is selected from N(CH$_3$)$_2$, NS(O)$_2$CH$_3$, and piperidinyl.

In one embodiment, $R^2$ is selected from H, halo, OH, CN, $C_{1-6}$-alkyl, $C_{1-6}$-alkoxy, and CF$_3$.

In another embodiment, $R^4$ is selected from $C_{1-6}$-alkyl, $C_{1-6}$-heteroalkyl, $C_{3-7}$-cycloalkyl, $C_{3-7}$-heterocycloalkyl, ($C_{1-6}$-alkyl)-($C_{3-7}$-cycloalkyl), and ($C_{1-6}$-alkyl)-($C_{3-7}$-heterocycloalkyl), all of which may be optionally independently substituted with one or two groups selected from (=O), OH, $C_{1-6}$-alkyl, C(O)OH, and halo.

In another embodiment, each $R^1$ is independently selected from halo and $C_{1-6}$-alkyl.

In another embodiment, each $R^1$ is independently selected from H and halo.

In another embodiment, each $R^1$ is independently selected from halo.

In another embodiment, $R^2$ is selected from H, halo, CN, $C_{1-6}$-alkyl, $C_{1-6}$-alkoxy, and tri-halo-($C_{1-6}$-alkyl).

In another embodiment, $R^2$ is selected from H, halo, CN, CH$_3$, OCH$_3$, and CF$_3$.

In another embodiment, $R^2$ is halo.
In another embodiment, $R^2$ is F.
In another embodiment, $R^3$ is F.

In another embodiment, $R^4$ is selected from $C_{3-7}$-cycloalkyl, $C_{3-7}$-heterocycloalkyl, ($C_{1-6}$-alkyl)-($C_{3-7}$-cycloalkyl), and ($C_{1-6}$-alkyl)-($C_{3-7}$-heterocycloalkyl), all of which may be optionally independently substituted with one or two groups selected from (=O), OH, $C_{1-6}$-alkyl, C(O)OH, phenyl, and halo.

In another embodiment, $R^4$ is $C_{3-7}$-cycloalkyl or ($C_{1-6}$-alkyl)-($C_{3-7}$-cycloalkyl), each of which is substituted with (=O), OH, $C_{1-6}$-alkyl, C(O)OH, or halo.

In another embodiment, $R^4$ is $C_{3-7}$-cycloalkyl or ($C_{1-6}$-alkyl)-($C_{3-7}$-cycloalkyl), each of which is substituted C(O)OH.

In yet another aspect, the compound of the invention is a compound of Formula IIIa:

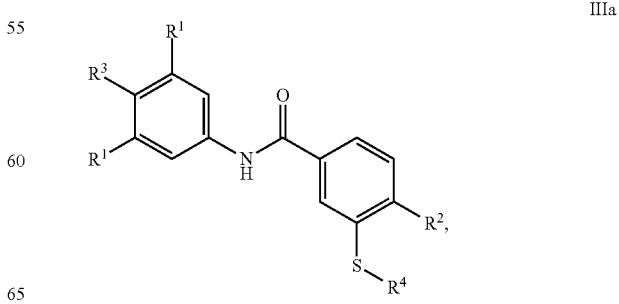

or a pharmaceutically acceptable salt thereof;
wherein
each $R^1$ is independently selected from H, halo and $C_{1-6}$-alkyl;

$R^2$ is selected from H, halo, OH, CN, $C_{1-6}$-alkyl, $C_{1-6}$-alkoxy, halo-($C_{1-6}$-alkyl), di-halo-($C_{1-6}$-alkyl), and tri-halo-($C_{1-6}$-alkyl);

$R^3$ is halo; and $R^4$ is selected from $C_{1-6}$-alkyl, $C_{1-6}$-heteroalkyl, $C_{3-7}$-cycloalkyl, $C_{3-7}$-heterocycloalkyl, ($C_{1-6}$-alkyl)-($C_{3-7}$-cycloalkyl), ($C_{3-7}$-cycloalkyl)-($C_{1-6}$-alkyl), bridged $C_{7-8}$-cycloalkyl, ($C_{1-6}$-alkyl)-C(O)O—($C_{1-6}$-alkyl), and ($C_{1-6}$-alkyl)-($C_{3-7}$-heterocycloalkyl), all of which may be optionally independently substituted with one or two groups selected from (=O), OH, $C_{1-6}$-alkyl, $C_{3-7}$-cycloalkyl, halo-($C_{1-6}$-alkyl), di-halo-($C_{1-6}$-alkyl), tri-halo-($C_{1-6}$-alkyl), C(O)OH, phenyl, and halo;

or $R^4$ is selected from ($C_{3-7}$-cycloalkyl)-C(O)$R^5$ and (bridged $C_{7-8}$-cycloalkyl)-C(O)$R^5$, wherein $R^5$ is selected from N(CH$_3$)$_2$, NS(O)$_2$CH$_3$, and $C_{3-7}$-heterocycloalkyl.

In one embodiment of Formula IIIa, $R^2$ is selected from H, halo, OH, CN, $C_{1-6}$-alkyl, $C_{1-6}$-alkoxy, and CF$_3$.

In another embodiment, $R^4$ is selected from $C_{1-6}$-alkyl, $C_{1-6}$-heteroalkyl, $C_{3-7}$-cycloalkyl, $C_{3-7}$-heterocycloalkyl, ($C_{1-6}$-alkyl)-($C_{3-7}$-cycloalkyl), and ($C_{1-6}$-alkyl)-($C_{3-7}$-heterocycloalkyl), all of which may be optionally independently substituted with one or two groups selected from (=O), OH, $C_{1-6}$-alkyl, C(O)OH, and halo.

In yet another embodiment, each $R^1$ is independently selected from halo and $C_{1-6}$-alkyl.

In still another embodiment, each $R^1$ is independently selected from H and halo.

In another embodiment, each $R^1$ is independently selected from halo.

In yet another embodiment of Formula IIIa, $R^2$ is selected from H, halo, CN, $C_{1-6}$-alkyl, $C_{1-6}$-alkoxy, and tri-halo-($C_{1-6}$-alkyl).

In still another embodiment, $R^2$ is selected from H, halo, CN, CH$_3$, OCH$_3$, and CF$_3$.

In another embodiment, $R^2$ is halo.

In yet another embodiment, $R^2$ is F.

In still another embodiment, $R^3$ is F.

In another embodiment of Formula IIIa, $R^4$ is selected from $C_{3-7}$-cycloalkyl, $C_{3-7}$-heterocycloalkyl, ($C_{1-6}$-alkyl)-($C_{3-7}$-cycloalkyl), and ($C_{1-6}$-alkyl)-($C_{3-7}$-heterocycloalkyl), all of which may be optionally independently substituted with one or two groups selected from (=O), OH, $C_{1-6}$-alkyl, C(O)OH, phenyl, and halo;

or $R^4$ is selected from ($C_{3-7}$-cycloalkyl)-C(O)$R^5$, wherein $R^5$ is selected from N(CH$_3$)$_2$, NS(O)$_2$CH$_3$, and $C_{3-7}$-heterocycloalkyl.

In yet another embodiment, $R^4$ is selected from $C_{3-7}$-cycloalkyl, $C_{3-7}$-heterocycloalkyl, ($C_{1-6}$-alkyl)-($C_{3-7}$-cycloalkyl), and ($C_{1-6}$-alkyl)-($C_{3-7}$-heterocycloalkyl), all of which may be optionally independently substituted with one or two groups selected from (=O), OH, $C_{1-6}$-alkyl, C(O)OH, phenyl, and halo;

or $R^4$ is selected from ($C_{3-7}$-cycloalkyl)-C(O)$R^5$, wherein $R^5$ is selected from N(CH$_3$)$_2$, NS(O)$_2$CH$_3$, and $C_{3-7}$-heterocycloalkyl.

In still another embodiment, $R^4$ is $C_{3-7}$-cycloalkyl or ($C_{1-6}$-alkyl)-($C_{3-7}$-cycloalkyl), each of which is substituted with (=O), OH, $C_{1-6}$-alkyl, C(O)OH, or halo;

or $R^4$ is selected from ($C_{3-7}$-cycloalkyl)-C(O)$R^5$, wherein $R^5$ is N(CH$_3$)$_2$, or $C_{3-7}$-heterocycloalkyl.

In another embodiment, $R^4$ is $C_{3-7}$-cycloalkyl or ($C_{1-6}$-alkyl)-($C_{3-7}$-cycloalkyl), each of which is substituted C(O)OH;

or $R^4$ is selected from ($C_{3-7}$-cycloalkyl)-C(O)$R^5$, wherein $R^5$ is $C_{3-7}$-heterocycloalkyl.

In yet another embodiment, $R^4$ is selected from ($C_{3-7}$-cycloalkyl)-C(O)$R^5$, wherein $R^5$ is $C_{3-7}$-heterocycloalkyl.

In another embodiment of Formula IIIa, or a pharmaceutically acceptable salt thereof, each $R^1$ is halo; $R^2$ is halo; $R^3$ is halo; and $R^4$ is $C_{3-7}$-cycloalkyl or ($C_{1-6}$-alkyl)-($C_{3-7}$-cycloalkyl), each of which may be independently substituted with C(O)OH; or $R^4$ is ($C_{3-7}$-cycloalkyl)-C(O)$R^5$, and $R^5$ is $C_{3-7}$-heterocycloalkyl.

In another embodiment, $R^4$ is $C_{3-7}$-cycloalkyl or ($C_{1-6}$-alkyl)-($C_{3-7}$-cycloalkyl), each of which may be independently substituted with C(O)OH; or $R^4$ is ($C_{3-7}$-cycloalkyl)-C(O)$R^5$, and $R^5$ is morpholinyl.

In another embodiment of Formula IIIa, or a pharmaceutically acceptable salt thereof, the compound is selected from the group consisting of:

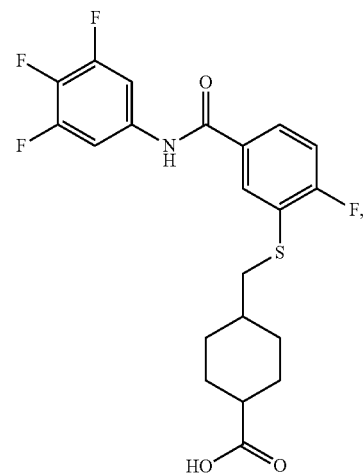

(110)

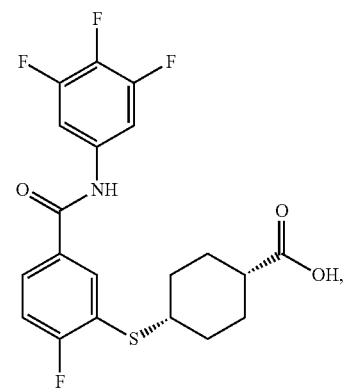

(112A)

-continued (112B)

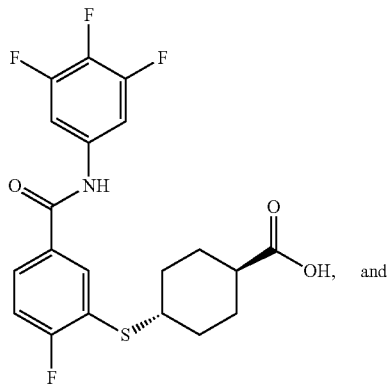

and (116)

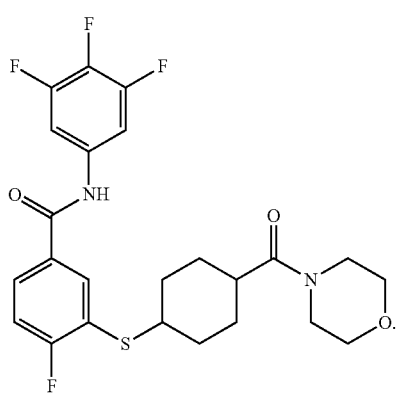

It will be appreciated that the description of the present invention herein should be construed in congruity with the laws and principals of chemical bonding. In some instances it may be necessary to remove a hydrogen atom in order to accommodate a substitutent at any given location.

Preferred embodiments of Formula I, Formula II, Formula III, and Formula IIIa, including pharmaceutically acceptable salts thereof, are shown below in Table 1 and are also considered to be "compounds of the invention." Some compounds of Table 1 do not include hydrogens on hydroxyl groups; it is understood that "—O" indicates a hydroxyl substituent at these positions.

TABLE 1

1

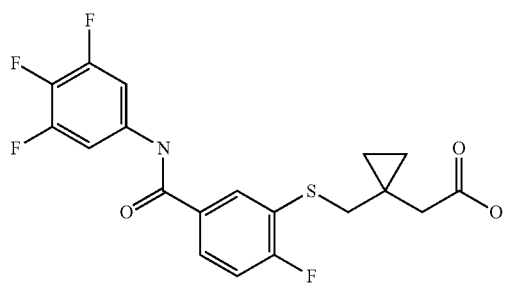 [SMILES: O=C(O)CC1(CSc2cc(C(=O)Nc3cc(F)c(F)c(F)c3)ccc2F)CC1]

TABLE 1-continued

2

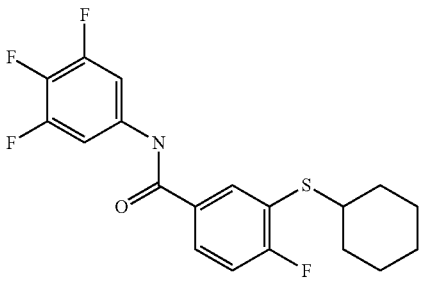 [SMILES: O=C(Nc1cc(F)c(F)c(F)c1)c1ccc(F)c(SC2CCCCC2)c1]

3

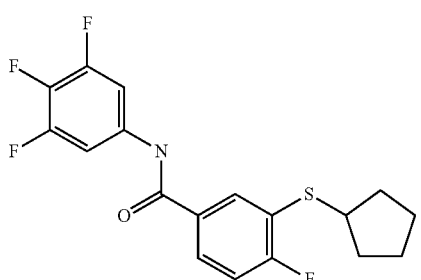

4

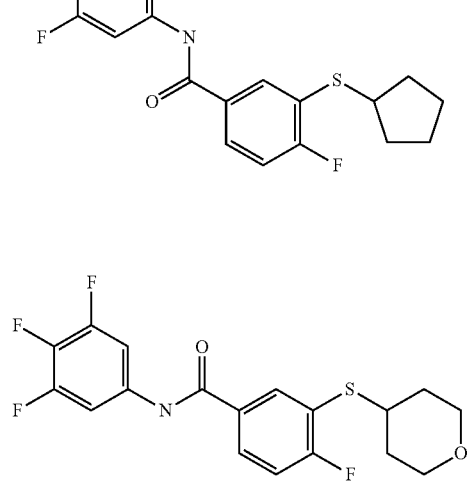

5

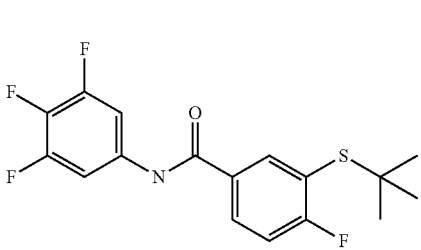 [SMILES: CC(C)(C)Sc1cc(C(=O)Nc2cc(F)c(F)c(F)c2)ccc1F]

6

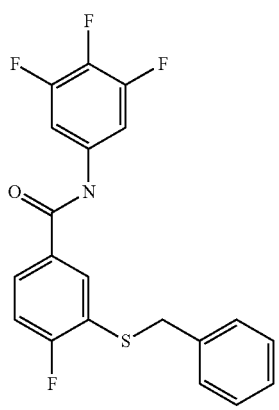 [SMILES: O=C(Nc1cc(F)c(F)c(F)c1)c1ccc(F)c(SCc2ccccc2)c1]

TABLE 1-continued
| | |
|---|---|
| 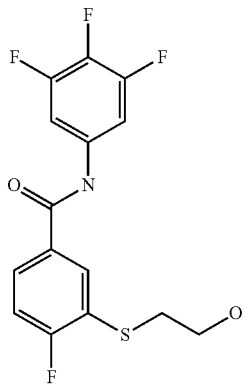 [SMILES: O=C(Nc1cc(F)c(F)c(F)c1)c1ccc(F)c(SCCO)c1] 7 | 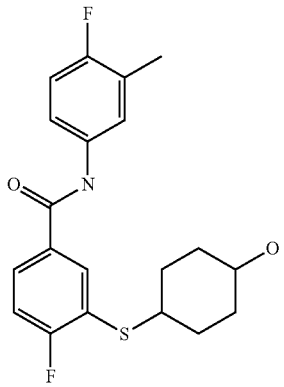 11 |
| 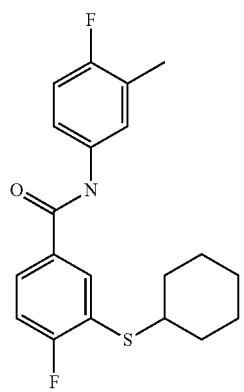 [SMILES: Cc1cc(NC(=O)c2ccc(F)c(SC3CCCCC3)c2)ccc1F] 8 | 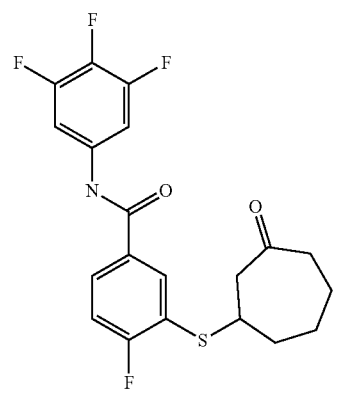 12 |
| 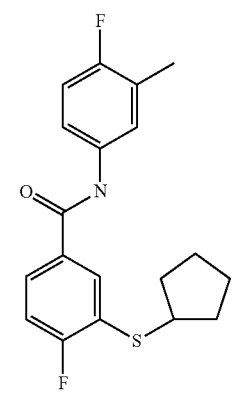 [SMILES: Cc1cc(NC(=O)c2ccc(F)c(SC3CCCC3)c2)ccc1F] 9 | 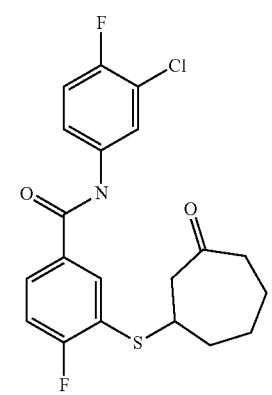 [SMILES: O=C1CCCCC(Sc2cc(C(=O)Nc3ccc(F)c(Cl)c3)ccc2F)C1] 13 |
| 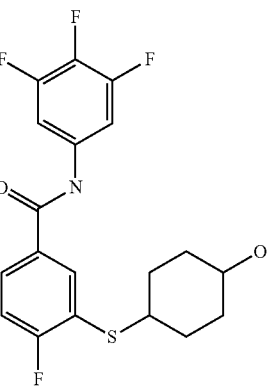 10 | 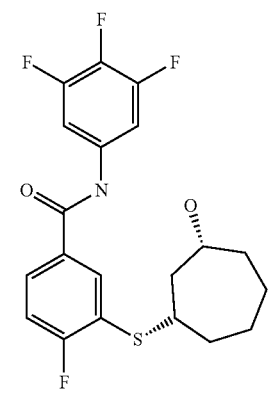 14A |

TABLE 1-continued
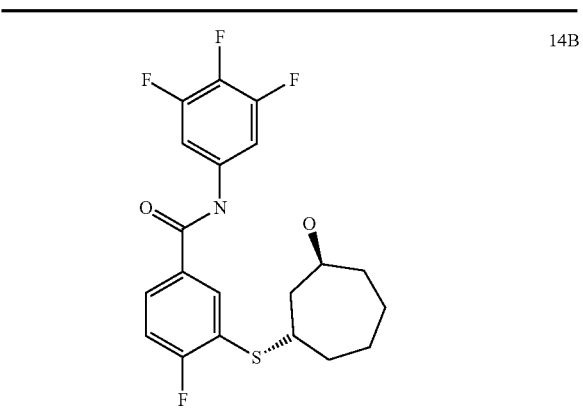
14B
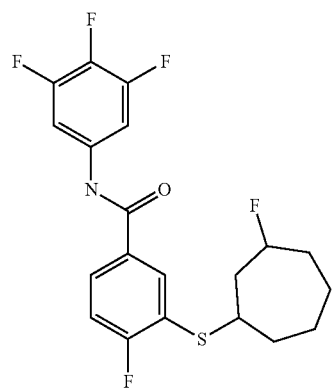 [SMILES: O=C(Nc1cc(F)c(F)c(F)c1)c1ccc(F)c(SC2CCCCC(F)C2)c1]
15
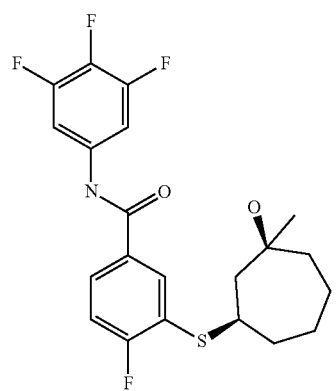 [SMILES: C[C@]1(O)CCCC[C@@H](Sc2cc(C(=O)Nc3cc(F)c(F)c(F)c3)ccc2F)C1]
16
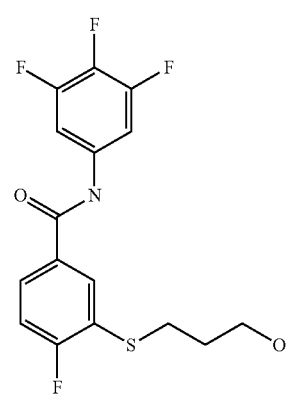 [SMILES: O=C(Nc1cc(F)c(F)c(F)c1)c1ccc(F)c(SCCCO)c1]
17
TABLE 1-continued
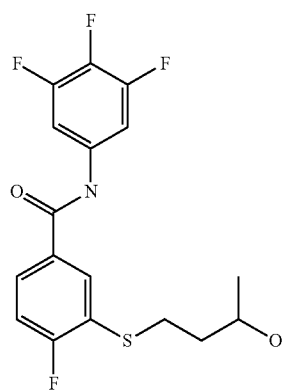 [SMILES: CC(O)CCSc1cc(C(=O)Nc2cc(F)c(F)c(F)c2)ccc1F]
18
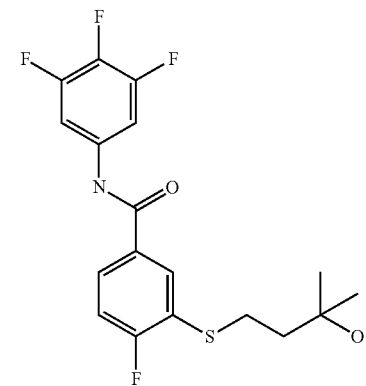 [SMILES: CC(C)(O)CCSc1cc(C(=O)Nc2cc(F)c(F)c(F)c2)ccc1F]
19
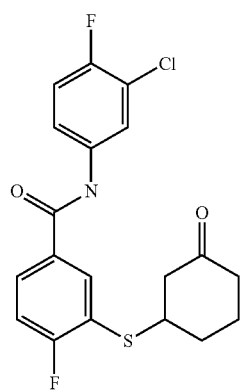 [SMILES: O=C1CCCC(Sc2cc(C(=O)Nc3ccc(F)c(Cl)c3)ccc2F)C1]
20
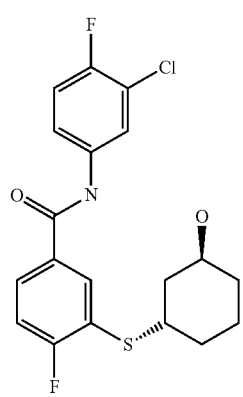
21

TABLE 1-continued
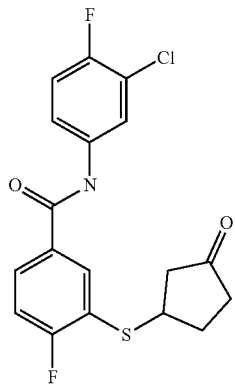 [SMILES: O=C1CCC(Sc2cc(C(=O)Nc3ccc(F)c(Cl)c3)ccc2F)C1]
22
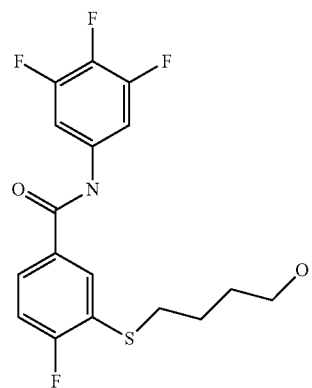 [SMILES: O=C(Nc1cc(F)c(F)c(F)c1)c1ccc(F)c(SCCCCO)c1]
23
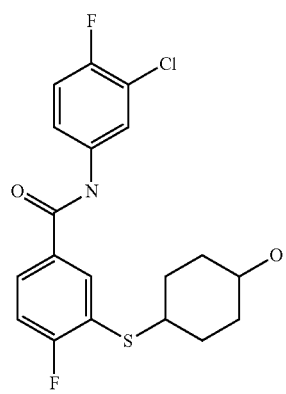 [SMILES: O=C(Nc1ccc(F)c(Cl)c1)c1ccc(F)c(SC2CCC(O)CC2)c1]
24
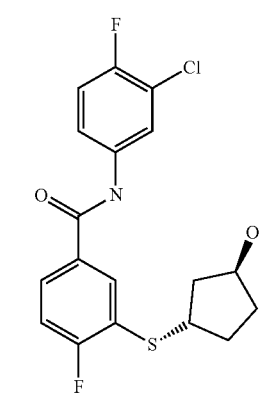
25
TABLE 1-continued
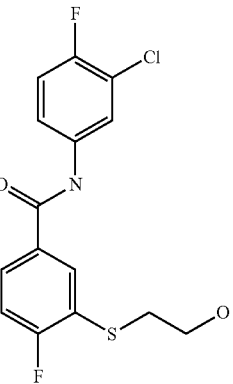
26
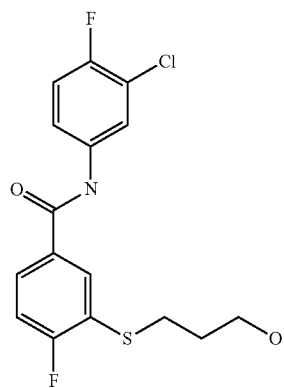 [SMILES: O=C(Nc1ccc(F)c(Cl)c1)c1ccc(F)c(SCCCO)c1]
27
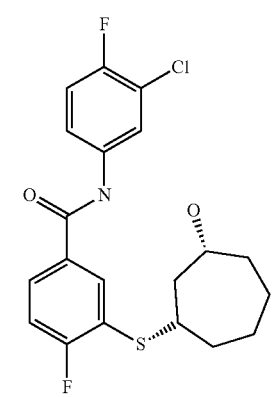
28A
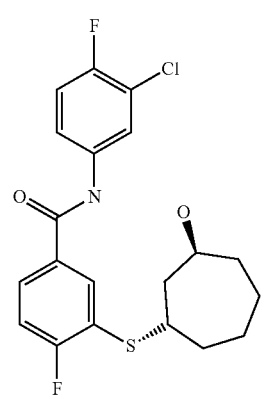
28B TABLE 1-continued
29
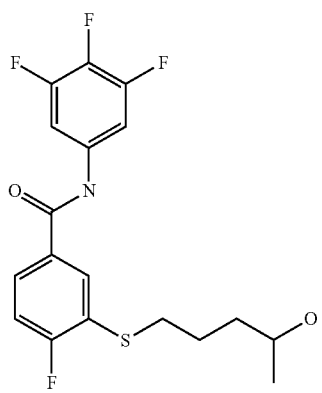 [SMILES: CC(O)CCCSc1cc(C(=O)Nc2cc(F)c(F)c(F)c2)ccc1F]
30
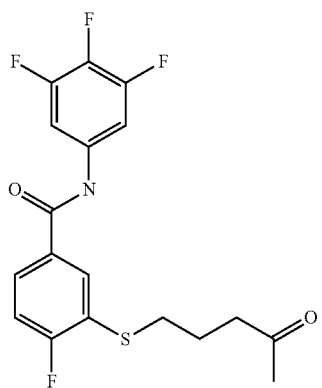 [SMILES: CC(=O)CCCSc1cc(C(=O)Nc2cc(F)c(F)c(F)c2)ccc1F]
31
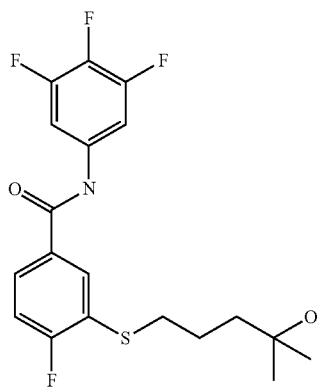 [SMILES: CC(C)(O)CCCSc1cc(C(=O)Nc2cc(F)c(F)c(F)c2)ccc1F]
32
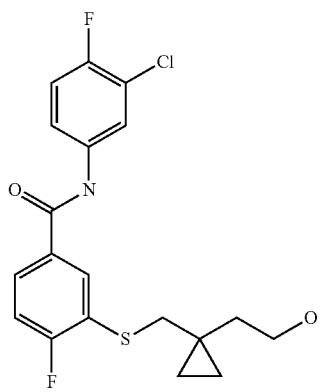 [SMILES: O=C(Nc1ccc(F)c(Cl)c1)c1ccc(F)c(SCC2(CCO)CC2)c1]
TABLE 1-continued
33
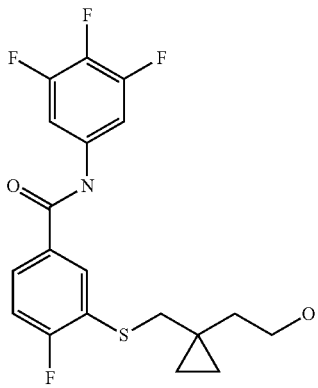 [SMILES: O=C(Nc1cc(F)c(F)c(F)c1)c1ccc(F)c(SCC2(CCO)CC2)c1]
34
35
36

TABLE 1-continued

| No. | Structure |
|---|---|
| 37 | 3-(cyclopentylthio)-N-(3-chloro-4-fluorophenyl)benzamide |
| 38 | N-(3-chloro-4-fluorophenyl)-3-((3-oxocycloheptyl)thio)benzamide |
| 39A | N-(3-chloro-4-fluorophenyl)-3-(((1S,3R)-3-hydroxycycloheptyl)thio)benzamide |
| 39B | N-(3-chloro-4-fluorophenyl)-3-(((1R,3S)-3-hydroxycycloheptyl)thio)benzamide |
| 40 | N-(3-chloro-4-fluorophenyl)-3-((3-hydroxypropyl)thio)benzamide |
| 41 | 3-((2-aminoethyl)thio)-N-(3-chloro-4-fluorophenyl)-4-fluorobenzamide |
| 42 | N-(3-chloro-4-fluorophenyl)-4-fluoro-3-((3,3,3-trifluoropropyl)thio)benzamide |
| 43 | N-(3-chloro-4-fluorophenyl)-3-((cyclohexylmethyl)thio)benzamide |

TABLE 1-continued
| | |
|---|---|
| 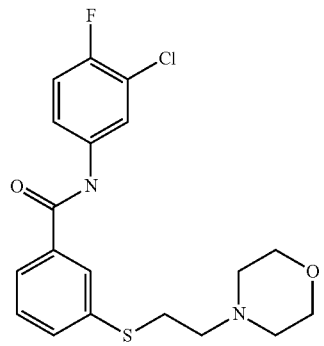 [SMILES: O=C(Nc1ccc(F)c(Cl)c1)c1cccc(SCCN2CCOCC2)c1] | 44 |
| 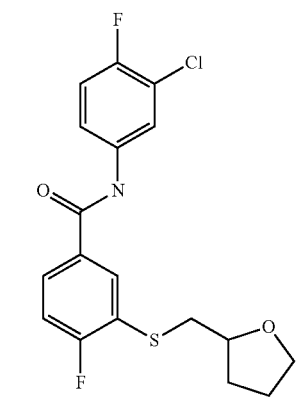 [SMILES: O=C(Nc1ccc(F)c(Cl)c1)c1ccc(F)c(SCC2CCCO2)c1] | 45 |
| 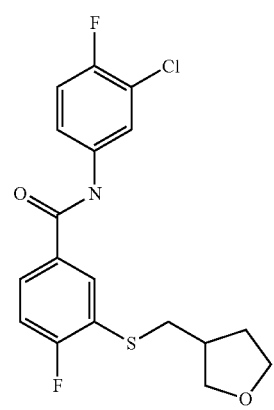 [SMILES: O=C(Nc1ccc(F)c(Cl)c1)c1ccc(F)c(SCC2CCOC2)c1] | 46 |
| 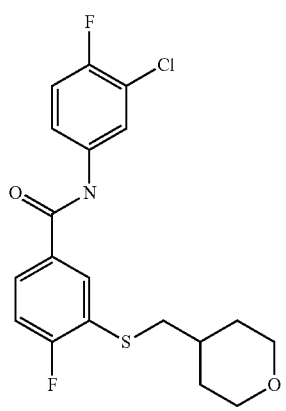 [SMILES: O=C(Nc1ccc(F)c(Cl)c1)c1ccc(F)c(SCC2CCOCC2)c1] | 47 |
TABLE 1-continued
| | |
|---|---|
| 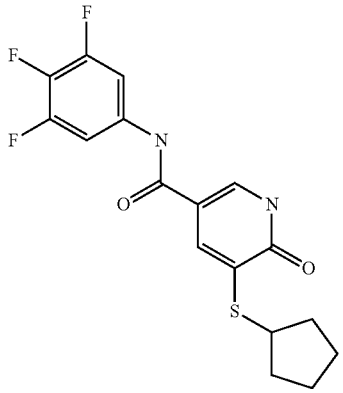 [SMILES: O=C(Nc1cc(F)c(F)c(F)c1)c1c[nH]c(=O)c(SC2CCCC2)c1] | 48 |
| 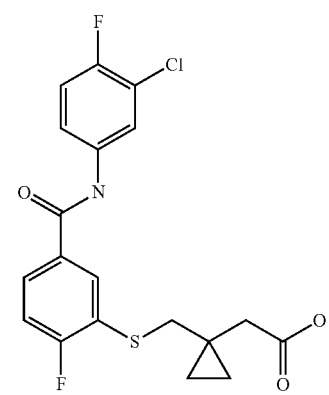 [SMILES: O=C(O)CC1(CSc2cc(C(=O)Nc3ccc(F)c(Cl)c3)ccc2F)CC1] | 49 |
| 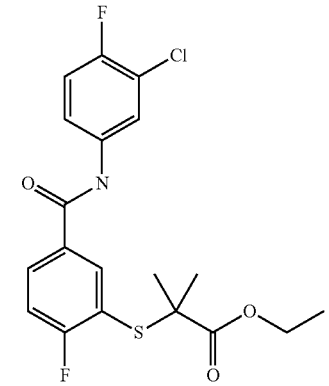 [SMILES: CCOC(=O)C(C)(C)Sc1cc(C(=O)Nc2ccc(F)c(Cl)c2)ccc1F] | 50 |
| 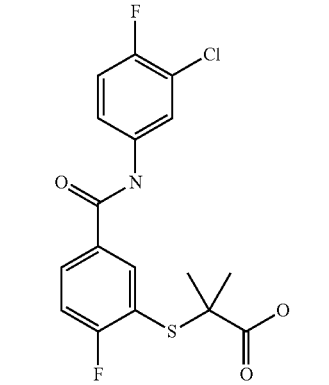 [SMILES: CC(C)(Sc1cc(C(=O)Nc2ccc(F)c(Cl)c2)ccc1F)C(=O)O] | 51 |

TABLE 1-continued
| | |
|---|---|
| 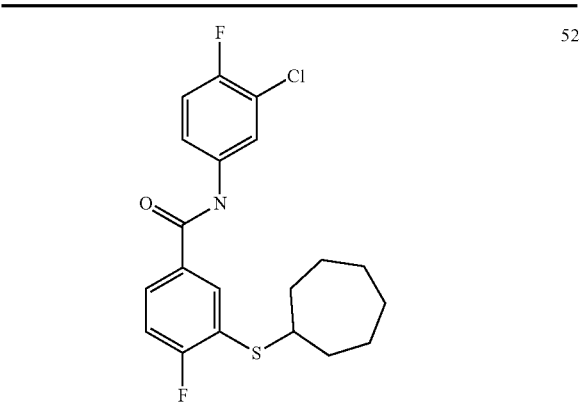 52 | 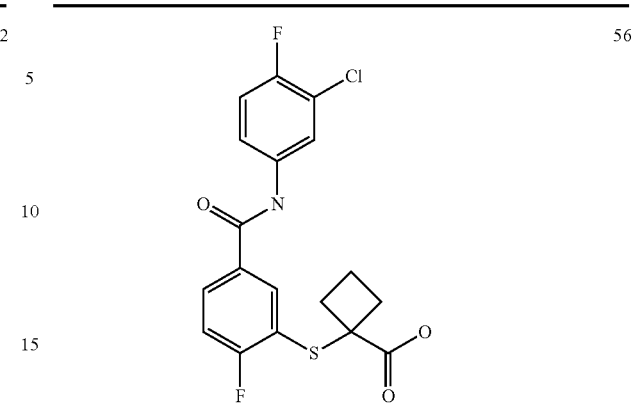 56 |
| 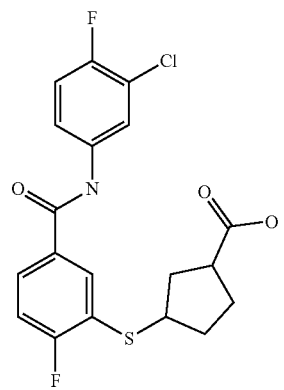 [SMILES: O=C(Nc1ccc(F)c(Cl)c1)c1ccc(F)c(SC2CCC(C(=O)O)C2)c1] 53 | 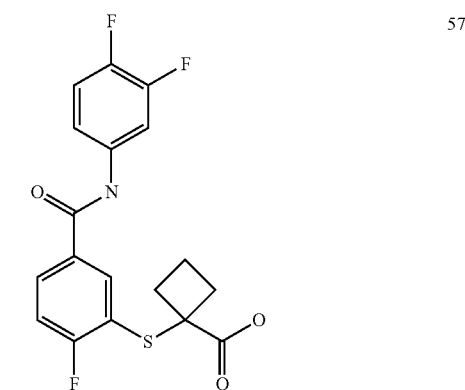 57 |
| 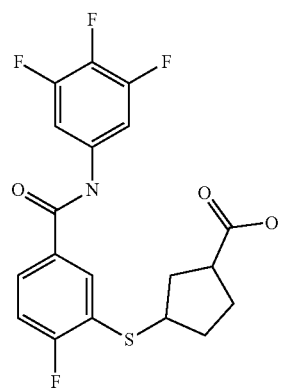 [SMILES: O=C(Nc1cc(F)c(F)c(F)c1)c1ccc(F)c(SC2CCC(C(=O)O)C2)c1] 54 | 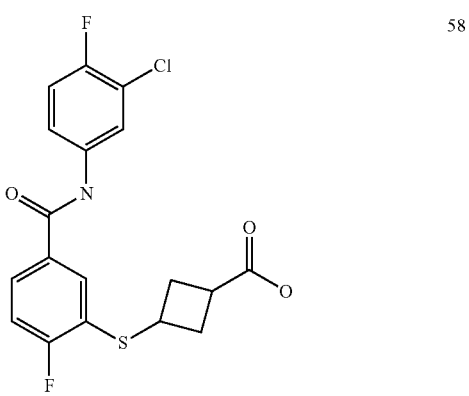 58 |
| 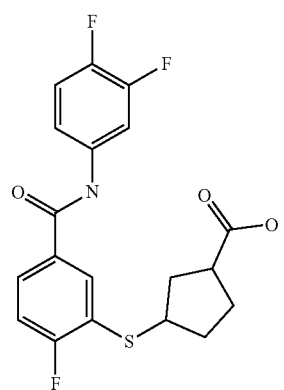 [SMILES: O=C(Nc1ccc(F)c(F)c1)c1ccc(F)c(SC2CCC(C(=O)O)C2)c1] 55 | 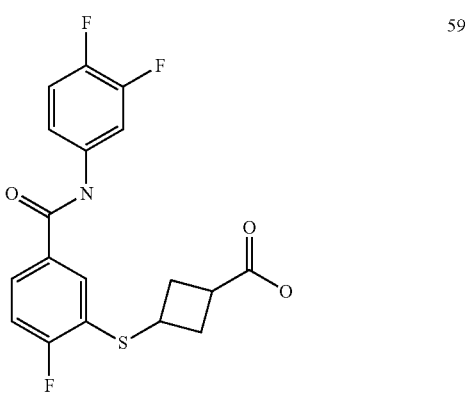 59 |

TABLE 1-continued
60 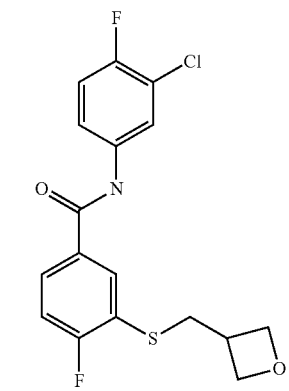 [SMILES: O=C(Nc1ccc(F)c(Cl)c1)c1ccc(F)c(SCC2COC2)c1]
61 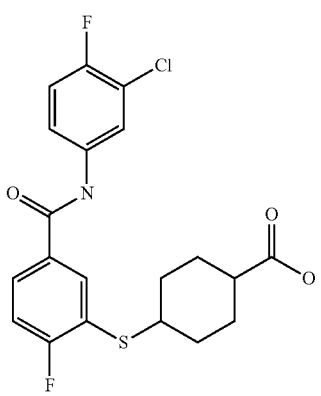 [SMILES: O=C(Nc1ccc(F)c(Cl)c1)c1ccc(F)c(SC2CCC(C(=O)O)CC2)c1]
62 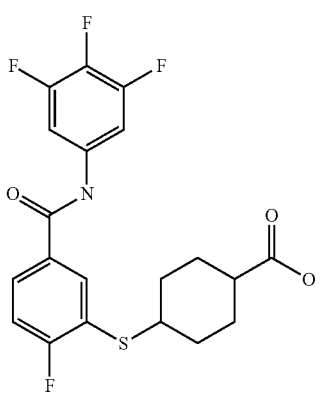 [SMILES: O=C(Nc1cc(F)c(F)c(F)c1)c1ccc(F)c(SC2CCC(C(=O)O)CC2)c1]
63 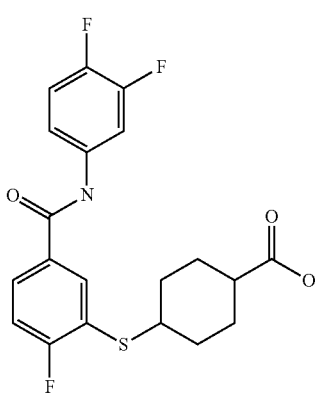 [SMILES: O=C(Nc1ccc(F)c(F)c1)c1ccc(F)c(SC2CCC(C(=O)O)CC2)c1]
TABLE 1-continued
64 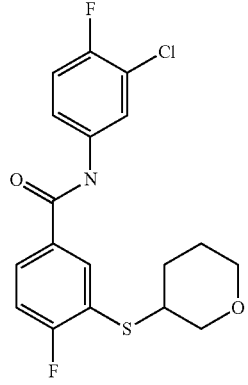 [SMILES: O=C(Nc1ccc(F)c(Cl)c1)c1ccc(F)c(SC2CCCOC2)c1]
65 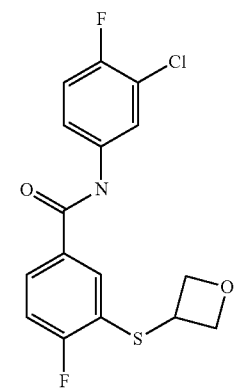 [SMILES: O=C(Nc1ccc(F)c(Cl)c1)c1ccc(F)c(SC2COC2)c1]
66 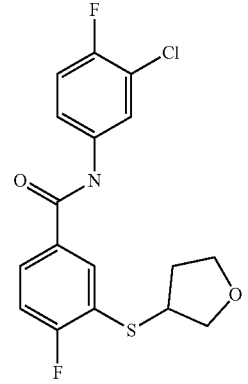 [SMILES: O=C(Nc1ccc(F)c(Cl)c1)c1ccc(F)c(SC2CCOC2)c1]
67 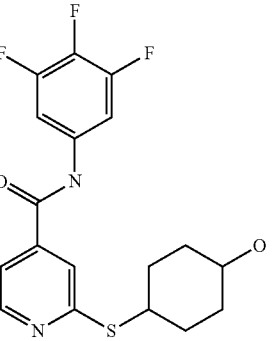

TABLE 1-continued
| | |
|---|---|
| 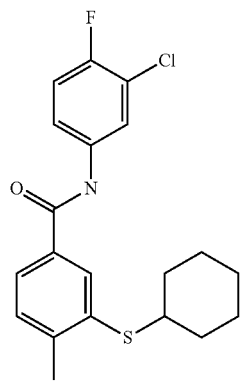 [SMILES: Cc1ccc(C(=O)Nc2ccc(F)c(Cl)c2)cc1SC1CCCCC1] 68 | 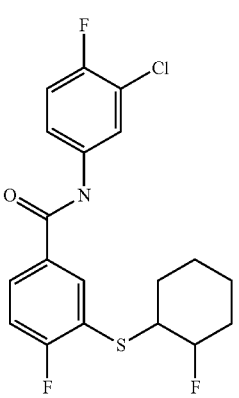 [SMILES: O=C(Nc1ccc(F)c(Cl)c1)c1ccc(F)c(SC2CCCCC2F)c1] 72 |
| 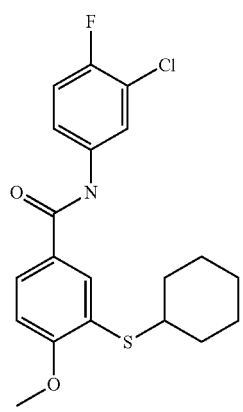 69 | 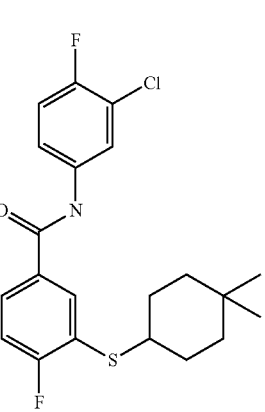 73 |
| 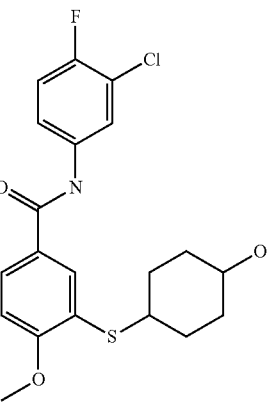 70 | 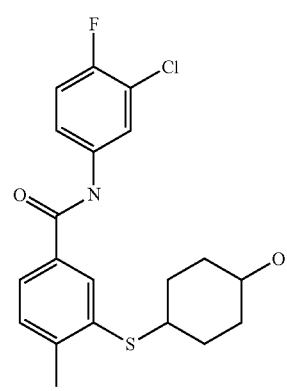 [SMILES: Cc1ccc(C(=O)Nc2ccc(F)c(Cl)c2)cc1SC1CCC(O)CC1] 74 |
| 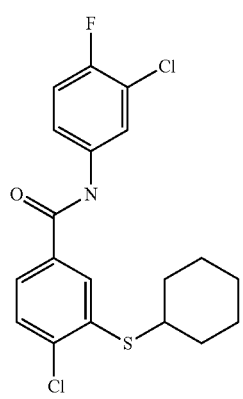 71 | 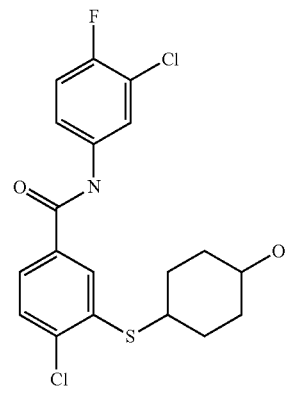 [SMILES: O=C(Nc1ccc(F)c(Cl)c1)c1ccc(Cl)c(SC2CCC(O)CC2)c1] 75 |

TABLE 1-continued
| | |
|---|---|
| 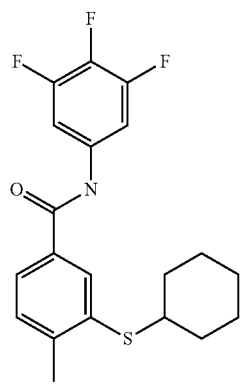 [SMILES: Cc1ccc(C(=O)Nc2cc(F)c(F)c(F)c2)cc1SC1CCCCC1] | 76 |
| 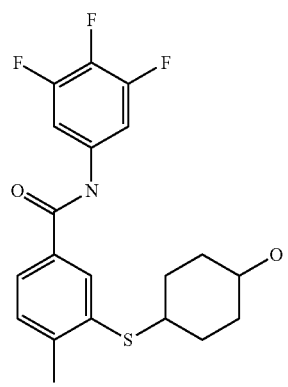 [SMILES: Cc1ccc(C(=O)Nc2cc(F)c(F)c(F)c2)cc1SC1CCC(O)CC1] | 77 |
| 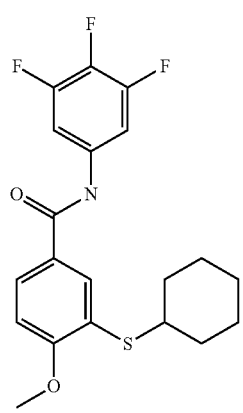 [SMILES: COc1ccc(C(=O)Nc2cc(F)c(F)c(F)c2)cc1SC1CCCCC1] | 78 |
| 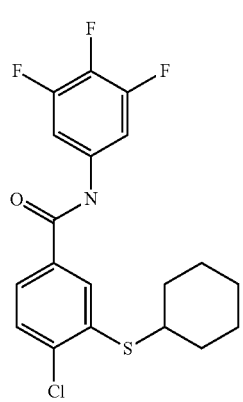 [SMILES: O=C(Nc1cc(F)c(F)c(F)c1)c1ccc(Cl)c(SC2CCCCC2)c1] | 79 |
TABLE 1-continued
| | |
|---|---|
| 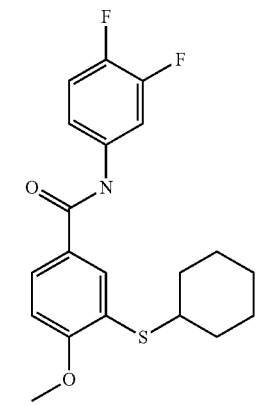 [SMILES: COc1ccc(C(=O)Nc2ccc(F)c(F)c2)cc1SC1CCCCC1] | 80 |
| 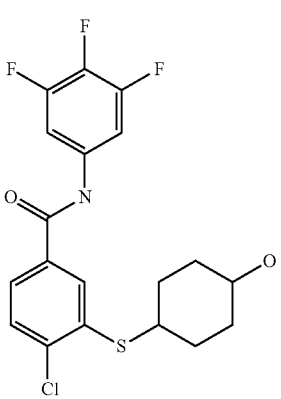 [SMILES: O=C(Nc1cc(F)c(F)c(F)c1)c1ccc(Cl)c(SC2CCC(O)CC2)c1] | 81 |
| 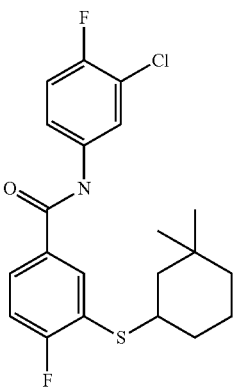 [SMILES: CC1(C)CCCC(Sc2cc(C(=O)Nc3ccc(F)c(Cl)c3)ccc2F)C1] | 82 |
| 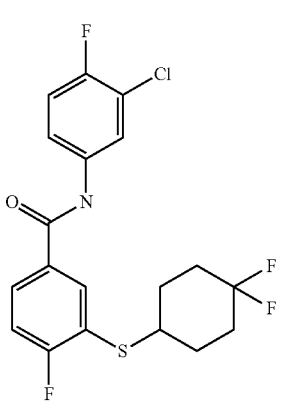 [SMILES: O=C(Nc1ccc(F)c(Cl)c1)c1ccc(F)c(SC2CCC(F)(F)CC2)c1] | 83 |

TABLE 1-continued
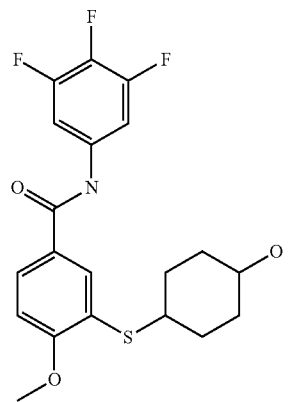 [SMILES: COc1ccc(C(=O)Nc2cc(F)c(F)c(F)c2)cc1SC1CCC(O)CC1] 84
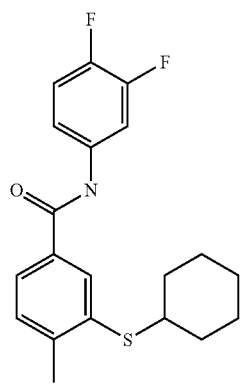 [SMILES: Cc1ccc(C(=O)Nc2ccc(F)c(F)c2)cc1SC1CCCCC1] 85
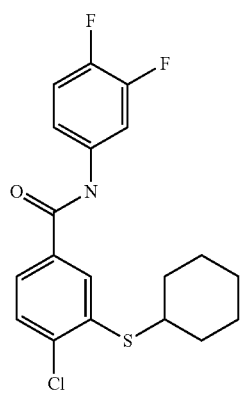 [SMILES: O=C(Nc1ccc(F)c(F)c1)c1ccc(Cl)c(SC2CCCCC2)c1] 86
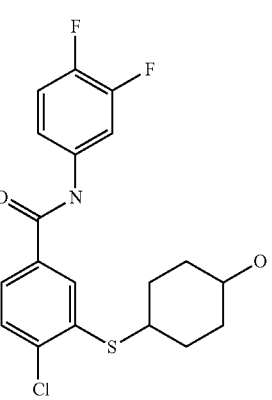 87
TABLE 1-continued
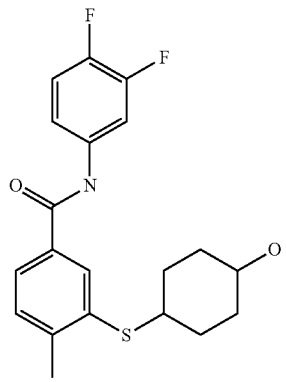 [SMILES: Cc1ccc(C(=O)Nc2ccc(F)c(F)c2)cc1SC1CCC(O)CC1] 88
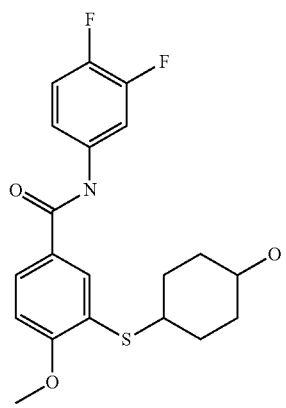 [SMILES: COc1ccc(C(=O)Nc2ccc(F)c(F)c2)cc1SC1CCC(O)CC1] 89
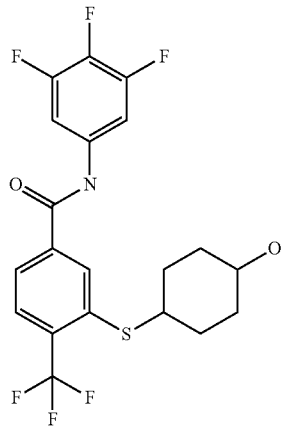 [SMILES: O=C(Nc1cc(F)c(F)c(F)c1)c1ccc(C(F)(F)F)c(SC2CCC(O)CC2)c1] 90
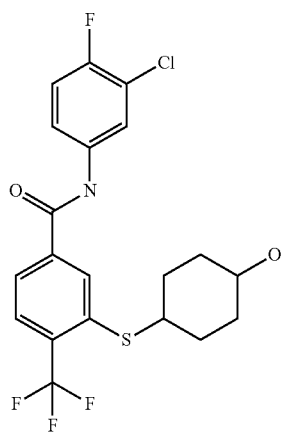 [SMILES: O=C(Nc1ccc(F)c(Cl)c1)c1ccc(C(F)(F)F)c(SC2CCC(O)CC2)c1] 91

TABLE 1-continued
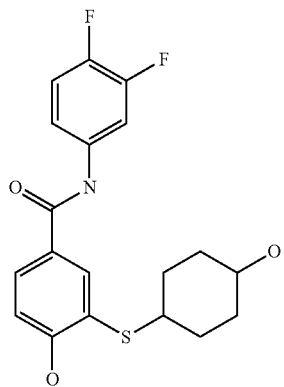 [SMILES: O=C(Nc1ccc(F)c(F)c1)c1ccc(O)c(SC2CCC(O)CC2)c1] 92
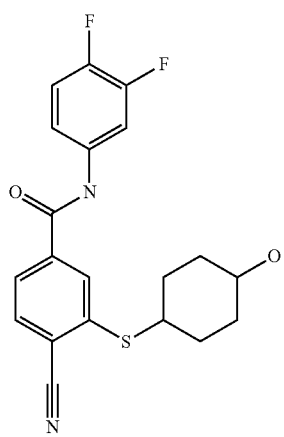 [SMILES: N#Cc1ccc(C(=O)Nc2ccc(F)c(F)c2)cc1SC1CCC(O)CC1] 93
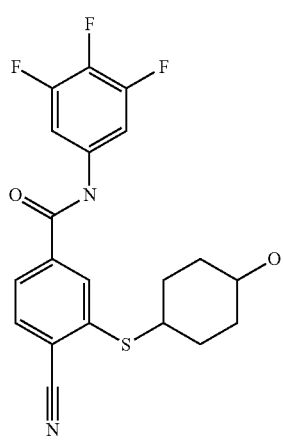 [SMILES: N#Cc1ccc(C(=O)Nc2cc(F)c(F)c(F)c2)cc1SC1CCC(O)CC1] 94
TABLE 1-continued
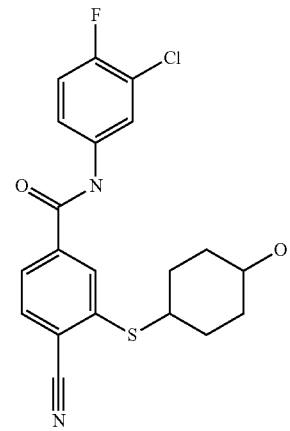 [SMILES: N#Cc1ccc(C(=O)Nc2ccc(F)c(Cl)c2)cc1SC1CCC(O)CC1] 95
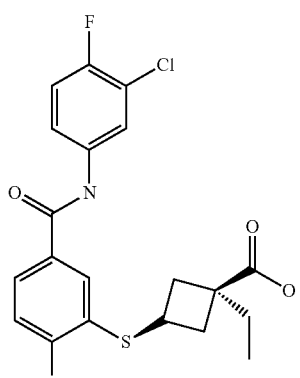 96A
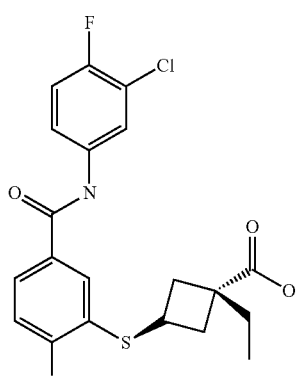 96B
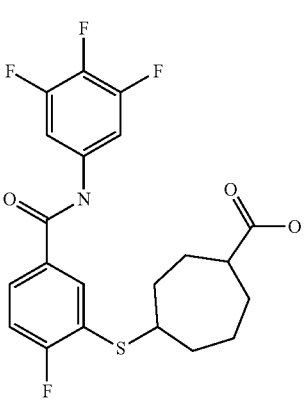 [SMILES: O=C(Nc1cc(F)c(F)c(F)c1)c1ccc(F)c(SC2CCCC(C(=O)O)CC2)c1] 97

TABLE 1-continued
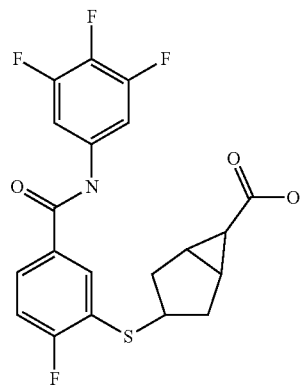 [SMILES: O=C(Nc1cc(F)c(F)c(F)c1)c1ccc(F)c(SC2CC3C(C2)C3C(=O)O)c1]
98
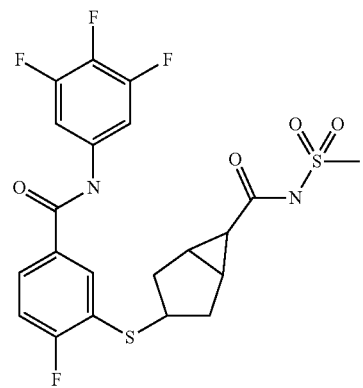 [SMILES: CS(=O)(=O)NC(=O)C1C2CC(Sc3cc(C(=O)Nc4cc(F)c(F)c(F)c4)ccc3F)CC21]
99
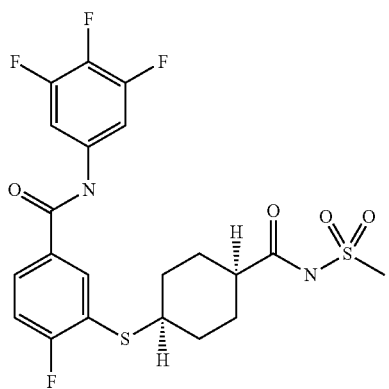 [SMILES: CS(=O)(=O)NC(=O)[C@H]1CC[C@@H](Sc2cc(C(=O)Nc3cc(F)c(F)c(F)c3)ccc2F)CC1]
100
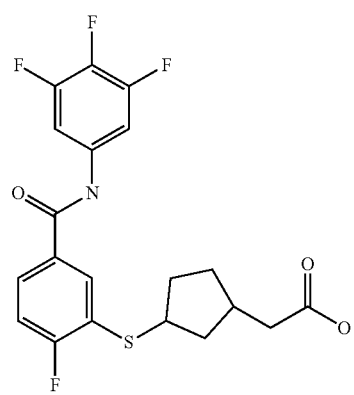 [SMILES: O=C(O)CC1CCC(Sc2cc(C(=O)Nc3cc(F)c(F)c(F)c3)ccc2F)C1]
101
TABLE 1-continued
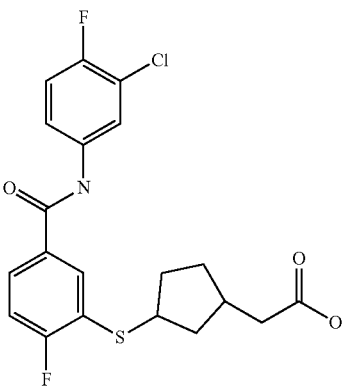 [SMILES: O=C(O)CC1CCC(Sc2cc(C(=O)Nc3ccc(F)c(Cl)c3)ccc2F)C1]
102
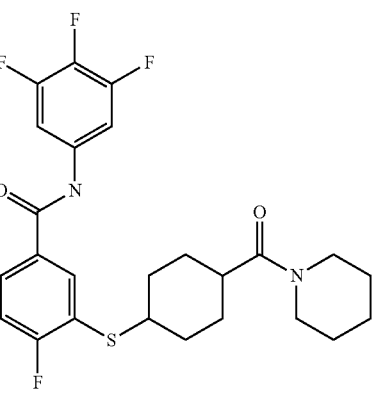
103
104
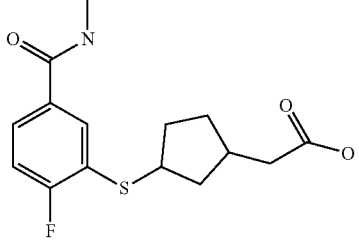
105

TABLE 1-continued
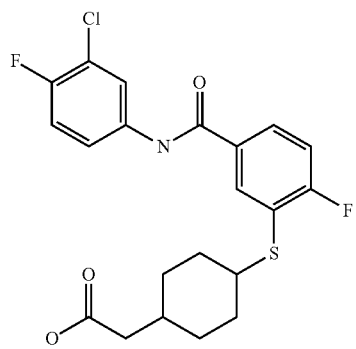 [SMILES: O=C(O)CC1CCC(Sc2cc(C(=O)Nc3ccc(F)c(Cl)c3)ccc2F)CC1]
106
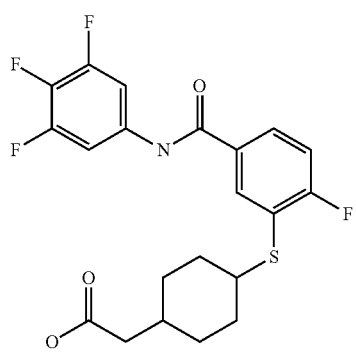 [SMILES: O=C(O)CC1CCC(Sc2cc(C(=O)Nc3cc(F)c(F)c(F)c3)ccc2F)CC1]
107
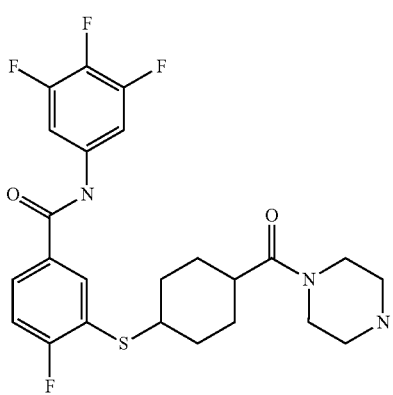 [SMILES: O=C(Nc1cc(F)c(F)c(F)c1)c1ccc(F)c(SC2CCC(C(=O)N3CCNCC3)CC2)c1]
108
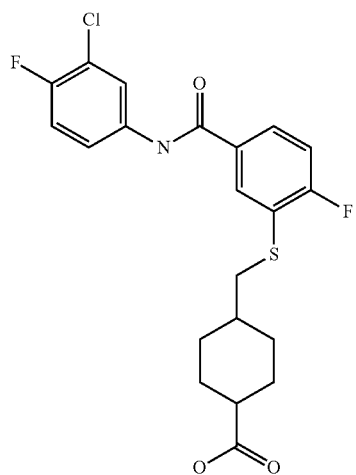 [SMILES: O=C(Nc1ccc(F)c(Cl)c1)c1ccc(F)c(SCC2CCC(C(=O)O)CC2)c1]
109
TABLE 1-continued
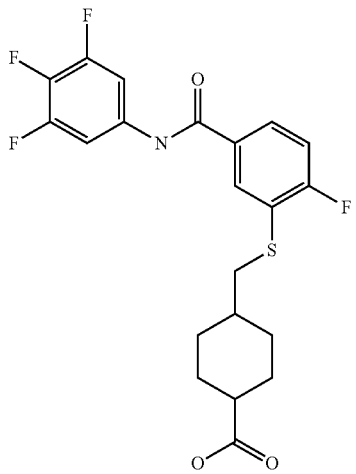 [SMILES: O=C(Nc1cc(F)c(F)c(F)c1)c1ccc(F)c(SCC2CCC(C(=O)O)CC2)c1]
110
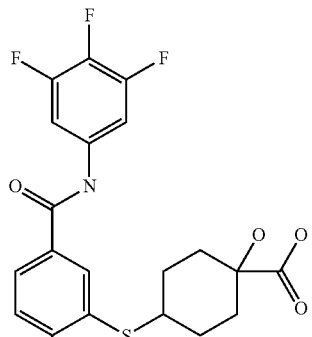
111
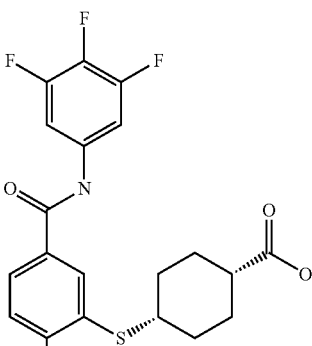
112A
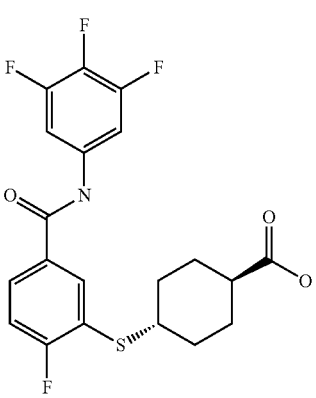 [SMILES: O=C(Nc1cc(F)c(F)c(F)c1)c1ccc(F)c(S[C@H]2CC[C@H](C(=O)O)CC2)c1]
112B TABLE 1-continued
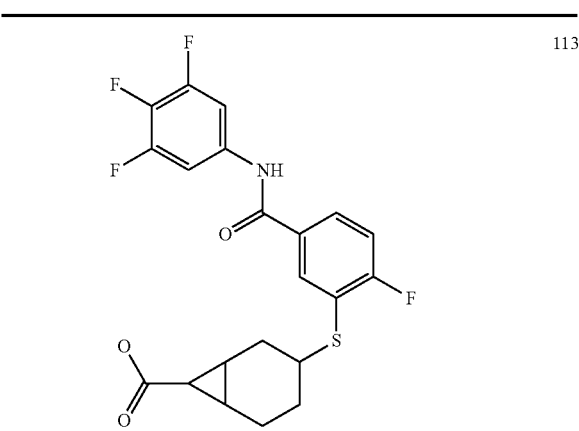
113
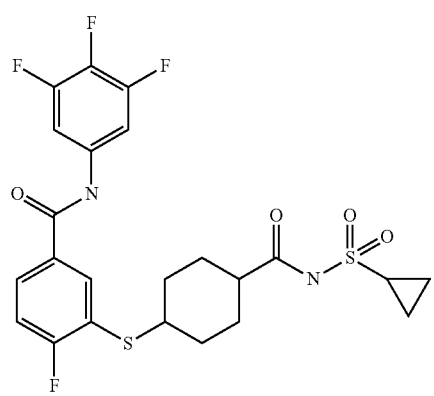 [SMILES: O=C(Nc1cc(F)c(F)c(F)c1)c1ccc(F)c(SC2CCC(C(=O)NS(=O)(=O)C3CC3)CC2)c1]
114
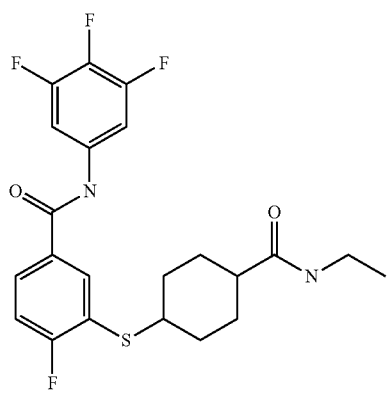 [SMILES: CCNC(=O)C1CCC(Sc2cc(C(=O)Nc3cc(F)c(F)c(F)c3)ccc2F)CC1]
115
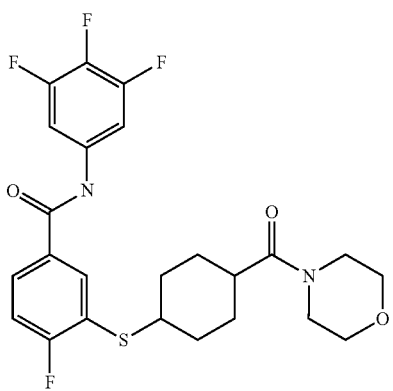
116
TABLE 1-continued
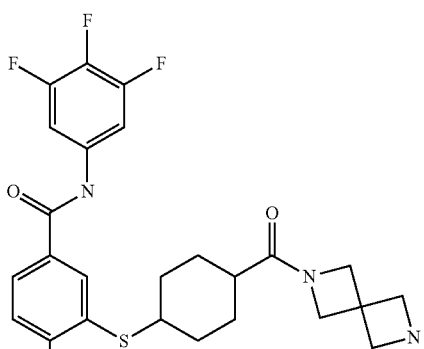
117
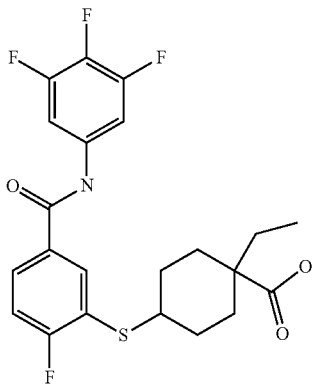 [SMILES: CCC1(C(=O)O)CCC(Sc2cc(C(=O)Nc3cc(F)c(F)c(F)c3)ccc2F)CC1]
118
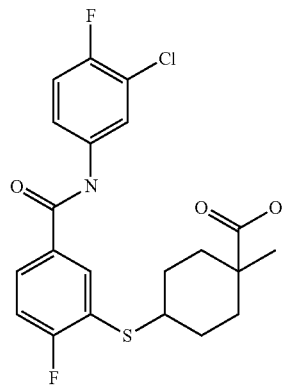 [SMILES: CC1(C(=O)O)CCC(Sc2cc(C(=O)Nc3ccc(F)c(Cl)c3)ccc2F)CC1]
119
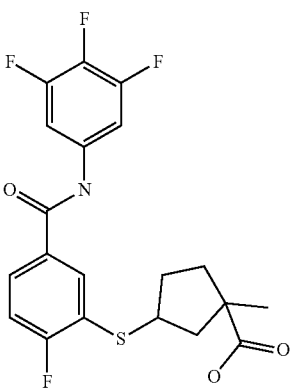 [SMILES: CC1(C(=O)O)CCC(Sc2cc(C(=O)Nc3cc(F)c(F)c(F)c3)ccc2F)C1]
120

TABLE 1-continued

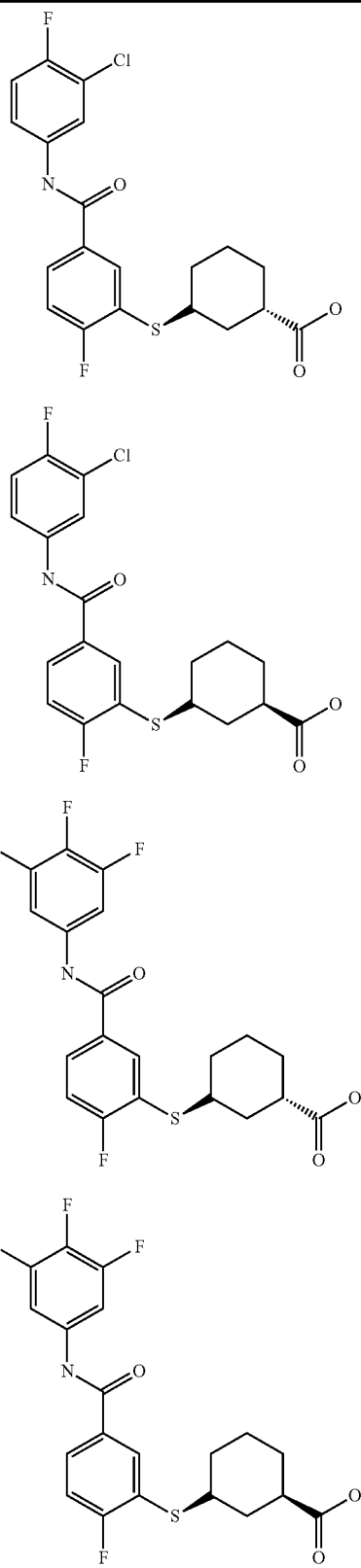

The invention further includes a composition comprising a compound according to Formula I, Formula II, Formula III, or Formula IIIa, or a salt, solvate, or N-oxide thereof. In one embodiment, the composition is pharmaceutical and further comprises at least one pharmaceutically acceptable carrier.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

Methods of Treatment

The invention includes a method of treating an HBV infection in an individual in need thereof, comprising administering to the individual a therapeutically effective amount of a compound of the invention.

The invention also includes a method of reducing the viral load associated with an HBV infection in an individual in need thereof, comprising administering to the individual a therapeutically effective amount of a compound of the invention.

The invention further includes a method of reducing reoccurrence of an HBV infection in an individual in need thereof, comprising administering to the individual a therapeutically effective amount of a compound of the invention.

The invention also includes a method of reducing an adverse physiological impact of an HBV infection in an individual in need thereof, comprising administering to the individual a therapeutically effective amount of a compound of the invention.

The invention further includes a method of inducing remission of hepatic injury from an HBV infection in an individual in need thereof, comprising administering to the individual a therapeutically effective amount of a compound of the invention.

The invention also includes a method of reducing the physiological impact of long-term antiviral therapy for HBV infection in an individual in need thereof, comprising administering to the individual a therapeutically effective amount of a compound of the invention.

The invention further includes a method of prophylactically treating an HBV infection in an individual in need thereof, wherein the individual is afflicted with a latent HBV infection, comprising administering to the individual a therapeutically effective amount of a compound of the invention.

In one embodiment, the methods described herein comprise administering to the individual at least one additional therapeutic agent selected from the group consisting of an HBV vaccine, HBV polymerase inhibitor, interferon, pegylated interferon, viral entry inhibitor, viral maturation inhibitor, capsid assembly modulator, reverse transcriptase inhibitor, a TLR-agonist, and agents of distinct or unknown mechanism, and a combination thereof. In another embodiment, the pegylated interferon is pegylated interferon alpha (IFN-α), pegylated interferon lambda (IFN-λ), or pegylated interferon gamma (IFN-γ). In still another embodiment, the reverse transcriptase inhibitor is at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, cidofovir, Efavirenz, Nevirapine, Delavirdine, or Etravirine. In yet another embodiment, the compound and the at least one additional therapeutic agent are co-formulated. In still another embodiment, the compound and the at least one additional therapeutic agent are co-administered.

In another embodiment, provided herein is a method of treating an HBV infection in an individual in need thereof, comprising administering to the individual a therapeutically effective amount of compound of Formula I, or a pharmaceutically acceptable salt thereof. In another embodiment, provided herein is a method of treating an HBV infection in an individual in need thereof, comprising administering to the individual a therapeutically effective amount of compound of Formula II, or a pharmaceutically acceptable salt thereof. In another embodiment, provided herein is a method of treating an HBV infection in an individual in need thereof, comprising administering to the individual a therapeutically effective amount of compound of Formula III, or a pharmaceutically acceptable salt thereof. In another embodiment, provided herein is a method of treating an HBV infection in an individual in need thereof, comprising administering to the individual a therapeutically effective amount of compound of Formula IIIa, or a pharmaceutically acceptable salt thereof.

In another embodiment, provided herein is a method of treating an HBV infection in an individual in need thereof, comprising administering to the individual a therapeutically effective amount of compound 110, or a pharmaceutically acceptable salt thereof.

In another embodiment, provided herein is a method of treating an HBV infection in an individual in need thereof, comprising administering to the individual a therapeutically effective amount of compound 112A, or a pharmaceutically acceptable salt thereof.

In another embodiment, provided herein is a method of treating an HBV infection in an individual in need thereof, comprising administering to the individual a therapeutically effective amount of compound 112B, or a pharmaceutically acceptable salt thereof.

In another embodiment, provided herein is a method of treating an HBV infection in an individual in need thereof, comprising administering to the individual a therapeutically effective amount of compound 116, or a pharmaceutically acceptable salt thereof.

Combination Therapies

The compounds of the present invention are intended to be useful in combination with one or more additional compounds useful for treating HBV infection. These additional compounds may comprise compounds of the present invention or compounds known to treat, prevent, or reduce the symptoms or effects of HBV infection. Such compounds include but are not limited to HBV polymerase inhibitors, interferons, viral entry inhibitors, viral maturation inhibitors, literature-described capsid assembly modulators, and other agents with distinct or unknown mechanisms that affect the HBV life cycle and/or affect the consequences of HBV infection.

In non-limiting examples, the compounds of the invention may be used in combination with one or more drugs (or a salt, solvate or prodrug thereof) selected from the group consisting of:

HBV reverse transcriptase inhibitors, and DNA and RNA polymerase inhibitors, including but are not limited to: lamivudine (3TC, Zeffix, Heptovir, Epivir, and Epivir-HBV), entecavir (Baraclude, Entavir), adefovir dipivoxil (Hepsara, Preveon, bis-POM PMEA), tenofovir disoproxil fumarate (Viread, TDF or PMPA);

interferons, including but not limited to interferon alpha (IFN-α), interferon lambda (IFN-λ), and interferon gamma (IFN-γ);

viral entry inhibitors;

viral maturation inhibitors;

literature-described capsid assembly modulators, such as but not limited to BAY 41-4109;

compounds of distinct or unknown mechanism, such as but not limited to AT-61 ((E)-N-(1-chloro-3-oxo-1-phenyl-3-(piperidin-1-yl)prop-1-en-2-yl)benzamide), AT-130 ((E)-N-(1-bromo-1-(2-methoxyphenyl)-3-oxo-3-(piperidin-1-yl) prop-1-en-2-yl)-4-nitrobenzamide), and similar analogs.

In another embodiment, the additional therapeutic agent selected from immune modulator or immune stimulator therapies, which includes biological agents belonging to the interferon class, such as interferon alpha 2a or 2b or modified interferons such as pegylated interferon, alpha 2a, alpha 2b, lamda; or TLR modulators such as TLR-7 agonists or TLR-9 agonists, or antiviral agents that block viral entry or maturation or target the HBV polymerase such as nucleoside or nucleotide or non-nucleos(t)ide polymerase inhibitors, and agents of distinct or unknown mechanism including agents that disrupt the function of other essential viral protein(s) or host proteins required for HBV replication or persistence.

In an embodiment of the combination therapy, the reverse transcriptase inhibitor and/or DNA and/or RNA polymerase inhibitor Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, cidofovir, Efavirenz, Nevirapine, Delavirdine, or Etravirine.

In another embodiment of the combination therapy, the TLR-7 agonist is selected from the group consisting of SM360320 (9-benzyl-8-hydroxy-2-(2-methoxy-ethoxy)adenine) and AZD 8848 (methyl [3-({[3-(6-amino-2-butoxy-8-oxo-7,8-dihydro-9H-purin-9-yl)propyl][3-(4-morpholinyl)propyl]amino}methyl)phenyl]acetate).

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the patient either prior to or after the onset of a HBV infection. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat HBV infection in the patient. An effective amount of the therapeutic compound necessary to achieve a therapeutic effect may vary according to factors such as the state of the disease or disorder in the patient; the age, sex, and weight of the patient; and the ability of the therapeutic compound to treat HBV infection in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of HBV infection in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin. In one embodiment, the pharmaceutically acceptable carrier is not DMSO alone.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It will be readily apparent to one skilled in the art that the frequency of administration of the various combination compositions of the invention will vary from individual to individual depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds of the invention for administration may be in the range of from about 1 μg to about 10,000 mg, about 20

µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating Parkinson's Disease) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of HBV infection in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Dosing

The therapeutically effective amount or dose of a compound of the present invention will depend on the age, sex and weight of the patient, the current medical condition of the patient and the progression of HBV infection in the patient being treated. The skilled artisan will be able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

Once improvement of the patient's conditions has occurred, a maintenance dose is administered if necessary. Subsequently, the dosage or the frequency of administration, or both, is reduced, as a function of the viral load, to a level at which the improved disease is retained. In one embodiment, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. Capsid assembly inhibitors exhibiting high therapeutic indices are preferred. The data obtained from cell culture assays and animal studies is optionally used in formulating a range of dosage for use in human. The dosage of such capsid assembly inhibitors lies preferably within a range of circulating concentrations that include the $ED_{50}$ with minimal toxicity.

The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example: Preparation of Compounds of the Invention

Figure 2:
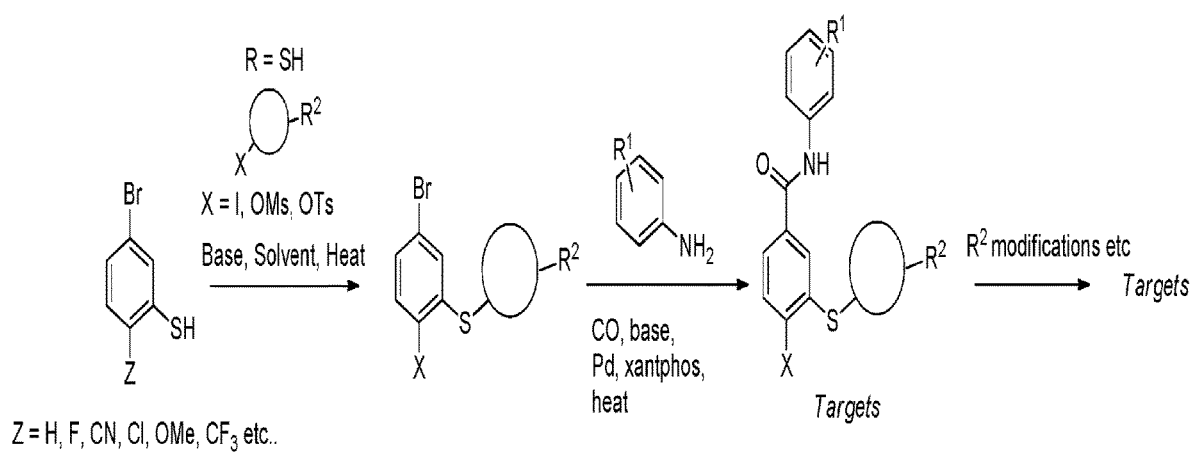
FIG. 2 shows a second general scheme used to prepare selected compounds of the invention.
Figure 3:
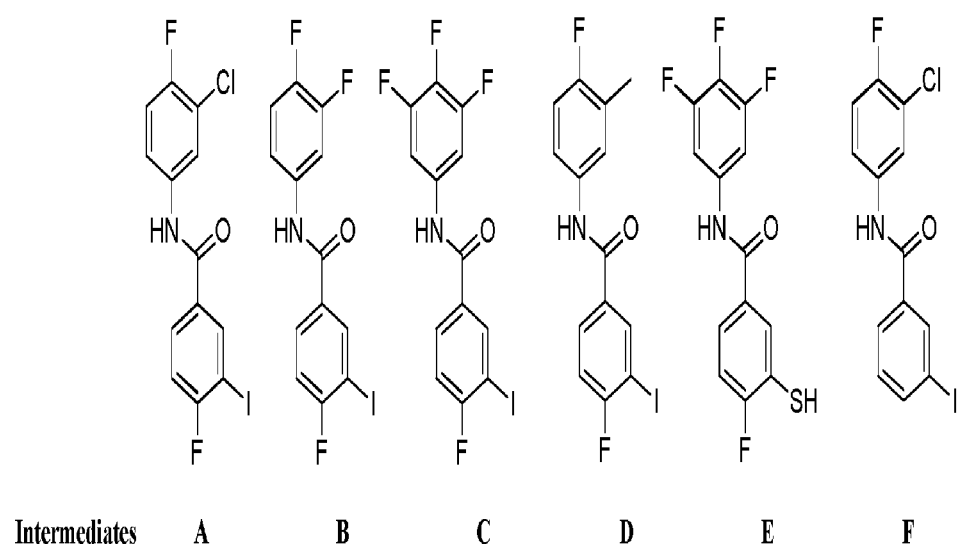
FIG. 3 shows intermediates A-F, which are used during the preparation of selected compounds of the invention.
Figure 4:
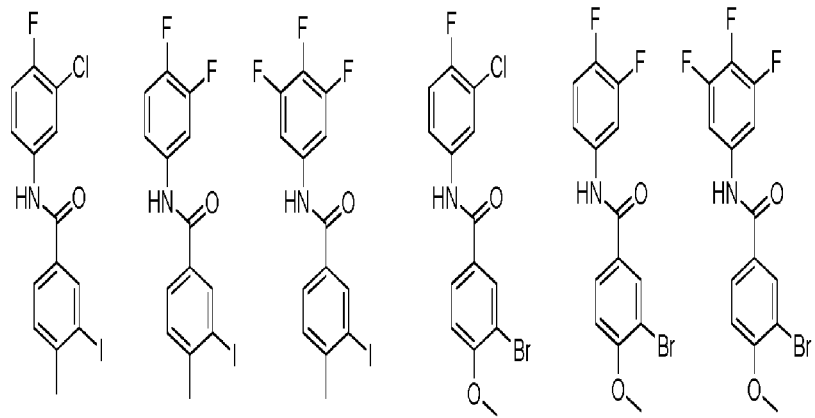
FIG. 4 shows intermediates H-V, which are used during the preparation of selected compounds of the invention.
Figure 4:
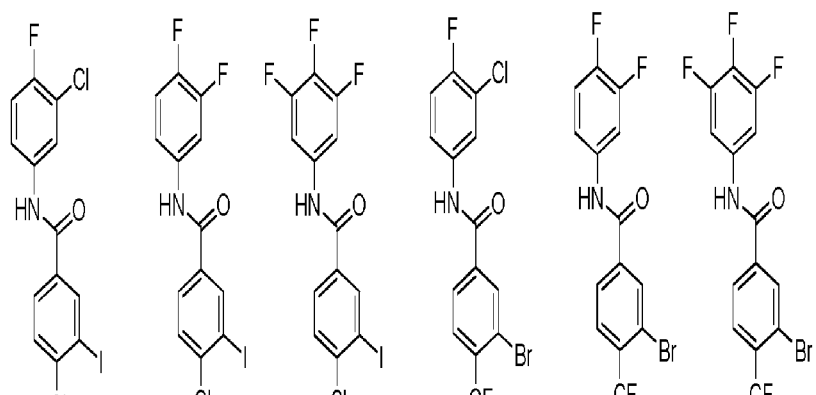
Figure 4:
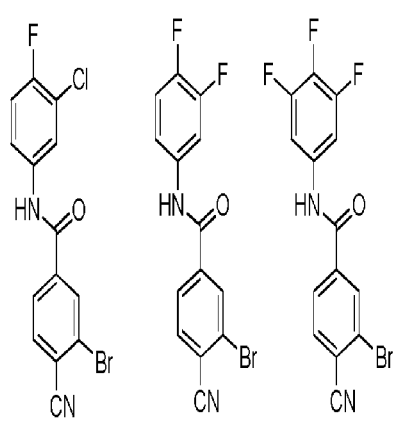

FIGS. 1 and 2 show general schemes used to prepare selected compounds of the invention. FIGS. 3 and 4 show intermediates used in the preparation of selected compounds of the invention.

Intermediate A

To a DMF (15 mL) solution of 4-fluoro-3-iodobenzene acid (2.0 g, 7.52 mmol), diisopropylethylamine (2 mL, 11.3 mmol) and 3-chloro-4-fluoroaniline (1.1 g, 7.52 mmol). The mixture was stirred at RT for 1 hour before HATU (3.54 g, 9.33 mmol) was added. The resulting solution was stirred at RT overnight, quenched with water and extracted with EtOAc. The combined organics were washed further with water and brine, dried over $Na_2SO_4$, filtered and the filtrate concentrated in vacuo. Purification by way of column chromatography ($SiO_2$, 0-50% EtOAc/hexanes afforded a white solid (2.8 g, 96% yield). LC-MS: 394 $(M+H)^+$.

Intermediate B

Prepared in an analogous manner to Intermediate A but using 3,4-difluoroaniline. LC-MS: 378 $(M+H)^+$.

Intermediate C

Prepared in an analogous manner to Intermediate A, using 3,4,5-trifluoroaniline and DMAP. Reaction mixture was also heated to 50° C. for 13 h. LC-MS: 395 $(M+H)^+$.

Intermediate D

Prepared in an analogous manner to Intermediate A but using 3-methyl-4-fluoroaniline. LC-MS: 374 $(M+H)^+$.

Intermediate E

Step 1:

A dioxane (20 mL) solution of Intermediate C (620 mg, 1.78 mmol) and diisopropylethylamine (0.450 mL, 2.67 mmol) was vigorously de-oxygenated via sub-surface purging with nitrogen for 15 min. Tris(dibenzylideneacetone)dipalladium(0) (98 mg, 0.097 mmol), xantphos (103 mg, 0.178 mmol) and 2-ethylhexyl 3-mercaptopropanoate (0.450 mL, 1.95 mmol) were then added and the reaction vessel sealed and heated at 100° C. for 13 h. After cooling to RT, the reaction mixture was diluted with ether and washed with water and brine. The organic extract was dried ($Na_2SO_4$), filtered and the filtrate concentrated in vacuo. Purification of the crude product thus obtained by way of column chromatography ($SiO_2$, 0-20% EtOAc/Hexanes) afforded the desired intermediate (757 mg, 87% yield).

Step 2:

To a THF solution (15 mL) of 2-ethylhexyl 3-((2-fluoro-5-((3,4,5-trifluorophenyl)carbamoyl)phenyl)thio)propanoate (757 mg, 1.56 mmol) was cooled to 0° C. before KOtBu (384 mg, 3.43 mmol) was added in one portion. The resulting mixture was allowed to warm to RT. The reaction mixture was diluted with ether and washed with water and brine. The organic extract was then dried over $Na_2SO_4$, filtered and the filtrate concentrated in vacuo. Purification of the crude product thus obtained by way of column chromatography (SiO2, 0-100% EtOAc/Hexanes) afforded the title compound (400 mg, 85% yield). LC-MS: 302 $(M+H)^+$.

Intermediate F

To a DMF (20 mL) solution of 3-iodobenzoic acid (2.2 g, 8.8 mmol), diisopropylamine (10 mL, 13.2 mmol) and 3-chloro-4-fluoroaniline (1.3 g, 8.8 mmol). The mixture was stirred at RT for 1 hour before HATU (4 g, 10.56 mmol) was added. The resulting solution was stirred at RT overnight after which the reaction mixture was quenched with water and extracted with EtOAc. The combined organics were washed further with water and brine, dried over $Na_2SO_4$, filtered and the filtrate concentrated in vacuo. Purification by way of column chromatography ($SiO_2$, 0-60% EtOAc/Hexanes) afforded a white solid (3 g, 94% yield). LC-MS: 375 $(M+H)^+$.

Example 1: 2-(1-(((2-Fluoro-5-((3,4,5-trifluorophenyl)carbamoyl)phenyl)thio)methyl)cyclopropyl)acetic Acid

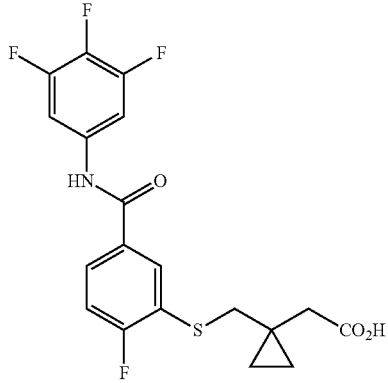 [SMILES: O=C(O)CC1(CSc2cc(C(=O)Nc3cc(F)c(F)c(F)c3)ccc2F)CC1]

To a toluene (5 mL) solution of Intermediate C (90 mg, 0.259 mmol) was added diisopropylethylamine (0.090 mL, 0.518 mmol) and vigorously de-oxygenated via sub-surface purging with nitrogen for 15 min. Tris(dibenzylideneacetone)dipalladium(0) (6.5 mg, 0.0064 mmol), xantphos (8 mg, 0.0129 mmol) and 1-(mercaptomethyl)cyclopropyl acetic acid (38 mg, 0.259 mmol) was then added and the reaction vessel was sealed and heated at 102° C. for 13 h. After cooling to RT, the reaction mixture was diluted with ether and washed sequentially with 1N HCl, water and brine. The organic extract was then dried over $Na_2SO_4$, filtered and the filtrate concentrated in vacuo. Purification of the crude product thus obtained by way of column chromatography ($SiO_2$, 0-100% EtOAc/Hexanes) afforded desired product (92 mg, 86% yield). LC-MS: 414 $(M+H)^+$.

Example 2: 3-(Cyclohexylthio)-4-fluoro-N-(3,4,5-trifluorophenyl)benzamide

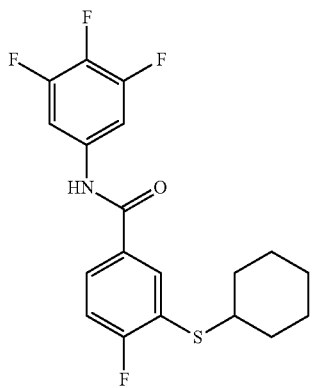 [SMILES: O=C(Nc1cc(F)c(F)c(F)c1)c1ccc(F)c(SC2CCCCC2)c1]

Prepared in an analogous manner to Example 1 but using instead cyclohexanethiol. LC-MS: 384 $(M+H)^+$.

Example 3: 3-(Cyclopentylthio)-4-fluoro-N-(3,4,5-trifluorophenyl)benzamide

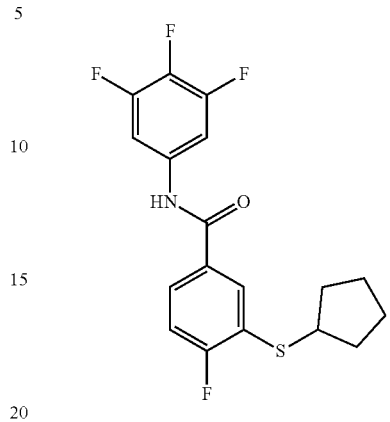

Prepared in an analogous manner to Example 1 but using instead cyclopentanethiol. LC-MS: 370 $(M+H)^+$.

Example 4: 4-Fluoro-3-((tetrahydro-2H-pyran-4-yl)thio)-N-(3,4,5-trifluorophenyl)benzamide

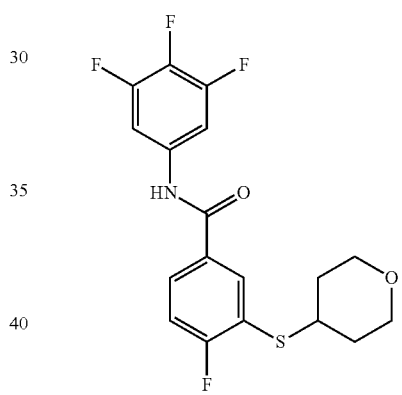

Prepared in an analogous manner to Example 1 but using instead oxane-4-thiol. LC-MS: 386 $(M+H)^+$.

Example 5: 3-(tert-Butylthio)-4-fluoro-N-(3,4,5-trifluorophenyl)benzamide

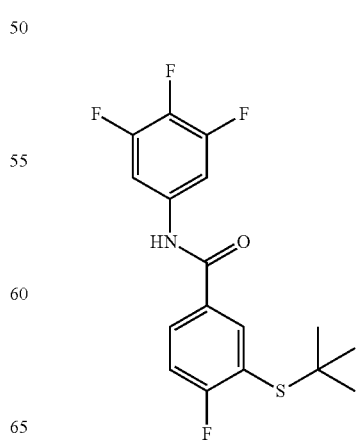

Prepared in an analogous manner to Example 1 but using instead 2-methyl-2-propanethiol. LC-MS: 358 (M+H)+.

Example 6: 3-(Benzylthio)-4-fluoro-N-(3,4,5-trifluorophenyl)benzamide

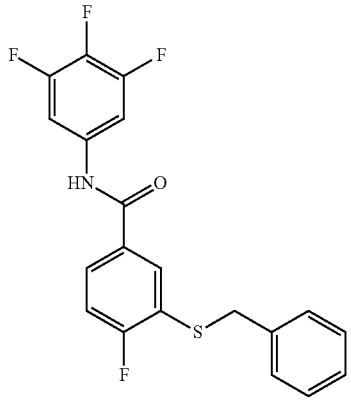 [SMILES: O=C(Nc1cc(F)c(F)c(F)c1)c1ccc(F)c(SCc2ccccc2)c1]

Prepared in an analogous manner to Example 1 but using instead benzyl mercaptan. LC-MS: 392 (M+H)+.

Example 7: 4-Fluoro-3-((2-hydroxyethyl)thio)-N-(3,4,5-trifluorophenyl)benzamide

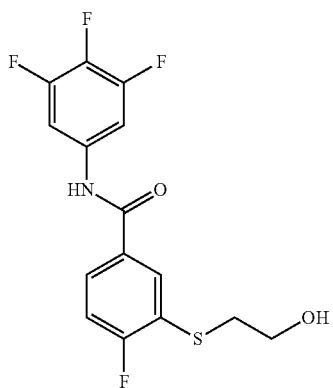 [SMILES: O=C(Nc1cc(F)c(F)c(F)c1)c1ccc(F)c(SCCO)c1]

Prepared in an analogous manner to Example 1 but using instead 2-mercaptoethanol. LC-MS: 346 (M+H)+.

Example 8: 3-(Cyclohexylthio)-4-fluoro-N-(4-fluoro-3-methylphenyl)benzamide

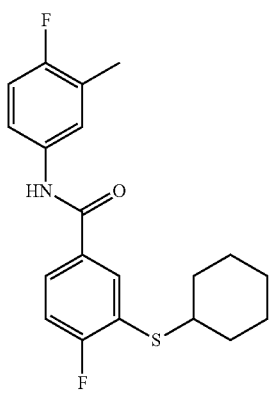 [SMILES: Cc1cc(NC(=O)c2ccc(F)c(SC3CCCCC3)c2)ccc1F]

Prepared in an analogous manner to Example 1 but using instead Intermediate D and cyclohexanethiol. LC-MS: 362 (M+H)+.

Example 9: 3-(Cyclopentylthio)-4-fluoro-N-(4-fluoro-3-methylphenyl)benzamide

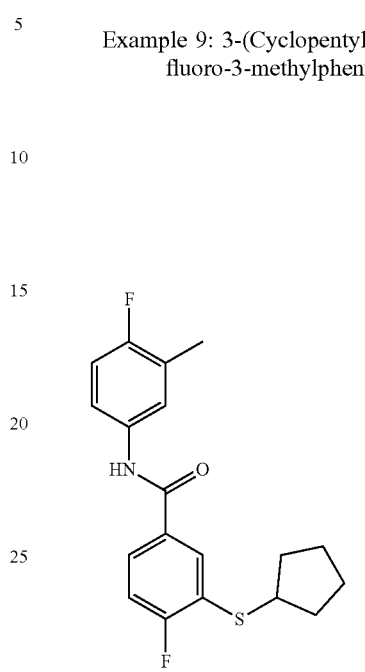

Prepared in an analogous manner to Example 1 but using instead Intermediate D and cyclopentanethiol. LC-MS: 348 (M+H)+.

Example 10: (cis/trans)-4-Fluoro-3-((4-hydroxycyclohexyl)thio)-N-(3,4,5-trifluorophenyl)benzamide

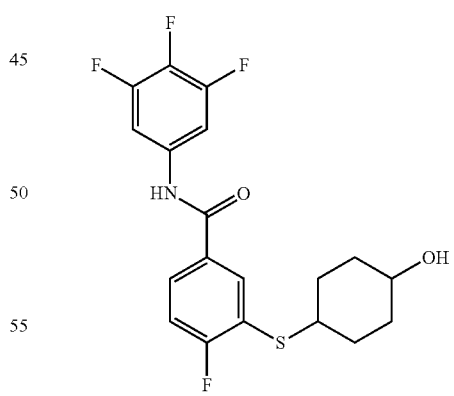

Step 1:

4-mercaptocyclohexanol was prepared according to procedure described in E. J. Corey et. al. *J. Org. Chem.* 1966, 31, 1663.

Step 2:

Prepared in an analogous manner to Example 1 but using instead 4-mercaptocyclohexanol. LC-MS: 400 (M+H)+.

Example 11: (cis/trans)-4-Fluoro-N-(4-fluoro-3-methylphenyl)-3-((4-hydroxycyclohexyl)thio)benzamide

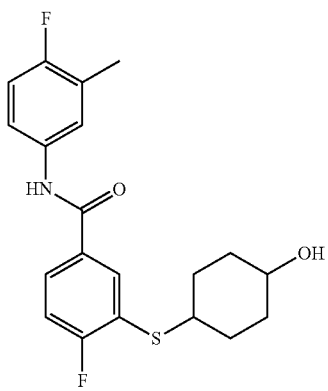 [SMILES: Cc1cc(NC(=O)c2ccc(F)c(SC3CCC(O)CC3)c2)ccc1F]

Step 1:

Prepared in an analogous manner to Example 10 but using instead Intermediate D. LC-MS: 378 (M+H)+.

Example 12: (±)-4-Fluoro-3-((3-oxocycloheptyl)thio)-N-(3,4,5-trifluorophenyl)benzamide

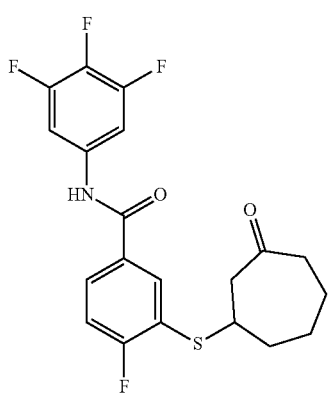 [SMILES: O=C1CCCCC(Sc2cc(C(=O)Nc3cc(F)c(F)c(F)c3)ccc2F)C1]

To a THF (15 mL) solution of Intermediate E (40 mg, 0.133 mmol) and triethylamine (0.03 mL, 0.199 mmol), cyclohep-2-en-1-one (0.016 mL, 0.146 mmol) was added. The resulting mixture stirred at RT for 3 h. The reaction mixture was diluted with ether and washed with water and brine. The organic extract was then dried over Na$_2$SO$_4$, filtered and the filtrate concentrated in vacuo. The crude product thus obtained was then purified by preparative HPLC to afford the title compound. LC-MS: 412 (M+H)+.

Example 13: (±)-N-(3-Chloro-4-fluorophenyl)-4-fluoro-3-((3-oxocycloheptyl)thio)benzamide

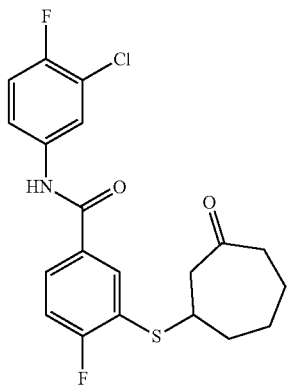 [SMILES: O=C1CCCCC(Sc2cc(C(=O)Nc3ccc(F)c(Cl)c3)ccc2F)C1]

Step 1:

To a stirred solution of 3-chlorosulfonyl-4-fluoro-benzoic acid (6.2 g, 26.0 mmol) was added concentrated HCl (20 mL) and tin(II) chloride dihydrate (18 g, 91 mmol) was heated at 100° C. for 13 h. After cooling to RT, the reaction mixture was diluted with water and basified with sat. NaHCO$_3$ and filtered. The filtrate was acidified with 1N HCl and extracted with DCM twice. Combined organics were then washed further with brine and the organic phase was then dried over Na$_2$SO$_4$, filtered and the filtrate concentrated in vacuo. No further purification was necessary to afford 4-fluoro-3-mercaptobenzoic acid (3.5 g, 80% yield)

Step 2:

To a THF (15 mL) solution of 4-fluoro-3-mercaptobenzoic acid (48 mg, 0.279 mmol) and triethylamine (0.056 mL, 0.307 mmol), cyclohept-2-en-1-one (0.035 mL, 0.307 mmol) was added. The resulting mixture stirred at RT for 3 h or until the intermediate, 4-fluoro-3-((3-oxocycloheptyl)thio)benzoic acid was formed. In the same reaction vessel, 3-chloro-4-fluoroaniline (41 mg, 0.279 mmol) and triethylamine (0.056 mL, 0.307 mmol) were added and stirred at RT for 1 h before HATU (127 mg, 0.334 mmol) was added. The resulting mixture was stirred at RT for 13 h after which the reaction mixture was washed with water and EtOAc. Combined organics were then washed further with brine and the organic phases were dried over Na$_2$SO$_4$, filtered and the filtrate concentrated in vacuo. The crude product thus obtained was then purified by preparative HPLC to afford the title compound. LC-MS: 410 (M+H)+.

Examples 14A: (±)-4-Fluoro-3-(((1S,3R)-3-hydroxycycloheptyl)thio)-N-(3,4,5-trifluorophenyl)benzamide and 14B: (±)-4-Fluoro-3-(((1R,3R)-3-hydroxycycloheptyl)thio)-N-(3,4,5-trifluorophenyl)benzamide

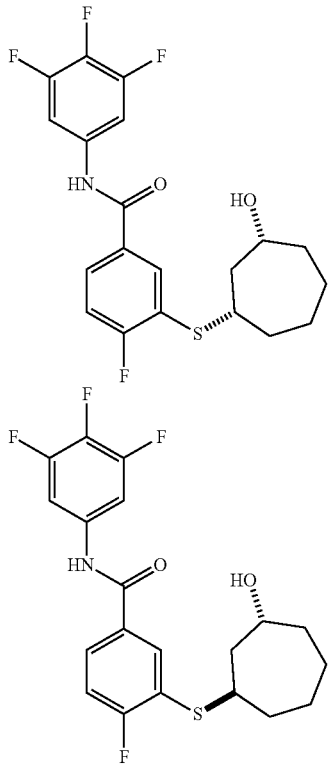

To a MeOH (10 mL) solution of Example 12 (350 mg, 0.855), was cooled to 0° C. before NaBH₄ (50 mg, 1.28 mmol) was added. The resulting mixture was allowed to warm to RT for 13 h. The reaction mixture was quenched with 1N HCl and extracted with EtOAC twice. The combined organics were then washed further with brine and the organic extract was then dried over Na₂SO₄, filtered and the filtrate concentrated in vacuo. The crude product thus obtained was then purified by preparative HPLC to afford the 2 isolated diastereomers as white solids, cis (35 mg, 10% yield) and trans (79 mg, 25%) LC-MS: 414 (M+H)⁺.

Example 15: (±)-4-Fluoro-3-((3-fluorocycloheptyl)thio)-N-(3,4,5-trifluorophenyl)benzamide

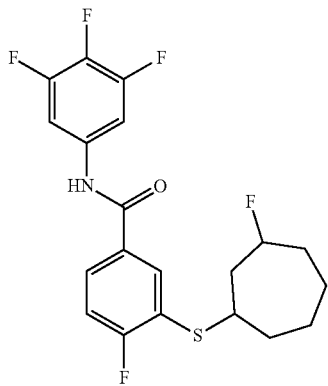 [SMILES: O=C(Nc1cc(F)c(F)c(F)c1)c1ccc(F)c(SC2CCCCC(F)C2)c1]

To a DCM (5 mL) solution of Example 14 (240 mg, 0.581 mmol) was cooled to −78° C. before DAST (0.077 mL, 0.581 mmol) was added. The resulting mixture was allowed to warm to RT over 13 h. Reaction mixture was quenched with sat. NaHCO₃ and extracted with DCM. The combined organics were then washed further with water and brine, dried over Na₂SO₄, filtered and the filtrate concentrated in vacuo. Purification of the crude product thus obtained by way of column chromatography (SiO₂, 0-50% EtOAc/Hexanes) afforded the title compound (98 mg, 3% yield). LC-MS: 416 (M+H)⁺.

Example 16: (±)-4-Fluoro-3-(((1R,3S)-3-hydroxy-3-methylcycloheptyl)thio)-N-(3,4,5-trifluorophenyl)benzamide

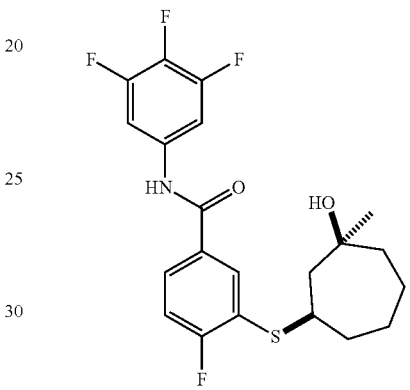

To a THF (5 mL) solution of Example 12 (86 mg, 0.209 mmol) cooled to 0° C. was added methyl magnesium bromide (3M, 0.210 mL, 0.63 mmol). After stirring at 0° C. for 30 minutes, the mixture was allowed to warm to room temperature after which it was washed sequentially with 1N HCl, 1N NaOH and extracted with EtOAC twice. The combined organics were then washed further with water and brine, dried over Na₂SO₄, filtered and the filtrate concentrated in vacuo. The crude product thus obtained was then purified by preparative HPLC to afford the title compound. LC-MS: 428 (M+H)⁺.

Example 17: 4-Fluoro-3-((3-hydroxypropyl)thio)-N-(3,4,5-trifluorophenyl)benzamide

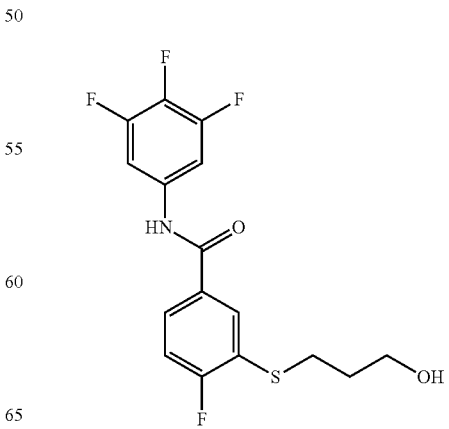

Prepared in an analogous manner to Example 1 but using instead 3-mercapto-1-propanol. LC-MS: 360 (M+H)+.

Example 18: (±)-4-Fluoro-3-((3-hydroxybutyl)thio)-N-(3,4,5-trifluorophenyl)benzamide

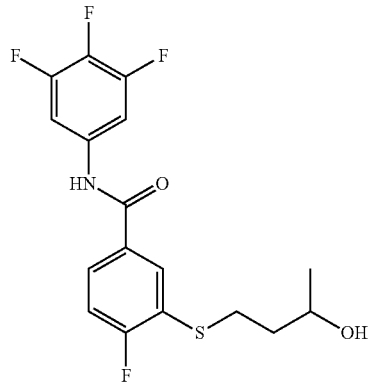 [SMILES: CC(O)CCSc1cc(C(=O)Nc2cc(F)c(F)c(F)c2)ccc1F]

Step 1:

To a THF (5 mL) solution of Example 17 (200 mg, 0.557 mmol), Dess-Martin periodinane (236 mg, 0.557 mmol) was added and the mixture stirred at RT for 16 h. The reaction mixture was washed with sat. NaHCO$_3$ and extracted with DCM and then washed further with water and brine. Organic extract was then dried over Na$_2$SO$_4$, filtered and the filtrate concentrated in vacuo. Purification of the crude product thus obtained by way of column chromatography (SiO$_2$, 0-100% EtOAc/Hexanes) afforded the aldehyde (80 mg, 42% yield).

Step 2:

Prepared in an analogous manner to Example 16 but using the aldehyde in the previous step as the Intermediate. LC-MS: 374 (M+H)+.

Example 19: 4-Fluoro-3-((3-hydroxy-3-methylbutyl)thio)-N-(3,4,5-trifluorophenyl)benzamide

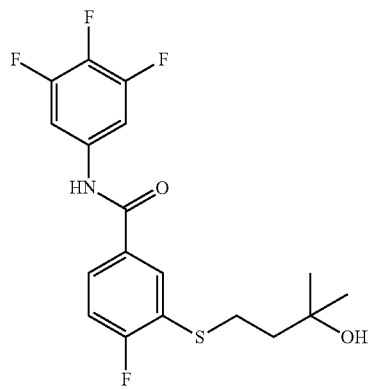 [SMILES: CC(C)(O)CCSc1cc(C(=O)Nc2cc(F)c(F)c(F)c2)ccc1F]

Prepared in an analogous manner to Example 18 but using Example 18 as the Intermediate. LC-MS: 388 (M+H)+.

Example 20: (±)-N-(3-Chloro-4-fluorophenyl)-4-fluoro-3-((3-oxocyclohexyl)thio)benzamide

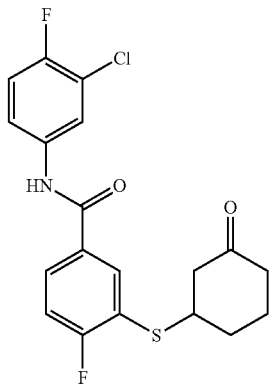 [SMILES: O=C1CCCC(Sc2cc(C(=O)Nc3ccc(F)c(Cl)c3)ccc2F)C1]

Prepared in an analogous manner to Example 13 but using instead 2-cyclohexen-1-one. LC-MS: 396 (M+H)+.

Example 21: (±)-N-(3-Chloro-4-fluorophenyl)-4-fluoro-3-(((1R,3R)-3-hydroxycyclohexyl)thio)benzamide

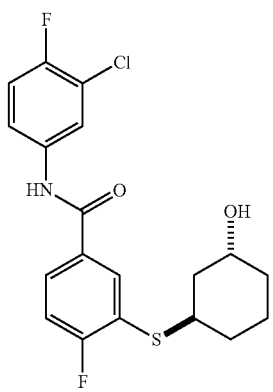

Prepared in an analogous manner to Example 14 but using Example 20 as the intermediate. LC-MS: 398 (M+H)+.

Example 22: (±)-N-(3-Chloro-4-fluorophenyl)-4-fluoro-3-((3-oxocyclopentyl)thio)benzamide

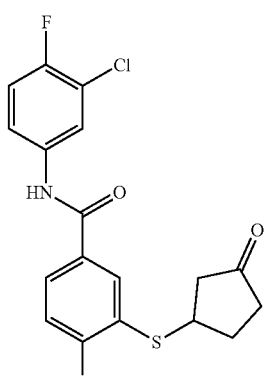

Prepared in an analogous manner to Example 13 but using instead cyclopent-2-en-one. LC-MS: 396 (M+H)+.

Example 23: 4-Fluoro-3-((4-hydroxybutyl)thio)-N-(3,4,5-trifluorophenyl)benzamide

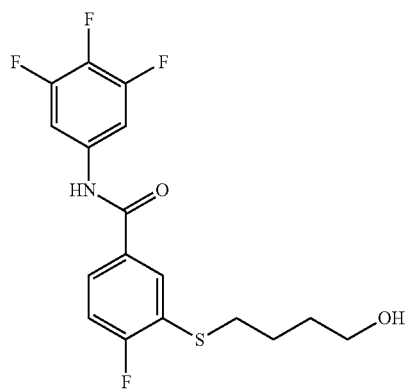 [SMILES: O=C(Nc1cc(F)c(F)c(F)c1)c1ccc(F)c(SCCCCO)c1]

Prepared in an analogous manner to Example 1 but using instead 4-mercapto-1-butanol. LC-MS: 374 (M+H)⁺.

Example 24: (cis/trans)-N-(3-Chloro-4-fluorophenyl)-4-fluoro-3-((4-hydroxycyclohexyl)thio)benzamide

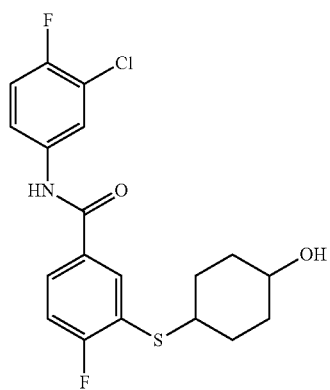

Prepared in an analogous manner to Example 10 but using instead Intermediate A. LC-MS: 398 (M+H)⁺.

Example 25: (±)-N-(3-Chloro-4-fluorophenyl)-4-fluoro-3-(((1S,3S)-3-hydroxycyclopentyl)thio)benzamide

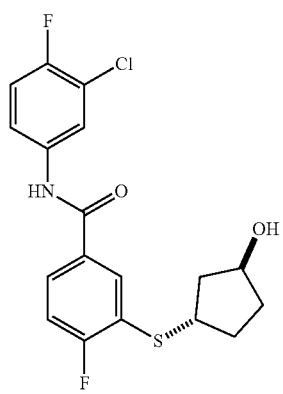

Prepared in an analogous manner to Example 21 but using Example 22 as the Intermediate. LC-MS: 384 (M+H)⁺.

Example 26: N-(3-Chloro-4-fluorophenyl)-4-fluoro-3-((2-hydroxyethyl)thio)benzamide

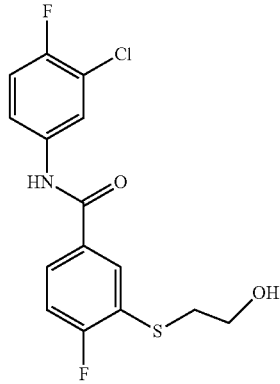 [SMILES: O=C(Nc1ccc(F)c(Cl)c1)c1ccc(F)c(SCCO)c1]

Prepared in an analogous manner to Example 7 but using instead Intermediate A. LC-MS: 344 (M+H)⁺.

Example 27: N-(3-Chloro-4-fluorophenyl)-4-fluoro-3-((3-hydroxypropyl)thio)benzamide

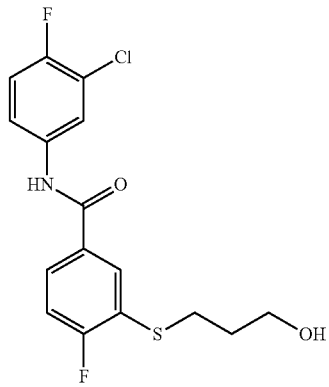 [SMILES: O=C(Nc1ccc(F)c(Cl)c1)c1ccc(F)c(SCCCO)c1]

Prepared in an analogous manner to Example 17 but using instead Intermediate A. LC-MS: 358 (M+H)⁺.

Example 28A: (±)-N-(3-Chloro-4-fluorophenyl)-4-fluoro-3-(((1S,3R)-3-hydroxycycloheptyl)thio)benzamide

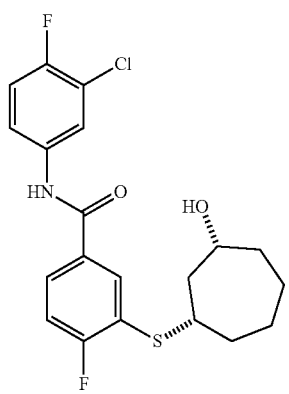

Prepared in an analogous manner to Example 14A but using instead Intermediate A. LC-MS: 412 (M+H)+.

Example 28B: (±)-N-(3-Chloro-4-fluorophenyl)-4-fluoro-3-(((1S,3S)-3-hydroxycycloheptyl)thio)benzamide

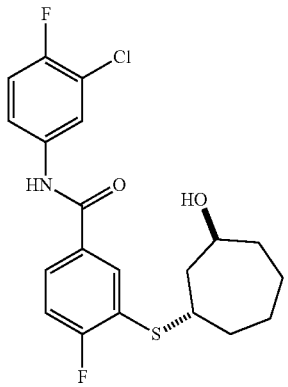

Prepared in an analogous manner to Example 14B but using instead Intermediate A. LC-MS: 412 (M+H)+.

Example 29: (±)-4-Fluoro-3-((4-hydroxypentyl)thio)-N-(3,4,5-trifluorophenyl)benzamide

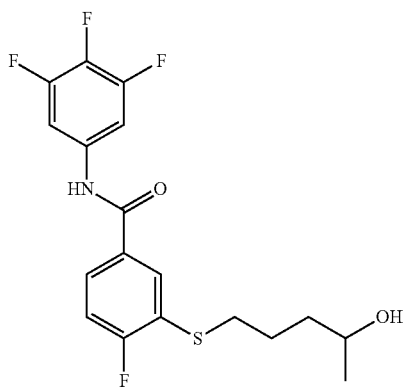 [SMILES: CC(O)CCCSc1cc(C(=O)Nc2cc(F)c(F)c(F)c2)ccc1F]

Prepared in an analogous manner to Example 18 but using instead Example 23 as the Intermediate. LC-MS: 388 (M+H)+.

Example 30: 4-Fluoro-3-((4-oxopentyl)thio)-N-(3,4,5-trifluorophenyl)benzamide

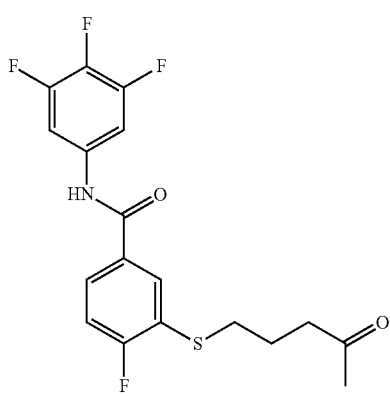 [SMILES: CC(=O)CCCSc1cc(C(=O)Nc2cc(F)c(F)c(F)c2)ccc1F]

Prepared in an analogous manner to Step 1 of Example 18 but using instead Example 29 as the starting material. LC-MS: 385 (M+H)+.

Example 31: 4-Fluoro-3-((4-hydroxy-4-methylpentyl)thio)-N-(3,4,5-trifluorophenyl)benzamide

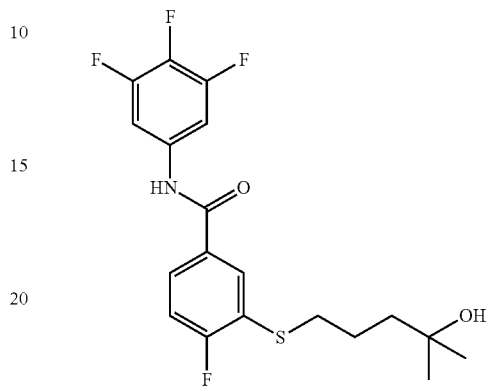

Prepared in an analogous manner to Step 1 of Example 19 but using instead Example 30 as the starting material. LC-MS: 402 (M+H)+.

Example 32: N-(3-Chloro-4-fluorophenyl)-4-fluoro-3-(((1-(2-hydroxyethyl)cyclopropyl)methyl)thio)benzamide

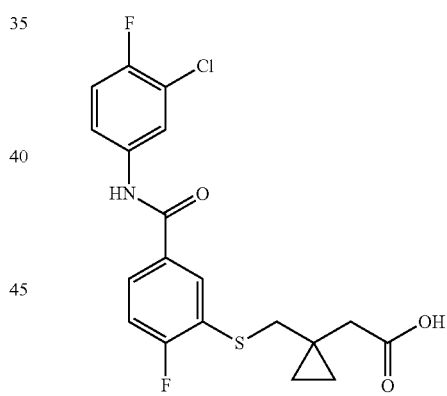

Step 1:

To a THF (5 mL) solution of 2-(1-(((5-((3-chloro-4-fluorophenyl)carbamoyl)-2-fluorophenyl)thio)methyl)cyclopropyl)acetic acid (prepared in an analogous route to that for Example 1 using intermediate A; 177 mg, 0.428 mmol) cooled to 0° C. was added triethylamine (0.115 mL, 0.642 mmol) and ethyl chloroformate (0.050 mL, 0.514 mmol) and the resulting solution was allowed to warm to RT over a period of 13 h. MeOH (2 mL) and NaBH4 (97 mg, 2.57 mmol) were added to the reaction mixture and stirred at RT for 6 h. Reaction mixture was washed with 1N HCl and extracted with EtOAc. The combined organic phases were then washed further with water and brine, then dried over Na2SO4, filtered and the filtrate concentrated in vacuo. Purification of the crude product thus obtained by way of column chromatography (SiO2, 0-50% EtOAc/Hexanes) afforded the ester (163 mg, 87% yield).

Step 2:

To a THF (5 mL) solution of the ester (17 mg, 0.038 mmol), LiBH$_4$ (9 mg, 0.38 mmol) was added and resulting solution stirred at RT for 2 h. Reaction mixture was washed with 1N HCl and extracted with EtOAc. The Combined organics were then washed further with water and brine, then dried over Na$_2$SO$_4$, filtered and the filtrate concentrated in vacuo. Purification of the crude product thus obtained by way of column chromatography (SiO$_2$, 0-50% EtOAc/hexanes) to afford the title compound (10 mg, 67% yield). LC-MS: 400 (M+H)$^+$.

Example 33: 4-Fluoro-3-(((1-(2-hydroxyethyl)cyclopropyl)methyl)thio)-N-(3,4,5-trifluorophenyl)benzamide

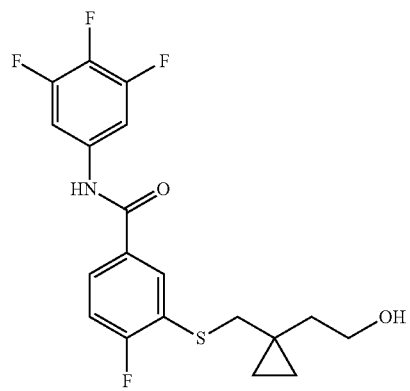 [SMILES: O=C(Nc1cc(F)c(F)c(F)c1)c1ccc(F)c(SCC2(CCO)CC2)c1]

Prepared in an analogous manner to Example 32 but using instead Intermediate C. LC-MS: 400 (M+H)$^+$.

Example 34: (cis/trans)-N-(3-Chloro-4-fluorophenyl)-3-((4-hydroxycyclohexyl)thio)benzamide

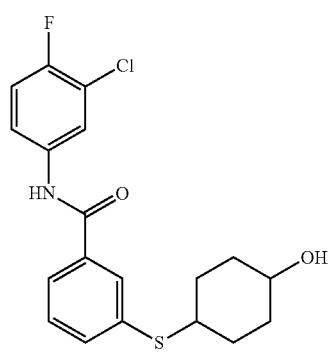 [SMILES: O=C(Nc1ccc(F)c(Cl)c1)c1cccc(SC2CCC(O)CC2)c1]

Prepared in an analogous manner to Example 10 but using instead Intermediate F. LC-MS: 380 (M+H)$^+$.

Example 35: N-(3-Chloro-4-fluorophenyl)-3-(cyclohexylthio)benzamide

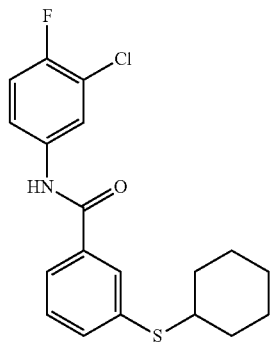 [SMILES: O=C(Nc1ccc(F)c(Cl)c1)c1cccc(SC2CCCCC2)c1]

Prepared in an analogous manner to Example 2 but using instead Intermediate F. LC-MS: 364 (M+H)$^+$.

Example 36: N-(3-Chloro-4-fluorophenyl)-3-((2-hydroxyl)thio)benzamide

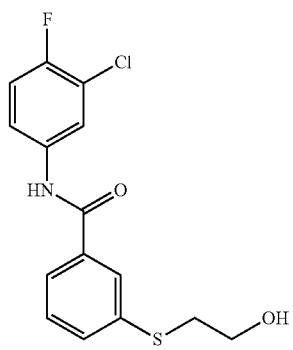 [SMILES: O=C(Nc1ccc(F)c(Cl)c1)c1cccc(SCCO)c1]

Prepared in an analogous manner to Example 7 but using instead Intermediate F. LC-MS: 326 (M+H)$^+$.

Example 37: N-(3-Chloro-4-fluorophenyl)-3-(cyclopentylthio)benzamide

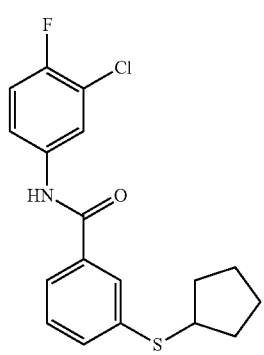 [SMILES: O=C(Nc1ccc(F)c(Cl)c1)c1cccc(SC2CCCC2)c1]

Prepared in an analogous manner to Example 3 but using instead Intermediate F. LC-MS: 350 (M+H)$^+$.

Example 38: (±)-N-(3-Chloro-4-fluorophenyl)-3-((3-oxocycloheptyl)thio)benzamide

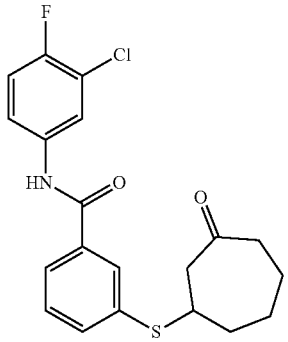 [SMILES: O=C1CCCCC(Sc2cccc(C(=O)Nc3ccc(F)c(Cl)c3)c2)C1]

Prepared in an analogous manner to Example 12 but using instead Intermediate F. LC-MS: 392 (M+H)+.

Example 39A: (±)-N-(3-Chloro-4-fluorophenyl)-3-(((1S,3R)-3-hydroxycycloheptyl)thio)benzamide

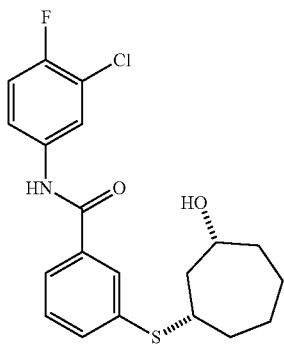

Prepared in an analogous manner to Example 14A but using instead Intermediate F. LC-MS: 394 (M+H)+.

Example 39B: (±)-N-(3-Chloro-4-fluorophenyl)-3-(((1R,3R)-3-hydroxycycloheptyl)thio)benzamide

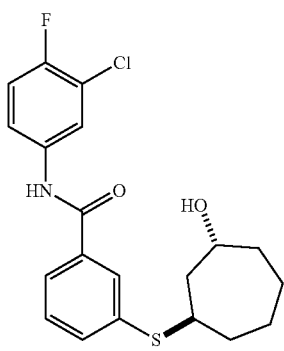

Prepared in an analogous manner to Example 14B but using instead Intermediate F. LC-MS: 394 (M+H)+.

Example 40: N-(3-Chloro-4-fluorophenyl)-3-((3-hydroxypropyl)thio)benzamide

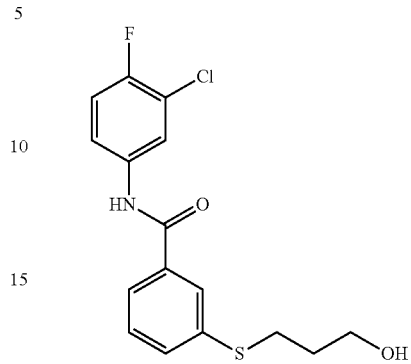

Prepared in an analogous manner to Example 17 but using instead Intermediate F. LC-MS: 340 (M+H)+.

Example 41: 3-((2-Aminoethyl)thio)-N-(3-chloro-4-fluorophenyl)-4-fluorobenzamide

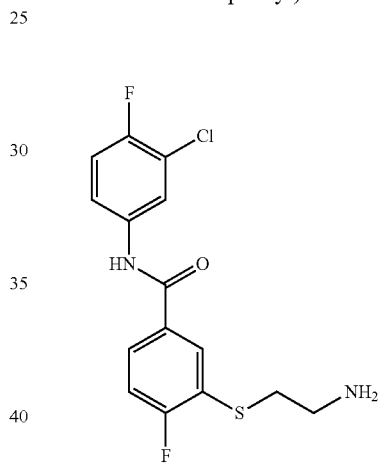

Prepared in an analogous manner to Example 26 but using instead 2-aminoethanethiol. LC-MS: 343 (M+H)+.

Example 42: N-(3-Chloro-4-fluorophenyl)-4-fluoro-3-((3,3,3-trifluoropropyl)thio)benzamide

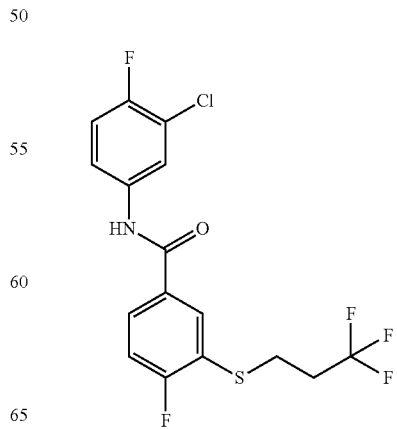

Prepared in an analogous manner to Example 26 but using instead 3,3,3-trifluoropropylmercaptan. LC-MS: 396 (M+H)+.

Example 43: N-(3-Chloro-4-fluorophenyl)-3-((cyclohexylmethyl)thio)benzamide

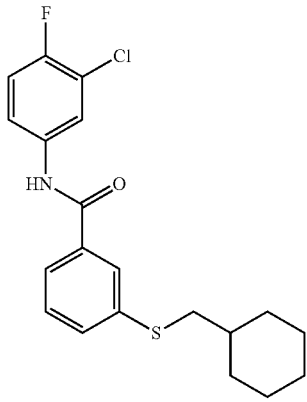 [SMILES: O=C(Nc1ccc(F)c(Cl)c1)c1cccc(SCC2CCCCC2)c1]

Prepared in an analogous manner to Example 35 but using instead cyclohexanemethanethiol. LC-MS: 378 (M+H)+.

Example 44: N-(3-Chloro-4-fluorophenyl)-3-((2-morpholinoethyl)thio)benzamide

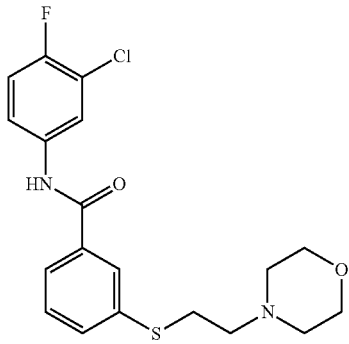 [SMILES: O=C(Nc1ccc(F)c(Cl)c1)c1cccc(SCCN2CCOCC2)c1]

Prepared in an analogous manner to Example 35 but using instead 2-morpholin-4-ylethanethiol. LC-MS: 395 (M+H)+.

Example 45: (±)-N-(3-Chloro-4-fluorophenyl)-4-fluoro-3-(((tetrahydrofuran-2-yl)methyl)thio)benzamide

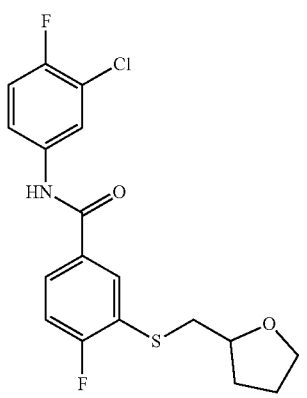 [SMILES: O=C(Nc1ccc(F)c(Cl)c1)c1ccc(F)c(SCC2CCCO2)c1]

To a DMSO/glycol (4 mL/0.1 mL) solution of Intermediate A (116 mg, 0.295 mmol) was added cesium carbonate (144 mg, 0.442 mmol) and the solution was vigorously de-oxygenated via sub-surface purging with nitrogen for 15 min. [1,1'-Bis(diphenylphosphino)ferrocene]dichloropalladium (21 mg, 0.0295 mmol), 1,1'-Bis(diphenylphosphino)ferrocene (8 mg, 0.0147 mmol), sodium thiosulfate (116 mg, 0.737 mmol) and tetrahydrofurfuryl chloride (0.479 mL, 4.43 mmol) were then added and the reaction vessel was sealed and heated at 120° C. for 13 h. After cooling to RT, the reaction mixture was diluted with ether and washed with sat. NH4Cl, water and brine. The organic extracts were then dried over Na2SO4, filtered and the filtrate concentrated in vacuo. The crude product thus obtained was then purified by preparative HPLC to afford the title compound (16 mg, 14% yield). LC-MS: 384 (M+H)+.

Example 46: (±)-N-(3-Chloro-4-fluorophenyl)-4-fluoro-3-(((tetrahydrofuran-3-yl)methyl)thio)benzamide

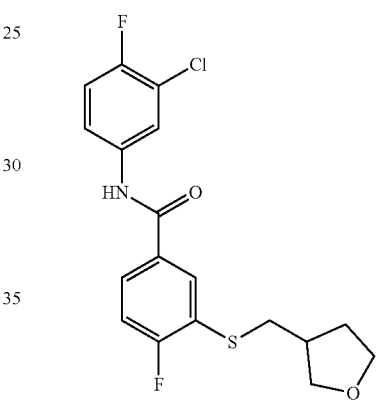

Prepared in an analogous manner to Example 45 but using instead 3-(chloromethyl)tetrahydrofuran. LC-MS: 384 (M+H)+.

Example 47: N-(3-Chloro-4-fluorophenyl)-4-fluoro-3-(((tetrahydro-2H-pyran-4-yl)methyl)thio)benzamide

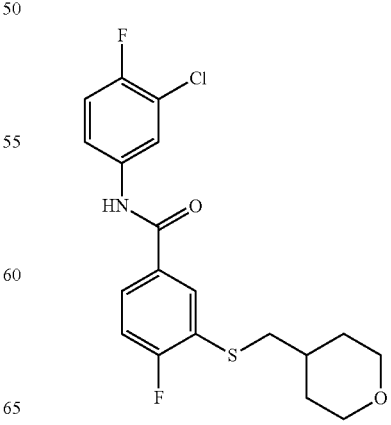

Prepared in an analogous manner to Example 45 but using instead 4-(chloromethyl)tetrahydropyran. LC-MS: 398 (M+H)+.

Example 48: 5-(Cyclopentylthio)-6-oxo-N-(3,4,5-trifluorophenyl)-1,6-dihydropyridine-3-carboxamide

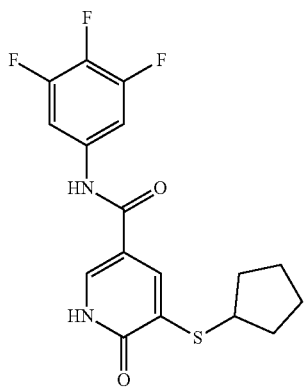 [SMILES: O=C(Nc1cc(F)c(F)c(F)c1)c1c[nH]c(=O)c(SC2CCCC2)c1]

Step 1:

A stirred suspension of 5-bromo-6-oxo-1,6-dihydropyridine-3-carboxylic acid (992 mg, 4.55 mmol) and pyridine (1 mL) in DCM (10 mL) was cooled to 0° C., treated with thionyl chloride (0.397 mL, 5.46 mmol), warmed to RT and stirred for 30 min. The reaction mixture was again cooled to 0° C. and treated with a solution of 3,4,5-trifluoroaniline (709 mg, 5.00 mmol), TEA (2.2 mL, 16 mmol) and DMAP (12 mg, 0.46 mmol) in DCM (5 mL) before stirring at RT for 18 h. The reaction mixture was diluted with EtOAc, washed with sat. NaHCO$_3$, 1N HCl and brine. The organic extract was then dried over MgSO$_4$, filtered and the filtrate concentrated in vacuo. Purification by way of column chromatography (SiO$_2$, 0-100% EtOAc/Hexanes) afforded 5-bromo-6-oxo-N-(3,4,5-trifluorophenyl)-1,6-dihydropyridine-3-carboxamide (1.18 g, 75% yield).

Step 2:

Tris(dibenzylideneacetone)dipalladium(0) (32 mg, 0.035 mmol), xantphos (40 mg, 0.070 mmol) and cyclopentanethiol (0.082 mL, 0.768 mmol) were added to a dioxane (5 mL) solution of 5-bromo-6-oxo-N-(3,4,5-trifluorophenyl)-1,6-dihydropyridine-3-carboxamide (242 mg, 0.698 mmol) and diisopropylethylamine (0.182 mL, 1.05 mmol). The solution was vigorously de-oxygenated via sub-surface purging with nitrogen for 15 min and the reaction vessel was then sealed and heated at 100° C. for 15 h. After cooling to RT, the reaction mixture was diluted with EtOAc and washed with 1N HCl, sat. NaHCO$_3$ and brine. The organic extract was then dried over MgSO$_4$, filtered and the filtrate concentrated in vacuo. Purification by way of column chromatography (SiO$_2$, 0-100% EtOAc/Hexanes) afforded the title compound. (165 mg, 64% yield) LC-MS: 369 (M+H)+.

Example 49: 2-(1-(((5-((3-Chloro-4-fluorophenyl)carbamoyl)-2-fluorophenyl)thio)methyl)cyclopropyl)acetic Acid

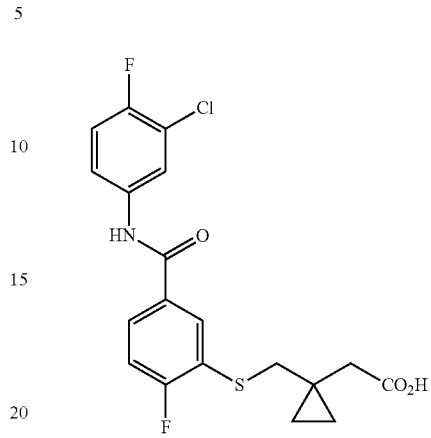

Prepared in an analogous manner to Example 1 but using instead Intermediate A. LC-MS: 412 (M+H)+.

Example 50: Ethyl 2-((5-((3-chloro-4-fluorophenyl)carbamoyl)-2-fluorophenyl)thio)-2-methylpropanoate

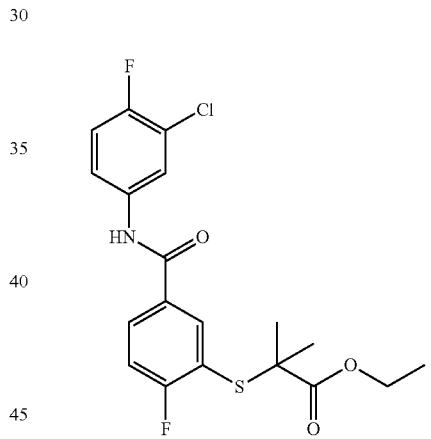

Step 1:

To an acetone (10 mL) solution of Example 13, step 1 (100 mg, 0.58 mmol), was added potassium carbonate (120 mg, 0.87 mmol) and ethyl 2-bromo-2-methylpropanoate (0.100 mL, 0.7 mmol) and the resulting solution heated to 60° C. for 13 h. The volatiles were removed in vacuo and the resulting residue was partitioned between ether and 10% aq. HCl. The combined organics were then washed further with water and brine then dried over Na$_2$SO$_4$, filtered and the filtrate concentrated in vacuo. No further purification was necessary.

Step 2:

To a DMF (15 mL) solution of the isolated benzoic acid (166 mg, 0.58 mmol), was added diisopropylamine (2 mL, 11.3 mmol) and 3-chloro-4-fluoroaniline (93 mg, 0.64 mmol). The mixture was stirred at RT for 1 hour before HATU (243 mg, 0.64 mmol) was added.

The resulting solution was stirred at RT overnight. The reaction mixture was quenched with water and extracted with EtOAc and the combined organics were washed further

Example 51: 2-((5-((3-Chloro-4-fluorophenyl)carbamoyl)-2-fluorophenyl)thio)-2-methylpropanoic Acid

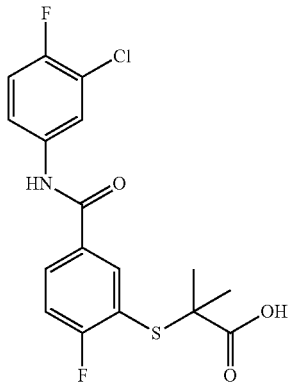 [SMILES: CC(C)(Sc1cc(C(=O)Nc2ccc(F)c(Cl)c2)ccc1F)C(=O)O]

To a THF/MeOH (3 mL/3 mL) solution of Example 50 (84 mg, 0.20 mmol) was added 2N LiOH (0.300 mL, 0.6 mmol). The resulting mixture was stirred at RT for 13 h after which was diluted with EtOAc and washed sequentially with 1N HCl, water and brine and the volatiles removed in vacuo. The resulting mixture was subjected to purification by way of column chromatography (SiO$_2$, 0-50% acetone/hexanes to afford a white foam (60 mg, 85% yield). LC-MS: 386 (M+H)$^+$.

Example 52: N-(3-Chloro-4-fluorophenyl)-3-(cycloheptylthio)-4-fluorobenzamide

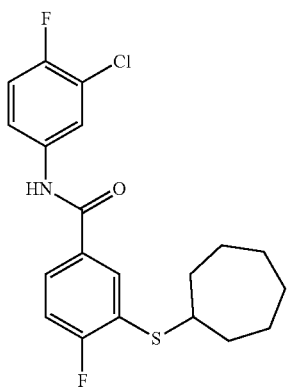 [SMILES: O=C(Nc1ccc(F)c(Cl)c1)c1ccc(F)c(SC2CCCCCC2)c1]

Prepared in an analogous manner to Example 50 but using instead bromocycloheptane in step 1. LC-MS: 396 (M+H)$^+$.

Example 53: (±)-3-((5-((3-Chloro-4-fluorophenyl)carbamoyl)-2-fluorophenyl)thio)cyclopentanecarboxylic Acid

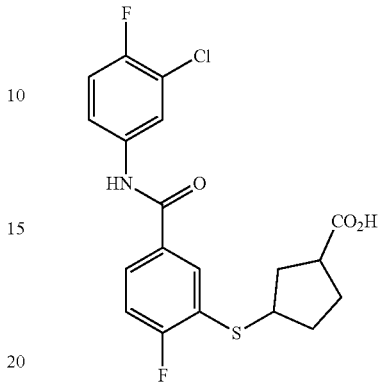

Step 1:
Prepared as in Example 14 but using methyl 3-oxocyclopentanecarboxylate as the starting material.

Step 2:
To a DCM (15 mL) solution of the alcohol (1.29 g, 8.9 mmol) was added triethylamine (1.8 mL, 13.0 mmol). The solution was cooled to 0° C. before methanesulfonyl chloride (0.93 mL, 12.0 mmol) was added dropwise. The resulting mixture was allowed to warm to RT over 13 h. The reaction was diluted with DCM and washed with water, the organic phase separated, dried (Na$_2$SO$_4$), filtered and the filtrate concentrated in vacuo. No further purification was necessary to afford methyl 3-((methyl sulfonyl)oxy)cyclopentanecarboxylate.

Step 3:
To a THF (8 mL) solution of 5-bromo-2-fluorobenzenethiol (336 mg, 1.6 mmol) under N$_2$ purge, NaH (65 mg, 1.6 mmol) was added at RT in one portion. After 45 min. this mixture was added to the mesylate as a solution in THF (3 mL) dropwise over 3 min. The resulting suspension was then sealed and heated at 50° C. for 4.5 h. After cooling to RT, the reaction mixture was diluted with ether and quenched with sat. NaHCO$_3$, and then washed further with water and brine. The organic extract was dried over Na$_2$SO$_4$, filtered and the filtrate concentrated in vacuo. Purification by way of column chromatography (SiO$_2$, 0-50% EtOAc/hexanes to afford methyl 3-((5-bromo-2-fluorophenyl)thio)cyclopentanecarboxylate as a colorless oil (310 mg, 88% yield).

Step 4:
Methyl 3-((5-bromo-2-fluorophenyl)thio)cyclopentanecarboxylate (103 mg, 0.309 mmol), sodium carbonate (49 mg, 0.464 mmol), palladium(II) acetate (2 mg, 0.0093 mmol) and xantphos (5 mg, 0.0093 mmol) were combined and the vessel was back filled with carbon monoxide by way of a balloon. 3-chloro-4-fluoroaniline (67 mg, 0.464 mmol) was then added as a toluene (5 mL) solution and reaction vessel was then sealed and heated at 80° C. for 13 h. After cooling to RT, the reaction mixture was diluted with ether and washed with water and brine. The organic extract was then dried over Na$_2$SO$_4$, filtered and the filtrate concentrated in vacuo. The crude product thus obtained was then purified by preparative HPLC to afford methyl 3-((5-((3-chloro-4-fluorophenyl)carbamoyl)-2-fluorophenyl)thio)cyclopentanecarboxylate (12 mg, 10% yield).

Step 5:

To a THF/MeOH (3 mL/3 mL) solution of the aforementioned ester (12 mg, 0.0281 mmol) was added 2N LiOH (2 mL). The resulting mixture was stirred at RT for 13 h after which was diluted with EtOAc and washed sequentially with 1N HCl, water and brine and the volatiles removed in vacuo. The resulting mixture was subjected to purification by way of preparative HPLC to afford the title compound as a white solid (6.5 mg, 60% yield). LC-MS: 412 (M+H)+.

Example 54: (±)-3-((2-Fluoro-5-((3,4,5-trifluorophenyl)carbamoyl)phenyl)thio)cyclopentanecarboxylic Acid

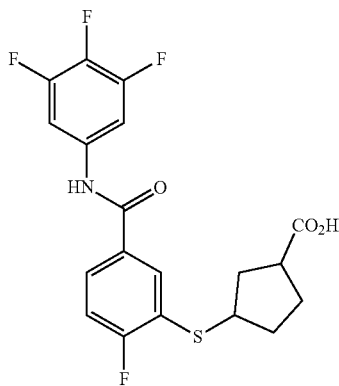 [SMILES: O=C(Nc1cc(F)c(F)c(F)c1)c1ccc(F)c(SC2CCC(C(=O)O)C2)c1]

Prepared in an analogous manner to Example 53 but using instead 3,4,5-trifluoroaniline in step 4. LC-MS: 414 (M+H)+.

Example 55: (±)-3-((5-((3,4-Difluorophenyl)carbamoyl)-2-fluorophenyl)thio)cyclopentanecarboxylic Acid

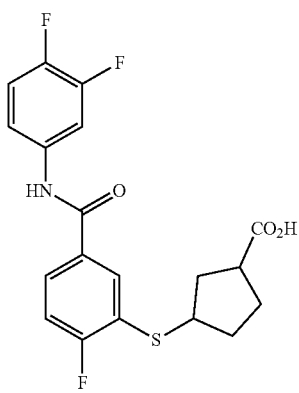 [SMILES: O=C(Nc1ccc(F)c(F)c1)c1ccc(F)c(SC2CCC(C(=O)O)C2)c1]

Prepared in an analogous manner to Example 53 but using instead 3,4,-difluoroaniline in step 4. LC-MS: 396 (M+H)+.

Example 56: 1-((5-((3-Chloro-4-fluorophenyl)carbamoyl)-2-fluorophenyl)thio)cyclobutanecarboxylic Acid

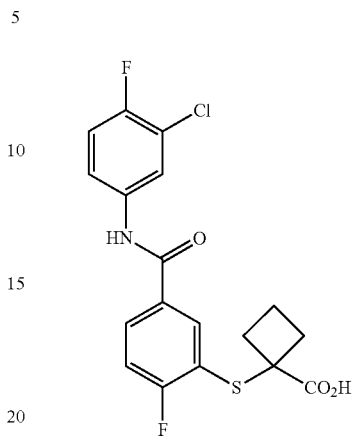

Step 1:

To a DMSO (2.5 mL) solution of 5-bromo-2-fluorobenzenethiol (207 mg, 1.0 mmol) was added ethyl 1-bromocyclobutanecarboxylate (0.240 mL, 1.5 mmol) and cesium carbonate (490 mg, 1.5 mmol). The resulting suspension was then sealed and heated at 100° C. for 72 h. After cooling to RT, the reaction mixture was diluted with ether and washed sequentially with water and brine. The organic extract was then dried over $Na_2SO_4$, filtered and the filtrate concentrated in vacuo. Purification by way of column chromatography ($SiO_2$, 0-50% EtOAc/Hexanes) afforded ethyl 1-((5-((3-chloro-4-fluorophenyl)carbamoyl)-2-fluorophenyl)thio)cyclobutanecarboxylateas as a pale yellow liquid (308 mg, 92% yield).

Step 2:

Ethyl 1-((5-bromo-2-fluorophenyl)thio)cyclobutanecarboxylate (150 mg, 0.450 mmol), sodium carbonate (71 mg, 0.675 mmol), palladium(II) acetate (30 mg, 0.135 mmol) and xantphos (78 mg, 0.135 mmol) were combined and the vessel was back filled with a carbon monoxide via balloon. 3-chloro-4-fluoroaniline (98 mg, 0.675 mmol) was then added as a toluene (5 mL) solution and reaction vessel was then sealed and heated at 80° C. for 13 h. After cooling to RT, the reaction mixture was diluted with ether and washed with water and brine. The organic extract was then dried over $Na_2SO_4$, filtered and the filtrate concentrated in vacuo. The crude product thus obtained was then purified by preparative HPLC to afford ethyl 1-((5-((3-chloro-4-fluorophenyl)carbamoyl)-2-fluorophenyl)thio)cyclobutanecarboxylate (60 mg, 31% yield).

Step 3:

To a THF/MeOH (3 mL/3 mL) solution of the ester (60 mg, 0.141 mmol) was added 2N LiOH (2 mL). The resulting mixture was stirred at RT for 13 h after which was diluted with EtOAc and washed sequentially with 1N HCl, water and brine and the volatiles removed in vacuo. The resulting mixture was subjected to purification by way of preparative HPLC to afford the title compound as a white solid (35 mg, 64% yield). LC-MS: 398 (M+H)+.

Example 57: 1-((5-((3,4-Difluorophenyl)carbamoyl)-2-fluorophenyl)thio)cyclobutanecarboxylic Acid

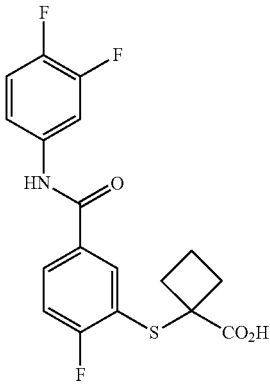 [SMILES: O=C(Nc1ccc(F)c(F)c1)c1ccc(F)c(SC2(C(=O)O)CCC2)c1]

Prepared in an analogous manner to Example 56 but using 3,4-difluoroaniline in step 2. LC-MS: 382 (M+H)$^+$.

Example 58: (cis/trans)-3-((5-((3-Chloro-4-fluorophenyl)carbamoyl)-2-fluorophenyl)thio)cyclobutanecarboxylic Acid

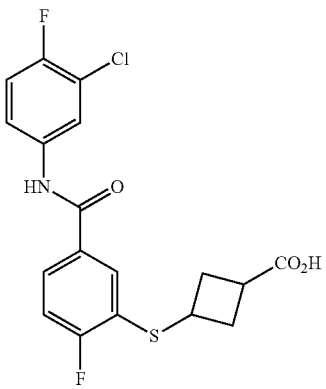 [SMILES: O=C(Nc1ccc(F)c(Cl)c1)c1ccc(F)c(SC2CC(C(=O)O)C2)c1]

Step 1:

To a DMSO (3 mL) solution of 5-bromo-2-fluorobenzenethiol (250 mg, 1.2 mmol) was added methyl 3-chlorocyclobutanecarboxylate (270 mg, 1.8 mmol), cesium carbonate (490 mg, 1.5 mmol) and sodium iodide (18 mg, 0.12 mmol). The resulting suspension was then sealed and heated at 100° C. for 16 h. After cooling to RT, the reaction mixture was diluted with ether and washed sequentially with water and brine. The organic extract was then dried over Na$_2$SO$_4$, filtered and the filtrate concentrated in vacuo. Purification by way of column chromatography (SiO$_2$, 0-50% EtOAc/Hexanes) afforded methyl 3-((5-bromo-2-fluorophenyl)thio)cyclobutanecarboxylate as a pale yellow liquid (160 mg, 42% yield).

Step 2:

Methyl 3-((5-bromo-2-fluorophenyl)thio)cyclobutanecarboxylate (85 mg, 0.266 mmol), sodium carbonate (42 mg, 0.399 mmol), palladium(II) acetate (12 mg, 0.053 mmol) and xantphos (31 mg, 0.053 mmol) were combined and the vessel back filled with carbon monoxide via a balloon. 3-chloro-4-fluoroaniline (58 mg, 0.399 mmol) was then added as a toluene (5 mL) solution and reaction vessel was then sealed and heated at 80° C. for 13 h. After cooling to RT, the reaction mixture was diluted with ether and washed with water and brine. The organic extract was then dried over Na$_2$SO$_4$, filtered and the filtrate concentrated in vacuo. The crude product thus obtained was then purified by preparative HPLC to afford ethyl 3-((5-((3-chloro-4-fluorophenyl)carbamoyl)-2-fluorophenyl)thio)cyclobutanecarboxylate (90 mg, 82% yield).

Step 3:

To a THF/MeOH (3 mL/3 mL) solution of the ester (90 mg, 0.218 mmol) was added 2N LiOH (2 mL). The resulting mixture was stirred at RT for 13 h after which was diluted with EtOAc and washed sequentially with 1N HCl, water and brine and the volatiles removed in vacuo. The resulting mixture was subjected to purification by way of preparative HPLC to afford the title compound as a white solid (8 mg, 93% yield). LC-MS: 398 (M+H)$^+$.

Example 59: (cis/trans)-3-((5-((3,4-Difluorophenyl)carbamoyl)-2-fluorophenyl)thio)cyclobutanecarboxylic Acid

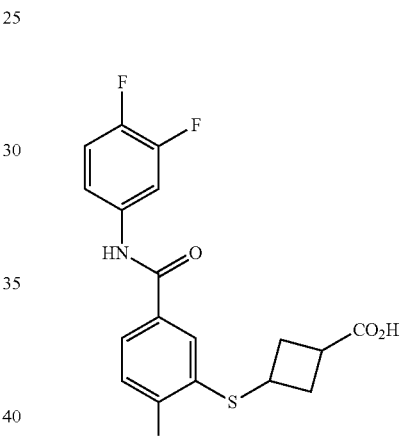

Prepared in an analogous manner to Example 59 but using 3,4-difluoroaniline in step 2. LC-MS: 382 (M+H)$^+$.

Example 60: N-(3-Chloro-4-fluorophenyl)-4-fluoro-3-((oxetan-3-ylmethyl)thio)benzamide

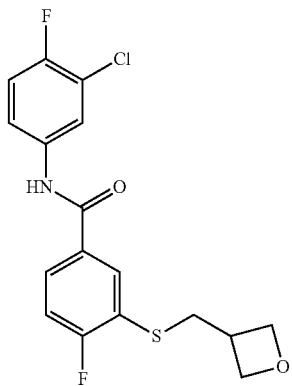 [SMILES: O=C(Nc1ccc(F)c(Cl)c1)c1ccc(F)c(SCC2COC2)c1]

Prepared in an analogous manner to Example 50 but using 3-(chloromethyl)oxetane in step 1. LC-MS: 370 (M+H)+.

Example 61: (cis/trans)-4-((5-((3-Chloro-4-fluorophenyl)carbamoyl)-2-fluorophenyl)thio)cyclohexanecarboxylic Acid

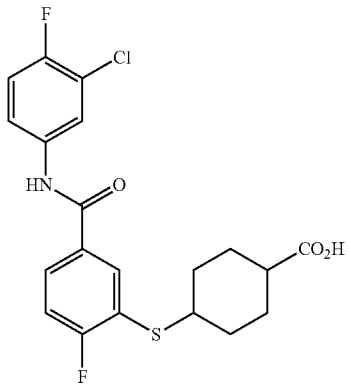 [SMILES: O=C(Nc1ccc(F)c(Cl)c1)c1ccc(F)c(SC2CCC(C(=O)O)CC2)c1]

Step 1:
To a MeOH (40 mL) solution of methyl 4-oxocyclohexanecarboxylate (5 g, 32 mmol) cooled to 0° C. was added NaBH₄ (1.2 g, 32 mmol). The resulting mixture was allowed to warm to RT for 13 h. The reaction mixture was quenched with 1N HCl and extracted with EtOAc twice. The combined organics were then washed further with brine, dried over Na₂SO₄, filtered and the filtrate concentrated in vacuo. Purification by way of column chromatography (SiO₂, 0-50% EtOAc/hexanes) afforded methyl 4-hydroxycyclohexanecarboxylate as a colorless oil (3.78 g, 75% yield).

Step 2:
To a DCM (45 mL) solution of the alcohol (3.78 g, 24 mmol) was added triethylamine (4.9 mL, 35 mmol). The solution was cooled to 0° C. before methanesulfonyl chloride (2.5 mL, 32 mmol) was added dropwise. The resulting mixture was allowed to warm to RT over 13 h, diluted with DCM and washed with water. The organic phases were separated, dried over Na₂SO₄, filtered and the filtrate concentrated in vacuo. No further purification was necessary to afford methyl 4-((methyl sulfonyl)oxy)cyclohexanecarboxylate.

Step 3:
To a DMSO (15 mL) solution of 5-bromo-2-fluorobenzenethiol (3.70 mL, 3.0 mmol), was added methyl 4-((methylsulfonyl)oxy)cyclohexanecarboxylate (1.06 g, 4.5 mmol) and cesium carbonate (1.47 g, 4.5 mmol). The resulting suspension was then sealed and heated at 100° C. for 72 h. After cooling to RT, the reaction mixture was diluted with ether and washed sequentially with water and brine. The organic extract was then dried over Na₂SO₄, filtered and the filtrate concentrated in vacuo. Purification by way of column chromatography (SiO₂, 0-50% EtOAc/hexanes) afforded methyl 4-((5-bromo-2-fluorophenyl)thio)cyclohexanecarboxylate as a pale yellow oil (746 mg, 72% yield).

Step 4:
Methyl 4-((5-bromo-2-fluorophenyl)thio)cyclohexanecarboxylate (250 mg, 0.720 mmol), sodium carbonate (106 mg, 1.0 mmol), palladium(II) acetate (32 mg, 0.144 mmol) and xantphos (83 mg, 0.144 mmol) were combined and the vessel was purged with carbon monoxide via balloon. 3-chloro-4-fluoroaniline (145 mg, 1.0 mmol) was then added as a toluene (5 mL) solution and reaction vessel was then sealed and heated at 80° C. for 13 h under an atmosphere of carbon monoxide. After cooling to RT, the reaction mixture was diluted with ether and washed with water and brine. The organic extract was then dried over Na₂SO₄, filtered and the filtrate concentrated in vacuo. The crude product thus obtained was then purified by preparative HPLC to afford methyl 4-((5-((3-chloro-4-fluorophenyl)carbamoyl)-2-fluorophenyl)thio)cyclohexanecarboxylate (200 mg, 64% yield).

Step 5:
To a THF/MeOH (3 mL/3 mL) solution of the ester (200 mg, 0.455 mmol) to this was added 2N LiOH (2 mL). The resulting mixture was stirred at RT for 13 h after which was diluted with EtOAc and washed sequentially with 1N HCl, water and brine and the volatiles removed in vacuo. The resulting mixture was subjected to purification by way of preparative HPLC to afford the title compound (100 mg, 52% yield). LC-MS: 426 (M+H)+.

Example 62: (cis/trans)-4-((2-Fluoro-5-((3,4,5-trifluorophenyl)carbamoyl)phenyl)thio)cyclohexanecarboxylic Acid

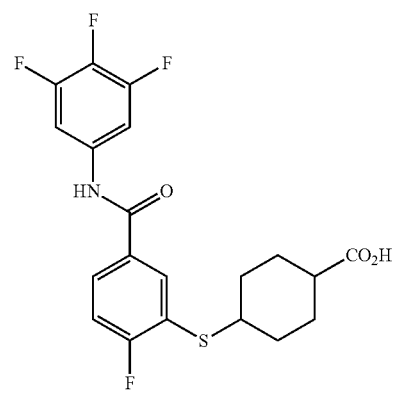 [SMILES: O=C(Nc1cc(F)c(F)c(F)c1)c1ccc(F)c(SC2CCC(C(=O)O)CC2)c1]

Prepared in an analogous manner to Example 61 but using 3,4,5-trifluoroaniline in step 4. LC-MS: 428 (M+H)+.

Example 63: (cis/trans)-4-((5-((3,4-Difluorophenyl)carbamoyl)-2-fluorophenyl)thio)cyclohexanecarboxylic Acid

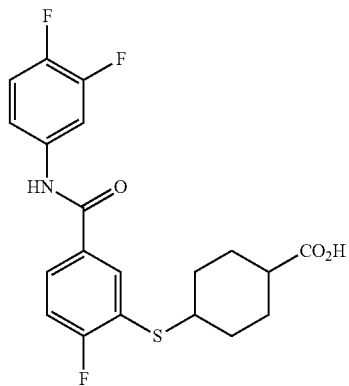 [SMILES: O=C(Nc1ccc(F)c(F)c1)c1ccc(F)c(SC2CCC(C(=O)O)CC2)c1]

Prepared in an analogous manner to Example 61 but using 3,4,-difluoroaniline in step 4. LC-MS: 410 (M+H)+.

Example 64: (±)-N-(3-Chloro-4-fluorophenyl)-4-fluoro-3-((tetrahydro-2H-pyran-3-yl)thio)benzamide

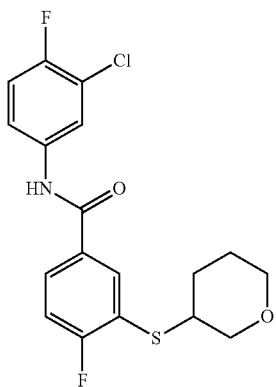 [SMILES: O=C(Nc1ccc(F)c(Cl)c1)c1ccc(F)c(SC2CCCOC2)c1]

Step 1:
To a DMSO (15 mL) solution of 5-bromo-2-fluorobenzenethiol (335 mg, 1.62 mmol) was added 3-bromotetrahydro-2H-pyran (400 mg, 2.43 mmol) and cesium carbonate (790 mg, 2.43 mmol). The resulting suspension was then sealed and heated at 100° C. for 16 h. After cooling to RT, the reaction mixture was diluted with ether and washed sequentially with water and brine. The organic extract was then dried over $Na_2SO_4$, filtered and the filtrate concentrated in vacuo. Purification by way of column chromatography ($SiO_2$, 0-30% EtOAc/Hexanes) afforded 3-((5-bromo-2-fluorophenyl)thio)tetrahydro-2H-pyran as a colorless oil (292 mg, 62% yield).

Step 2:
3-((5-bromo-2-fluorophenyl)thio)tetrahydro-2H-pyran (165 mg, 0.567 mmol), sodium carbonate (90 mg, 0.850 mmol), palladium(II) acetate (25 mg, 0.113 mmol) and xantphos (65 mg, 0.113 mmol) were combined and the vessel was back filled with carbon monoxide via balloon. 3-chloro-4-fluoroaniline (123 mg, 0.850 mmol) was then added as a toluene (5 mL) solution and reaction vessel was then sealed and heated at 80° C. for 13 h under a CO atmosphere. After cooling to RT, the reaction mixture was diluted with ether and washed with water and brine. The organic extract was then dried over $Na_2SO_4$, filtered and the filtrate concentrated in vacuo. The crude product thus obtained was then purified by preparative HPLC to afford the title compound (100 mg, 46% yield). LC-MS: 384 (M+H)+.

Example 65: N-(3-Chloro-4-fluorophenyl)-4-fluoro-3-(oxetan-3-ylthio)benzamide

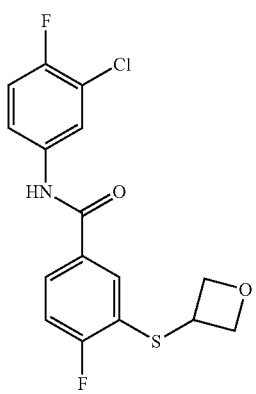 [SMILES: O=C(Nc1ccc(F)c(Cl)c1)c1ccc(F)c(SC2COC2)c1]

Prepared in an analogous manner to Example 64 but using 3-bromooxetane in step 2. LC-MS: 356 (M+H)+.

Example 66: (±)-N-(3-Chloro-4-fluorophenyl)-4-fluoro-3-((tetrahydrofuran-3-yl)thio)benzamide

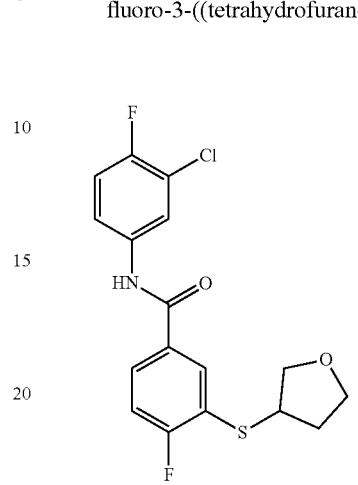

Prepared in an analogous manner to Example 64 but using 3-bromotetrahydrofuran in step 2. LC-MS: 370 (M+H)+.

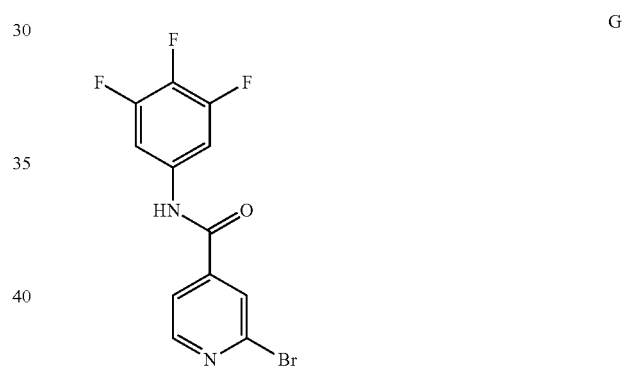

Intermediate G (2-Bromo-N-(3,4,5-trifluorophenyl)isonicotinamide)

To an anhydrous DMF solution (150 mL) of 4-bromo-isonicotinic acid (8.0 g, 39.6 mmol) and 2,3,4-trifluoroaniline (6.1 g, 7.52 mmol) under nitrogen atmosphere was added sequentially HATU (18.0 g, 47.5 mmol), diisopropylethylamine (21.0 mL, 120 mmol), and a catalytic amount of DMAP (488 mg, 4 mmol). The resulting solution was stirred at RT overnight. The reaction mixture was quenched with 0.5 N HCl aqueous solution and extracted with EtOAc. The combined organics were washed further with water and sat. $NaHCO_3$ solution, water and brine, dried over anhydrous $MgSO_4$, filtered and the filtrate concentrated in vacuo. The residue was triturated in DCM (40 mL) for 15 minutes and filtered. The filter cake was washed with DCM (10 mL) and dried under vacuum. Purification by way of column chromatography ($SiO_2$, 0-50% EtOAc/hexanes) afforded an off-white solid (6.96 g, 50% yield). LC-MS: 332 (M+H)+.

Example 67: (cis/trans)-2-((4-Hydroxycyclohexyl)thio)-N-(3,4,5-trifluorophenyl)isonicotinamide

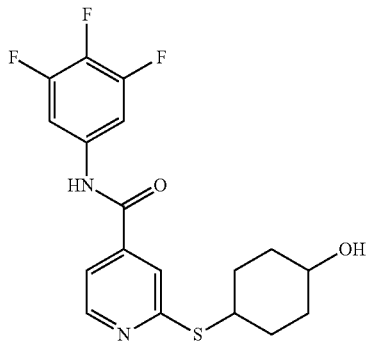 [SMILES: O=C(Nc1cc(F)c(F)c(F)c1)c1ccnc(SC2CCC(O)CC2)c1]

To a 1,4-dioxane (3 mL) solution of Intermediate G (2-bromo-N-(3,4,5-trifluorophenyl)isonicotinamide) (53.0 mg, 0.15 mmol) and 4-mercaptocyclohexanol (0.02 ml, 0.16 mmole) was added sequentially tris(dibenzylideneacetone)dipalladium(0) (7.0 mg, 0.008 mmol), xantphos (5.0 mg, 0.008 mmol) and diisopropylamine (0.052 mL, 0.30 mmol). The resulting solution was de-oxygenated via sub-surface purging with nitrogen for 5 min., and the reaction vessel was sealed afterward and heated at 100° C. for 16 hrs. After cooling to RT, the reaction mixture was diluted with ether, washed sequentially with 1N HCl, water and brine. The organic extract was then dried over $Na_2SO_4$, filtered and the filtrate concentrated in vacuo. Purification of the crude product thus obtained by way of column chromatography ($SiO_2$, 0-100% EtOAc/Hexanes) afforded desired product (43.8 mg, 76% yield). LC-MS: 383 $(M+H)^+$.

Intermediate H ((3-Iodo-4-methyl-N-(3-chloro-4-fluorophenyl)benzamide)

Prepared in an analogous manner to intermediate G, but using the 3-chloro-4-fluoroaniline and 3-iodo-4-methylbenzoic acid. LC-MS: 390 $(M+H)^+$.

Intermediate I ((3-Iodo-4-methyl-N-(3,4-difluorophenyl)benzamide)

Prepared in an analogous manner to intermediate G, but using the 3,4-difluoroaniline and 3-iodo-4-methylbenzoic acid. LC-MS: 374 $(M+H)^+$.

Intermediate J ((3-Iodo-4-methyl-N-(3,4,5-trifluorophenyl)benzamide)

Prepared in an analogous manner to intermediate G, but using the 3,4-5-trifluoroaniline and 3-iodo-4-methylbenzoic acid. LC-MS: 392 $(M+H)^+$.

Intermediate K ((3-Bromo-4-methoxy-N-(3-chloro-4-fluorophenyl)benzamide)

Prepared in an analogous manner to intermediate G, but using the 3-chloro-4-fluoroaniline and 3-bromo-4-methoxybenzoic acid. LC-MS: 359 $(M+H)^+$.

Intermediate L ((3-Bromo-4-methoxy-N-(3,4-difluorophenyl)benzamide)

Prepared in an analogous manner to intermediate G, but using the 3,4-difluoroaniline and 3-bromo-4-methoxybenzoic acid. LC-MS: 343 $(M+H)^+$.

Intermediate M ((3-Bromo-4-methoxy-N-(3,4,5-trifluorophenyl)benzamide)

Prepared in an analogous manner to intermediate G, but using the 3,4-5-trifluoroaniline and 3-bromo-4-methoxybenzoic acid. LC-MS: 361 $(M+H)^+$.

Intermediate N ((3-Iodo-4-chloro-N-(3-chloro-4-fluorophenyl)benzamide)

Prepared in an analogous manner to intermediate G, but using the 3-chloro-4-fluoroaniline and 4-chloro-3-iodobenzoic acid. LC-MS: 411 $(M+H)^+$.

Intermediate O ((3-Iodo-4-chloro-N-(3,4-difluorophenyl)benzamide)

Prepared in an analogous manner to intermediate G, but using the 3,4-difluoroaniline and 4-chloro-3-iodobenzoic acid. LC-MS: 394 $(M+H)^+$.

Intermediate P ((3-Iodo-4-chloro-N-(3,4,5-trifluorophenyl)benzamide)

Prepared in an analogous manner to intermediate G, but using the 3,4-5-trifluoroaniline and 4-chloro-3-iodobenzoic acid. LC-MS: 412 $(M+H)^+$.

Intermediate Q ((3-Bromo-4-trifluoromethyl-N-(3-chloro-4-fluorophenyl)benzamide)

Prepared in an analogous manner to intermediate G, but using the 3-chloro-4-fluoroaniline and 3-bromo-4-trifluoromethylbenzoic acid. LC-MS: 397 $(M+H)^+$.

Intermediate R ((3-Bromo-4-trifluoromethyl-N-(3,4-difluorophenyl)benzamide)

Prepared in an analogous manner to intermediate G, but using the 3,4-difluoroaniline 3-bromo-4-trifluoromethylbenzoic acid. LC-MS: 381 (M+H)$^+$.

Intermediate S ((3-Bromo-4-trifluoromethyl-N-(3,4,5-trifluorophenyl)benzamide)

Prepared in an analogous manner to intermediate G, but using the 3,4-5-trifluoroaniline and 3-bromo-4-trifluoromethylbenzoic acid. LC-MS: 399 (M+H)$^+$.

Intermediate T ((3-Bromo-4-cyano-N-(3-chloro-4-fluorophenyl)benzamide)

Prepared in an analogous manner to intermediate G, but using the 3-chloro-4-fluoroaniline and 3-bromo-4-cyanobenzoic acid. LC-MS: 355 (M+H)$^+$.

Intermediate U ((3-Bromo-4-cyano-N-(3,4-difluorophenyl)benzamide)

Prepared in an analogous manner to intermediate G, but using the 3,4-difluoroaniline 3-bromo-4-cyanobenzoic acid. LC-MS: 338 (M+H)$^+$.

Intermediate V ((3-Bromo-4-cyano-N-(3,4,5-trifluorophenyl)benzamide)

Prepared in an analogous manner to intermediate G, but using the 3,4-5-trifluoroaniline and 3-bromo-4-cyanobenzoic acid. LC-MS: 356 (M+H)$^+$.

Example 68: N-(3-Chloro-4-fluorophenyl)-3-(cyclohexylthio)-4-methylbenzamide

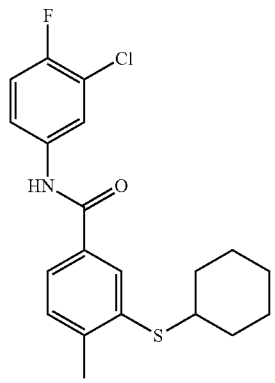 [SMILES: Cc1ccc(C(=O)Nc2ccc(F)c(Cl)c2)cc1SC1CCCCC1]

Prepared in an analogous manner to Example 67, but using intermediate H and cyclohexanethiol. LC-MS: 377 (M−H)$^−$.

Example 69: N-(3-Chloro-4-fluorophenyl)-3-(cyclohexylthio)-4-methoxybenzamide

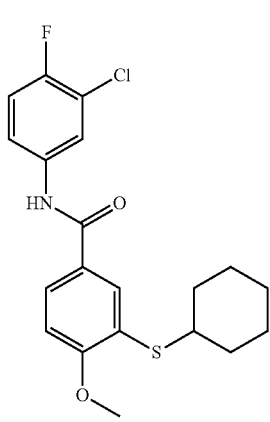 [SMILES: COc1ccc(C(=O)Nc2ccc(F)c(Cl)c2)cc1SC1CCCCC1]

Prepared in an analogous manner to Example 67, but using intermediate K and cyclohexanethiol. LC-MS: 394 (M+H)$^+$.

Example 70: (cis/trans)-N-(3-Chloro-4-fluorophenyl)-3-((4-hydroxycyclohexyl)thio)-4-methoxybenzamide

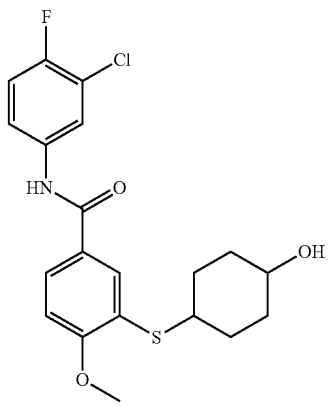 [SMILES: COc1ccc(C(=O)Nc2ccc(F)c(Cl)c2)cc1SC1CCC(O)CC1]

Prepared in an analogous manner to Example 67, but using intermediate K and 4-hydroxycyclohexanethiol. LC-MS: 410 (M+H)$^+$.

Example 71: 4-Chloro-N-(3-chloro-4-fluorophenyl)-3-(cyclohexylthio)benzamide

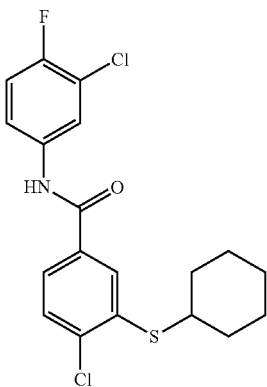

Prepared in an analogous manner to Example 67, but using intermediate N and cyclohexanethiol. LC-MS: 397 (M+H)$^+$.

Example 72: (±)-N-(3-Chloro-4-fluorophenyl)-4-fluoro-3-((2-fluorocyclohexyl)thio)benzamide

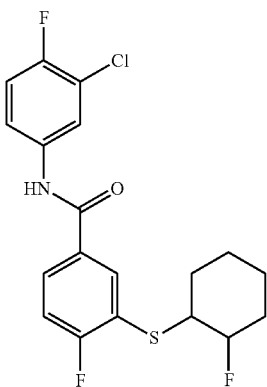 [SMILES: O=C(Nc1ccc(F)c(Cl)c1)c1ccc(F)c(SC2CCCCC2F)c1]

Prepared in an analogous manner to Example 64 but using 1-bromo-2-fluorocyclohexane in step 1. LC-MS: 400 (M+H)$^+$.

Example 73: N-(3-Chloro-4-fluorophenyl)-3-((4,4-dimethylcyclohexyl)thio)-4-fluorobenzamide

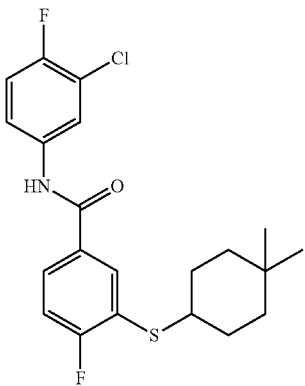 [SMILES: CC1(C)CCC(Sc2cc(C(=O)Nc3ccc(F)c(Cl)c3)ccc2F)CC1]

Step 1:
To a DCM (45 mL) solution of the 4,4-dimethylcyclohexanol (200 mg, 1.56 mmol) was added triethylamine (4.9 mL, 35 mmol). The solution was cooled to 0° C. before methanesulfonyl chloride (0.324 mL, 2.34 mmol) was added dropwise. The resulting mixture was allowed to warm to RT over 13 h. The reaction was diluted with DCM and washed with water, the organic phase dried (Na$_2$SO$_4$), filtered and the filtrate concentrated in vacuo. No further purification was necessary to afford 4,4-dimethylcyclohexyl methanesulfonate.

Step 2:
To a DMSO (15 mL) solution of 5-bromo-2-fluorobenzenethiol (130 mg, 0.62 mmol) was added 4,4-dimethylcyclohexyl methanesulfonate (190 mg, 0.94 mmol) and cesium carbonate (306 mg, 0.94 mmol). The resulting suspension was then sealed and heated at 100° C. for 72 h. After cooling to RT, the reaction mixture was diluted with ether and washed sequentially with water and brine. The organic extract was then dried over Na$_2$SO$_4$, filtered and the filtrate concentrated in vacuo. Purification by way of column chromatography (SiO$_2$, 0-100% EtOAc/Hexanes) afforded (5-bromo-2-fluorophenyl)(4,4-dimethylcyclohexyl)sulfane (131 mg, 67% yield).

Step 3:
(5-bromo-2-fluorophenyl)(4,4-dimethylcyclohexyl)sulfane (131 mg, 0.413 mmol), sodium carbonate (66 mg, 0.620 mmol), palladium(II) acetate (2 mg, 0.0083 mmol) and xantphos (5 mg, 0.0083 mmol) were added and the vessel was back filled with carbon monoxide via balloon. 3-chloro-4-fluoroaniline (90 mg, 0.620 mmol) was then added as a toluene (5 mL) solution and reaction vessel was then sealed and heated at 80° C. for 13 h under an atmosphere of carbon monoxide. After cooling to RT, the reaction mixture was diluted with ether and washed with water and brine. The organic extract was then dried over Na$_2$SO$_4$, filtered and the filtrate concentrated in vacuo. The crude product thus obtained was then purified by preparative HPLC to afford the title compound (55 mg, 33% yield). LC-MS: 410 (M+H)$^+$.

Example 74: (cis/trans)-N-(3-Chloro-4-fluorophenyl)-3-((4-hydroxycyclohexyl)thio)-4-methylbenzamide

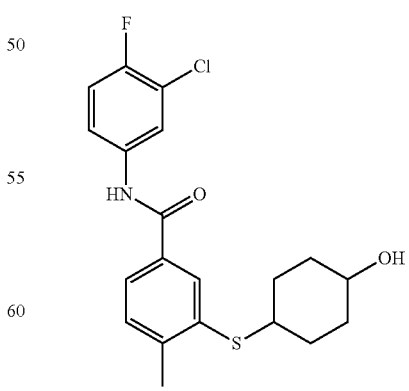

Prepared in an analogous manner to Example 67, but using intermediate H and 4-hydroxycyclohexanethiol. LC-MS: 394 (M+H)$^+$.

Example 75: (cis/trans)-4-Chloro-N-(3-chloro-4-fluorophenyl)-3-((4-hydroxycyclohexyl)thio)benzamide

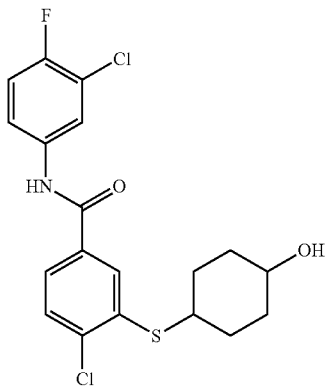

Prepared in an analogous manner to Example 67, but using intermediate N and 4-hydroxycyclohexanethiol. LC-MS: 415 (M+H)$^+$.

Example 76: 3-(Cyclohexylthio)-4-methyl-N-(3,4,5-trifluorophenyl)benzamide

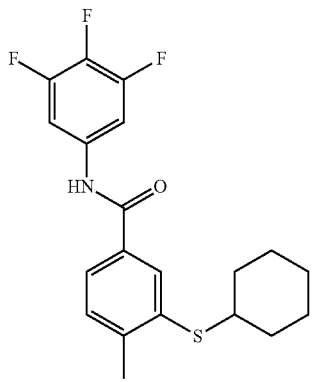 [SMILES: Cc1ccc(C(=O)Nc2cc(F)c(F)c(F)c2)cc1SC1CCCCC1]

Prepared in an analogous manner to Example 67, but using intermediate J and cyclohexanethiol. LC-MS: 380 (M+H)$^+$.

Example 77: (cis/trans)-3-((4-Hydroxycyclohexyl)thio)-4-methyl-N-(3,4,5-trifluorophenyl)benzamide

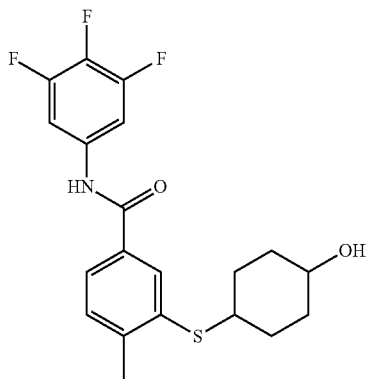 [SMILES: Cc1ccc(C(=O)Nc2cc(F)c(F)c(F)c2)cc1SC1CCC(O)CC1]

Prepared in an analogous manner to Example 67, but using intermediate J and 4-hydroxycyclohexanethiol. LC-MS: 396 (M+H)$^+$.

Example 78: 3-(Cyclohexylthio)-4-methoxy-N-(3,4,5-trifluorophenyl)benzamide

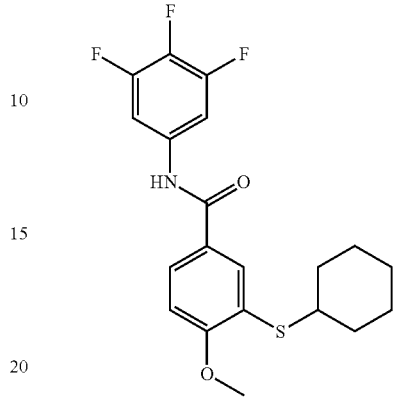

Prepared in an analogous manner to Example 67, but using intermediate M and cyclohexanethiol. LC-MS: 396 (M+H)$^+$.

Example 79: 4-Chloro-3-(cyclohexylthio)-N-(3,4,5-trifluorophenyl)benzamide

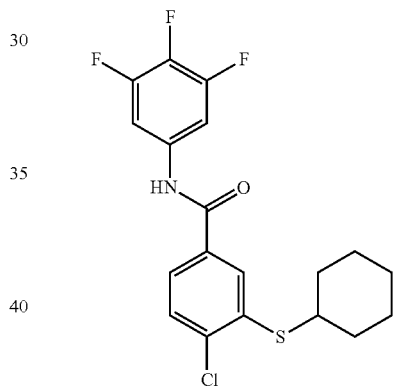

Prepared in an analogous manner to Example 67, but using intermediate P and cyclohexanethiol. LC-MS: 398 (M−H)$^-$.

Example 80: 3-(Cyclohexylthio)-N-(3,4-difluorophenyl)-4-methoxybenzamide

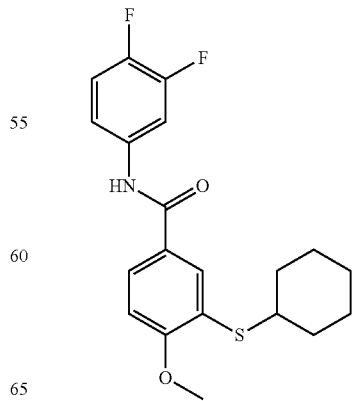

Prepared in an analogous manner to Example 67, but using intermediate L and cyclohexanethiol. LC-MS: 378 (M+H)+.

Example 81: (cis/trans)-4-Chloro-3-((4-hydroxycyclohexyl)thio)-N-(3,4,5-trifluorophenyl)benzamide

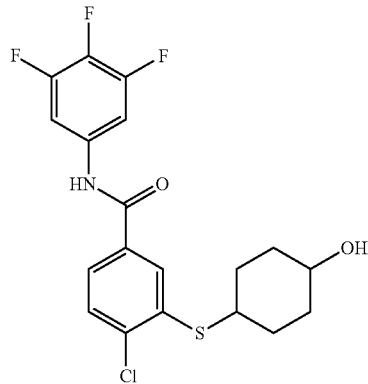

Prepared in an analogous manner to Example 67, but using intermediate P and 4-hydroxycyclohexanethiol. LC-MS: 414 (M−1).

Example 82: (±)-N-(3-Chloro-4-fluorophenyl)-3-((3,3-dimethylcyclohexyl)thio)-4-fluorobenzamide

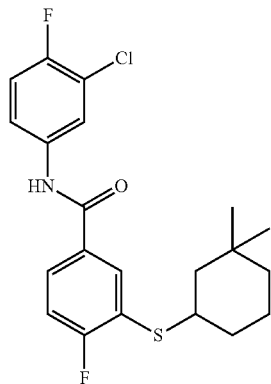 [SMILES: CC1(C)CCCC(Sc2cc(C(=O)Nc3ccc(F)c(Cl)c3)ccc2F)C1]

Step 1:
To a MeOH (40 mL) solution of 3,3-dimethylcyclohexanone (450 mg, 3.57 mmol) cooled to 0° C. was added NaBH$_4$ (200 m g, 5.35 mmol). The resulting mixture was allowed to warm to RT for 13 h. The reaction mixture was quenched with 1N HCl and extracted with EtOAc twice and the combined organics were then washed further with brine, dried over Na$_2$SO$_4$, filtered and the filtrate concentrated in vacuo. No further purification was necessary to afford 3,3-dimethylcyclohexanol as a colorless oil (450 mg, 98% yield).

Step 2:
To a DCM (45 mL) solution of the alcohol (450 mg, 3.51 mmol) was added triethylamine (0.730 mL, 35 mmol). The solution was cooled to 0° C. before methanesulfonyl chloride (0.460 mL, 5.27 mmol) was added dropwise. The resulting mixture was allowed to warm to RT over 13 h. The reaction was diluted with DCM and washed with water, the organic phases separated, dried (Na$_2$SO$_4$), filtered and the filtrate concentrated in vacuo. No further purification was necessary to afford 3,3-dimethylcyclohexyl methanesulfonate.

Step 3:
To a DMSO (15 mL) solution of 5-bromo-2-fluorobenzenethiol (150 mg, 0.72 mmol), 3,3-dimethylcyclohexyl methanesulfonate (227 mg, 1.08 mmol) and cesium carbonate (353 mg, 1.68 mmol) were added. The resulting suspension was then sealed and heated at 100° C. for 72 h. After cooling to RT, the reaction mixture was diluted with ether and washed sequentially with water and brine. The organic extract was then dried over Na$_2$SO$_4$, filtered and the filtrate concentrated in vacuo. Purification by way of column chromatography (SiO$_2$, 0-30% EtOAc/hexanes) afforded (5-bromo-2-fluorophenyl)(3,3-dimethylcyclohexyl)sulfane as a colorless oil (100 mg, 44% yield).

Step 4:
(5-Bromo-2-fluorophenyl)(3,3-dimethylcyclohexyl)sulfane (100 mg, 0.315 mmol), sodium carbonate (50 mg, 0.472 mmol), palladium(II) acetate (2 mg, 0.0063 mmol) and xantphos (4 mg, 0.0063 mmol) were combined and the vessel was back filled with carbon monoxide via balloon. 3-Chloro-4-fluoroaniline (68 mg, 0.472 mmol) was then added as a toluene (5 mL) solution and reaction vessel was then sealed and heated at 80° C. for 13 h under an atmosphere of carbon monoxide. After cooling to RT, the reaction mixture was diluted with ether and washed with water and brine. The organic extract was then dried over Na$_2$SO$_4$, filtered and the filtrate concentrated in vacuo. The crude product thus obtained was then purified by preparative HPLC to afford methyl 4-((5-((3-chloro-4-fluorophenyl)carbamoyl)-2-fluorophenyl)thio)cyclohexanecarboxylate (6.5 mg, 5% yield). LC-MS: 410 (M+H)+.

Example 83: N-(3-Chloro-4-fluorophenyl)-3-((4,4-difluorocyclohexyl)thio)-4-fluorobenzamide

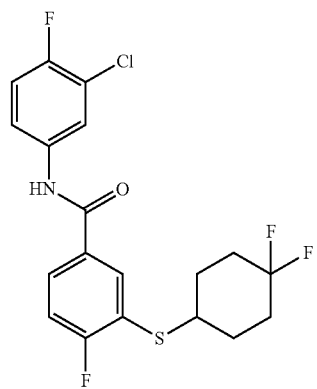 [SMILES: O=C(Nc1ccc(F)c(Cl)c1)c1ccc(F)c(SC2CCC(F)(F)CC2)c1]

Prepared in an analogous manner to Example 64 but using instead 4-bromo-1,1-difluorocyclohexane as the starting material in step 1. LC-MS: 418 (M+H)+.

Example 84: (cis/trans)-3-((4-Hydroxycyclohexyl)thio)-4-methoxy-N-(3,4,5-trifluorophenyl)benzamide

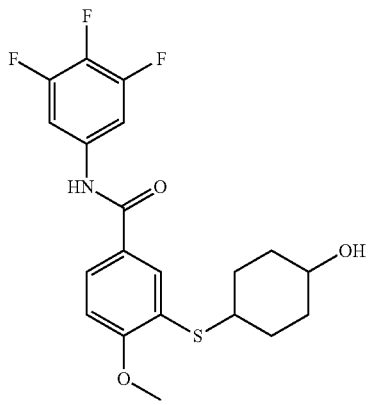 [SMILES: COc1ccc(C(=O)Nc2cc(F)c(F)c(F)c2)cc1SC1CCC(O)CC1]

Prepared in an analogous manner to Example 67, but using intermediate M and 4-hydroxycyclohexanethiol. LC-MS: 412 (M+H)⁺.

Example 85: 3-(Cyclohexylthio)-N-(3,4-difluorophenyl)-4-methylbenzamide

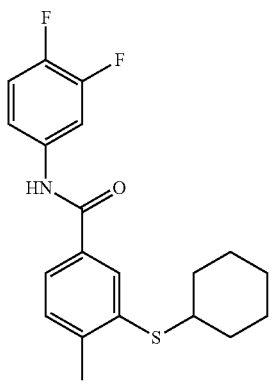

Prepared in an analogous manner to Example 67, but using intermediate I and cyclohexanethiol. LC-MS: 362 (M+H)⁺.

Example 86: 4-Chloro-3-(cyclohexylthio)-N-(3,4-difluorophenyl)benzamide

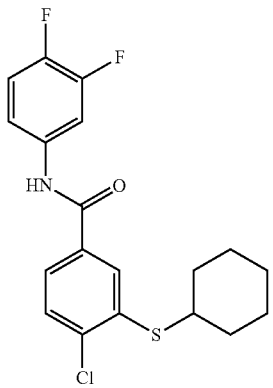

Prepared in an analogous manner to Example 67, but using intermediate O and cyclohexanethiol. LC-MS: 382 (M+H)⁺.

Example 87: (cis/trans)-4-Chloro-N-(3,4-difluorophenyl)-3-((4-hydroxycyclohexyl)thio)benzamide

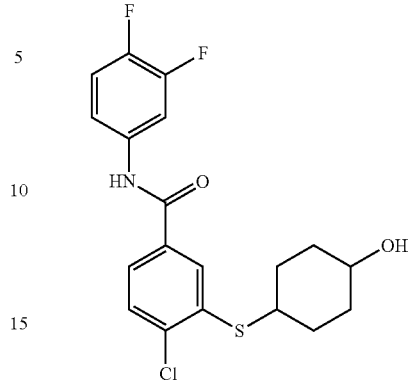

Prepared in an analogous manner to Example 67, but using intermediate O and 4-hydroxycyclohexanethiol. LC-MS: 398 (M+H)⁺.

Example 88: (cis/trans)-N-(3,4-Difluorophenyl)-3-((4-hydroxycyclohexyl)thio)-4-methylbenzamide

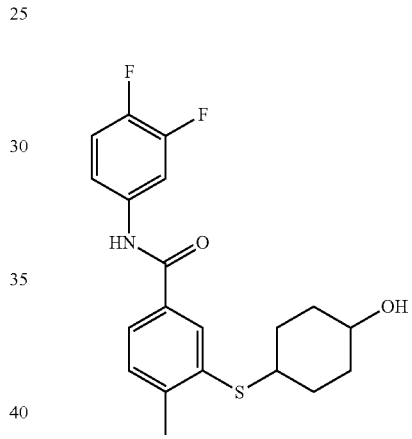

Prepared in an analogous manner to Example 67, but using intermediate I and 4-hydroxycyclohexanethiol. LC-MS: 378 (M+H)⁺.

Example 89: (cis/trans)-N-(3,4-Difluorophenyl)-3-((4-hydroxycyclohexyl)thio)-4-methoxybenzamide

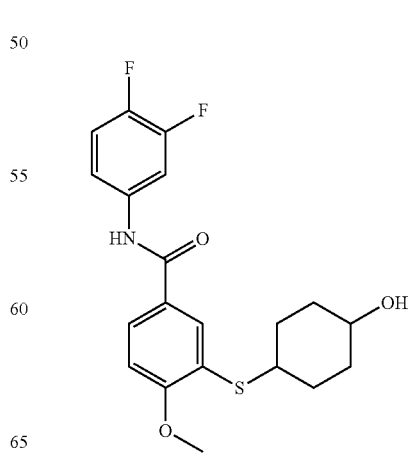

Prepared in an analogous manner to Example 67, but using intermediate L and 4-hydroxycyclohexanethiol. LC-MS: 394 (M+H)⁺.

Example 90: (cis/trans)-3-((4-Hydroxycyclohexyl)thio)-4-(trifluoromethyl)-N-(3,4,5-trifluorophenyl)benzamide

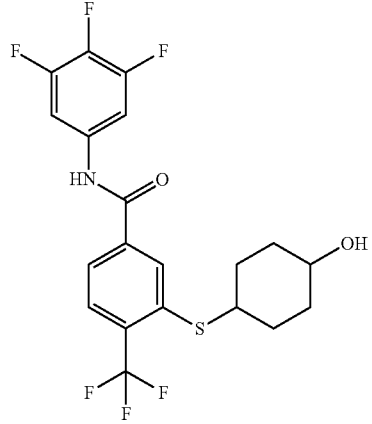 [SMILES: O=C(Nc1cc(F)c(F)c(F)c1)c1ccc(C(F)(F)F)c(SC2CCC(O)CC2)c1]

Prepared in an analogous manner to Example 67, but using intermediate S and 4-hydroxycyclohexanethiol. LC-MS: 448 (M−H)⁻.

Example 91: (cis/trans)-N-(3-Chloro-4-fluorophenyl)-3-((4-hydroxycyclohexyl)thio)-4-(trifluoromethyl)benzamide

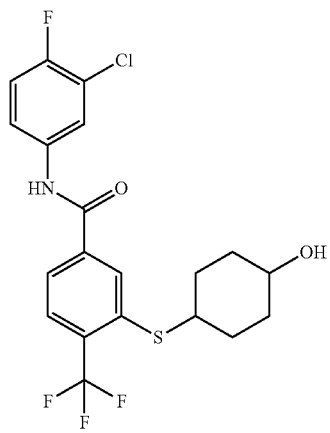 [SMILES: O=C(Nc1ccc(F)c(Cl)c1)c1ccc(C(F)(F)F)c(SC2CCC(O)CC2)c1]

Prepared in an analogous manner to Example 67, but using intermediate Q and 4-hydroxycyclohexanethiol. LC-MS: 446 (M−1).

Example 92: (cis/trans)-N-(3,4-Difluorophenyl)-4-hydroxy-3-((4-hydroxycyclohexyl)thio)benzamide

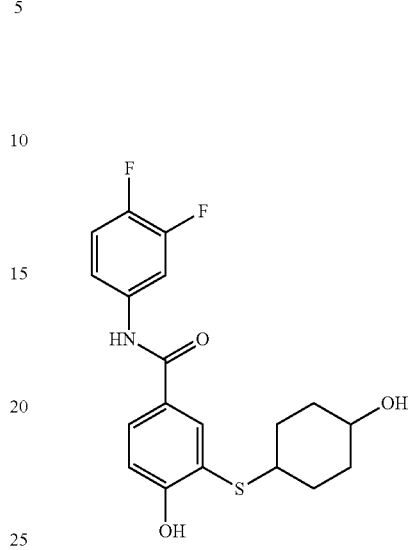

To the DCM solution (1 mL) of compound in Example 89 (10.0 mg, 0.025 mmol) was added a solution of boron tribromide (2M in DCM; 1.0 mL) at RT under nitrogen atmosphere dropwise. The reaction flask was sealed and stirred overnight at RT. Aqueous work up followed by purification of the crude residue by way of column chromatography (SiO$_2$, 0-100% EtOAc/hexanes afforded an off-white solid (4.2 mg, 44% yield). LC-MS: 380 (M+H)⁺.

Example 93: (cis/trans)-4-Cyano-N-(3,4-difluorophenyl)-3-((4-hydroxycyclohexyl)thio)benzamide

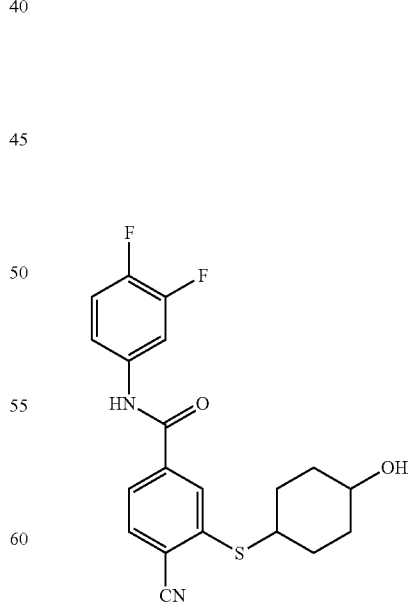

Prepared in an analogous manner to Example 67, but using intermediate U and 4-hydroxycyclohexanethiol. LC-MS: 389 (M+H)⁺.

Example 94: (cis/trans)-4-Cyano-3-((4-hydroxycyclohexyl)thio)-N-(3,4,5-trifluorophenyl)benzamide

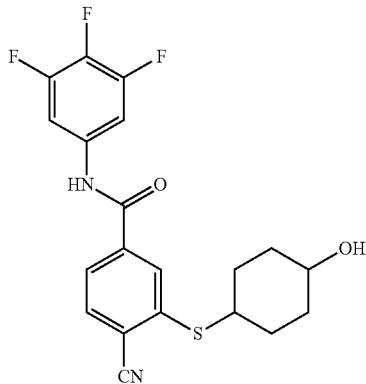

Prepared in an analogous manner to Example 67, but using intermediate V and 4-hydroxycyclohexanethiol. LC-MS: 405 (M−H)⁻.

Example 95: (cis/trans)-N-(3-Chloro-4-fluorophenyl)-4-cyano-3-((4-hydroxycyclohexyl)thio)benzamide

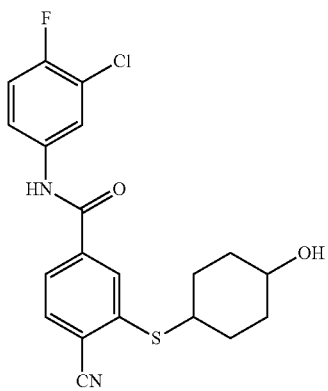 [SMILES: N#Cc1ccc(C(=O)Nc2ccc(F)c(Cl)c2)cc1SC1CCC(O)CC1]

Prepared in an analogous manner to Example 67, but using intermediate T and 4-hydroxycyclohexanethiol. LC-MS: 405 (M+H)⁺.

Example 96A: (1S,3R)-3-((5-((3-Chloro-4-fluorophenyl)carbamoyl)-2-fluorophenyl)thio)-1-ethylcyclobutanecarboxylic Acid

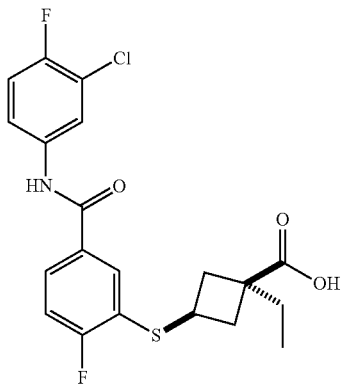

Step 1:
To a nitrogen flushed vessel containing NaH (82 mg, 3.4 mmol), THF (6 mL) was added followed by the dropwise addition of methyl 3-hydroxycyclobutanecarboxylate (0.360 mL, 3.4 mmol). The resulting suspension was allowed to stir at 0° C. for 35 min. and then at RT for 45 min. In a separate round bottom flask flushed with nitrogen, diisopropylamine (0.560 mL, 4 mmol) in THF (5 mL) was cooled to −78° C. before n-BuLi (2.0 M in hexanes, 2 mL, 4 mmol) was added dropwise over 5 min. The resulting solution was allowed to stir at −78° C. for 30 min. and then at 0° C. for 30 min. The LDA thus generated was then added dropwise to the sodium alkoxide suspension at −78° C. Finally, ethyl iodide (0.320 mL, 4 mmol) was added and stirred at 0° C. for 15 min and then at RT for 2.5 h. The crude mixture was quenched with sat. NH₄Cl and extracted in ether. The combined organics were then washed further with brine, dried over Na₂SO₄, filtered and the filtrate concentrated in vacuo. Purification by way of column chromatography (SiO₂, 0-50% EtOAc/hexanes) afforded methyl 1-ethyl-3-hydroxycyclobutanecarboxylate. (277 mg, 51% yield).

Step 2:
To a DCM (4 mL) solution of the alcohol (135 mg, 0.84 mmol) was added triethylamine (0.164 mL, 1.2 mmol). The solution was cooled to 0° C. before methanesulfonyl chloride (0.085 mL, 1.1 mmol) was added dropwise. The resulting mixture was allowed to warm to RT over 13 h. The reaction was diluted with DCM and washed with water, then dried over Na₂SO₄, filtered and the filtrate concentrated in vacuo. No further purification was necessary to afford methyl 1-ethyl-3-((methylsulfonyl)oxy)cyclobutanecarboxylate.

Step 3:
To a DMSO (5 mL) solution of 4-fluoro-3-mercaptobenzoic acid (80 mg, 0.45 mmol), methyl 1-ethyl-3-((methylsulfonyl)oxy)cyclobutanecarboxylate (146 mg, 0.54 mmol) and cesium carbonate (222 mg, 0.68 mmol) were added. The resulting suspension was then sealed and heated at 100° C. for 72 h. After cooling to RT, the reaction mixture was diluted with ether and washed sequentially with water and brine. The organic extract was then dried over Na₂SO₄, filtered and the filtrate concentrated in vacuo. Purification by way of column chromatography (SiO₂, 0-20% EtOAc/hexanes) afforded 3-((3-ethyl-3-(methoxycarbonyl)cyclobutyl)thio)-4-fluorobenzoic acid as a dark orange oil (44 mg, 31% yield).

Step 4:
To a DMF (5 mL) solution of the benzoic acid (44 mg, 0.141 mmol) was added diisopropylethylamine (0.038 mL, 0.211 mmol) and 3-chloro-4-fluoroaniline (21 mg, 0.141 mmol). The reaction mixture was stirred at RT for 1 hour before HATU (64 mg, 0.141 mmol) was added. The resulting solution was stirred at RT overnight. The reaction mixture was quenched with water and extracted with EtOAc. The combined organics were washed further with water and brine, dried over Na₂SO₄, filtered and the filtrate concentrated in vacuo. Purification by preparative HPLC afforded the separation of the 2 diastereoisomers.

Step 5:
To a THF/MeOH (3 mL/3 mL) solution of the ester (50 mg, 0.113 mmol) was added 2N LiOH (2 mL). The resulting mixture was stirred at RT for 13 h after which was diluted with EtOAc and washed sequentially with 1N HCl, water and brine and the volatiles removed in vacuo. The resulting mixture was subjected to purification by preparative HPLC to afford the title compound (25 mg, 52% yield). LC-MS: 426 (M+H)⁺.

Example 96B: (1R,3S)-3-((5-((3-Chloro-4-fluorophenyl)carbamoyl)-2-fluorophenyl)thio)-1-ethylcyclobutanecarboxylic Acid

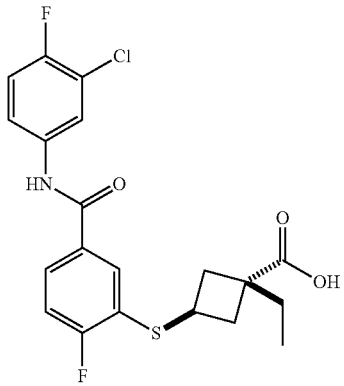

Prepared in an analogous manner to Example 96A. LC-MS: 426 (M+H)+.

Example 97: (±)-4-((5-((3-Chloro-4-fluorophenyl)carbamoyl)-2-fluorophenyl)thio)cycloheptanecarboxylic Acid

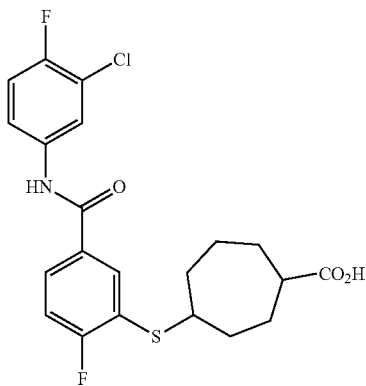 [SMILES: O=C(Nc1ccc(F)c(Cl)c1)c1ccc(F)c(SC2CCCC(C(=O)O)CC2)c1]

Prepared in an analogous manner to Example 82 but using instead methyl 4-oxocycloheptanecarboxylate as the starting material in step 1. LC-MS: 442 (M+H)+.

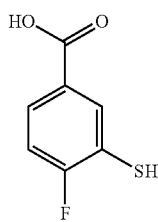

Intermediate W

4-Fluoro-3-mercaptobenzoic Acid

Concentrated HCl (120.0 mL) was added to a neat mixture of 3-chlorosulfonyl-4-fluorobenzoic acid (32.0 g, 134.0 mmol) and tin chloride di-hydrate (90.0 g, 400 mmol). The reaction solution was refluxed at 100° C. overnight, cooled to RT, diluted with distilled water (200 mL) and then basified to a pH of 10 using 1.0 N aqueous sodium hydroxide solution. The resulting solids were filtered off, and the filtrate was acidified to pH of 1 using a 1N HCl solution. A white solid was filtered off and washed with water and hexanes to afford the title compound (23.2 g, quantitative yield). LC-MS: 171 (M−H)−.

Example 98: (cis/trans)-3-((2-fluoro-5-((3,4,5-trifluorophenyl)carbamoyl)phenyl)thio)bicyclo[3.1.0]hexane-6-carboxylic Acid

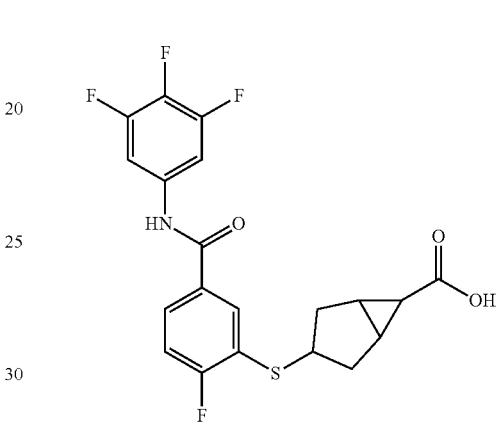

Step 1:

To a DMSO solution (6.0 mL) of intermediate W (172.0 mg, 1 mmol) and ethyl 3-((methylsulfonyl)oxy)bicyclo[3.1.0]hexane-6-carboxylate (248.3 mg, 1 mmol) was added anhydrous cesium carbonate (986.4 mg, 3 mmol) and the reaction solution was de-oxygenated via sub-surface purging with nitrogen for 5 minutes. The flask was sealed and heated at 60° C. for 4 hrs, cooled to RT and partitioned between 1N HCl and EtOAc. The combined organic phases were washed with water and brine, dried over anhydrous MgSO4, filtered and concentrated in vacuo to afford the crude adduct, 3-((6-(ethoxycarbonyl)bicyclo[3.1.0]hexan-3-yl)thio)-4-fluorobenzoic acid). LC-MS: 323 (M−H)−.

Step 2:

The HATU coupling of crude 3-((6-(ethoxycarbonyl)bicyclo[3.1.0]hexan-3-yl)thio)-4-fluorobenzoic acid and 3,4,5-trifluoroaniline, exemplified in previous examples afforded crude ethyl 3-((2-fluoro-5-((3,4,5-trifluorophenyl)carbamoyl)phenyl)thio)bicyclo[3.1.0]hexane-6-carboxylate). LC-MS: 452 (M−H)−.

Step 3:

To a THF/MeOH (15 mL/15 mL) solution of the crude ethyl 3-((2-fluoro-5-((3,4,5-trifluorophenyl)carbamoyl)phenyl)thio)bicyclo[3.1.0]hexane-6-carboxylate) was added 2N LiOH (10 mL). The resulting mixture was stirred at RT for 13 h after which was diluted with EtOAc and washed sequentially with 1N HCl, water and brine and the volatiles removed in vacuo. The resulting mixture was subjected to purification by preparative HPLC to afford the title compound as an off-white solid (106.4 mg, 25% overall yield over 3 steps). LC-MS: 424 (M−H)−.

Example 99: (cis/trans)-3-((2-Fluoro-5-((3,4,5-trifluorophenyl)carbamoyl)phenyl)thio)-N-(methylsulfonyl)bicyclo[3.1.0]hexane-6-carboxamide

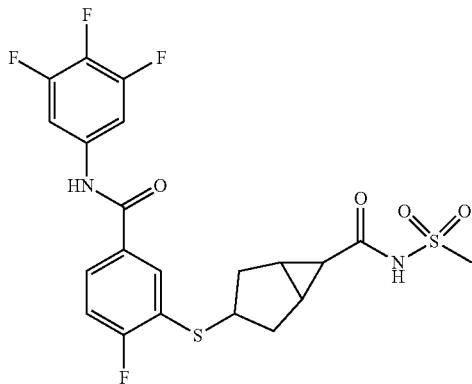 [SMILES: CS(=O)(=O)NC(=O)C1C2CC(Sc3cc(C(=O)Nc4cc(F)c(F)c(F)c4)ccc3F)CC21]

To a DCM solution (30 mL) of Example 98 (3-((2-fluoro-5-((3,4,5-trifluorophenyl)carbamoyl)phenyl)thio)bicyclo[3.1.0]hexane-6-carboxylic acid (555.0 mg, 1.30 mmol) was added successively DMAP (318.0 mg, 2.6 mmol), EDCI (404.0 mg, 2.6 mmol), and methanesulfonamide (247.0 mg 2.6 mmol) under $N_2$ atmosphere. The reaction flask was sealed and stirred at RT overnight. Concentration of the reaction mixture in vacuo and purification of the residue by preparative HPLC (30-100% acetonitrile in water containing 0.1% TFA) afforded the title compound as an off-white solid (136.0 mg, 21% yield). LC-MS: 501 (M–H)$^-$.

Example 100: 4-Fluoro-3-(((1S,4S)-4-((methylsulfonyl)carbamoyl)cyclohexyl)thio)-N-(3,4,5-trifluorophenyl)benzamide

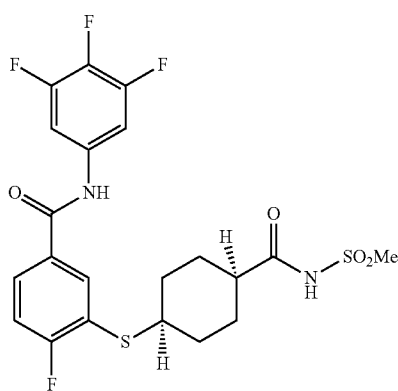 [SMILES: CS(=O)(=O)NC(=O)[C@H]1CC[C@@H](Sc2cc(C(=O)Nc3cc(F)c(F)c(F)c3)ccc2F)CC1]

Prepared in an analogous manner to Examples 98 and 99, but using trans-ethyl 4-((tosylsulfonyl)oxy)cyclohexanecarboxylate as the starting material to afford the title compound as an off-white solid. LC-MS: 503 (M–H)$^-$.

Example 101: (±)-2-(3-((2-Fluoro-5-((3,4,5-trifluorophenyl)carbamoyl)phenyl)thio)cyclopentyl)acetic Acid

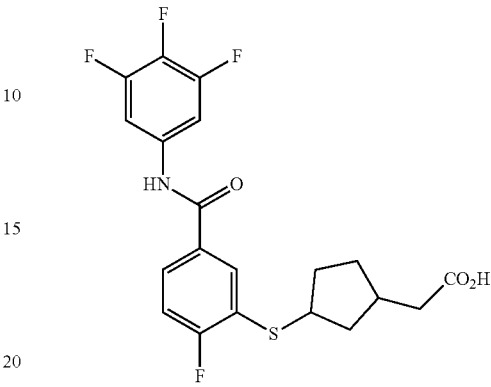

Step 1:
Prepared according to procedure described in House, H. O. et. al. *J. Org. Chem.* 1983, 48, 1643

Step 2:
To a MeOH (15 mL) solution of 2-oxabicyclo[3.2.1]octan-3-one, concentrated HCl (1 mL) was added and refluxed for 3 h. After cooling to RT, the reaction mixture was diluted with EtOAc and washed sequentially with water and brine, dried over $Na_2SO_4$, filtered and the filtrate concentrated in vacuo. No further purification was necessary to afford methyl 2-(3-hydroxycyclopentyl)acetate.

Step 3:
To a DCM (4 mL) solution of the alcohol (806 mg, 5.10 mmol) was added triethylamine (1.0 mL, 7.65 mmol). The solution was cooled to 0° C. before methanesulfonyl chloride (0.590 mL, 7.65 mmol) was added dropwise. The resulting mixture was allowed to warm to RT over 13 h. The reaction was diluted with DCM and washed with water, dried ($Na_2SO_4$), filtered and the filtrate concentrated in vacuo. No further purification was necessary to afford methyl 2-(3-((methylsulfonyl)oxy)cyclopentyl)acetate.

Step 4:
To a DMSO (5 mL) solution of 4-fluoro-3-mercaptobenzoic acid (150 mg, 0.872 mmol), methyl 2-(3-((methylsulfonyl)oxy)cyclopentyl)acetate (246 mg, 1.04 mmol) and cesium carbonate (425 mg, 1.31 mmol) and sodium iodide (cat.) were added. The resulting suspension was then sealed and heated at 80° C. for 16 h. After cooling to RT, the reaction mixture was diluted with ether and washed sequentially with water and brine. The organic extract was then dried over $Na_2SO_4$, filtered and the filtrate concentrated in vacuo. Purification by preparative HPLC afforded 4-fluoro-3-((3-(methoxycarbonyl)cyclopentyl)thio)benzoic acid as a white solid (52 mg, 20% yield).

Step 4:
To a DMF (5 mL) solution of 4-fluoro-3-((3-(methoxycarbonyl)cyclopentyl)thio)benzoic acid (52 mg, 0.166 mmol), diisopropylethylamine (0.045 mL, 0.249 mmol) and 3,4,5-trifluoroaniline (25 mg, 0.166 mmol). The mixture was stirred at RT for 1 hour before HATU (95 mg, 0.249 mmol) and DMAP (20 mg, 0.166 mmol) were added. The resulting solution was stirred at RT overnight, quenched with water and extracted with EtOAc. The combined organics were washed further with water and brine, dried over $Na_2SO_4$, filtered and the filtrate concentrated in vacuo. Purification by way of column chromatography (SiO$_2$, 0-100% EtOAc/hexanes) afforded methyl 3-((2-fluoro-5-((3,4,5-trifluorophenyl)carbamoyl)phenyl)thio)cyclopentanecarboxylate (22 mg, 73% yield).

Step 6:

To a THF/MeOH (3 mL/3 mL) solution of the ester (22 mg, 0.0498 mmol) to this was added 2N LiOH (2 mL). The resulting mixture was stirred at RT for 13 h after which was diluted with EtOAc and washed sequentially with 1N HCl, water and brine and the volatiles removed in vacuo. The resulting mixture was subjected to purification by way of preparative HPLC to afford the title compound (15 mg, 72% yield). LC-MS: 428 (M+H)$^+$.

Example 102: (±)-2-(3-((5-((3-Chloro-4-fluorophenyl)carbamoyl)-2-fluorophenyl)thio)cyclopentyl)acetic Acid

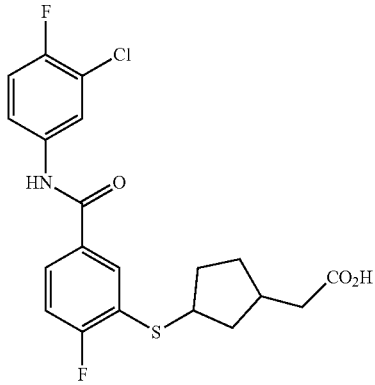

Prepared in an analogous manner to Example 102 but using instead 3-chloro-4-fluoroaniline in step 4. LC-MS: 426 (M+H)$^+$.

Example 103: (cis/trans)-3-((4-(Dimethylcarbamoyl)cyclohexyl)thio)-4-fluoro-N-(3,4,5-trifluorophenyl)benzamide

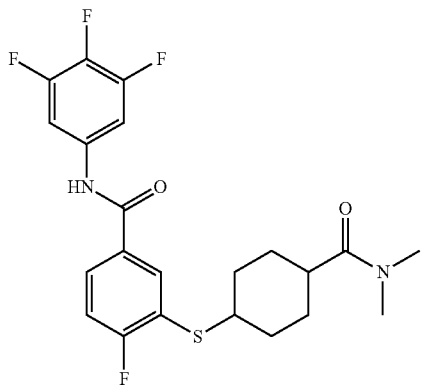 [SMILES: CN(C)C(=O)C1CCC(Sc2cc(C(=O)Nc3cc(F)c(F)c(F)c3)ccc2F)CC1]

To a DMF (5 mL) solution of Example 62 (35 mg, 0.082 mmol) was added diisopropylethylamine (0.022 mL, 0.123 mmol) and dimethylamine (0.041 mL, 0.082 mmol). The reaction mixture was stirred at RT for 1 hour before HATU (37 mg, 0.0984 mmol) was added. The resulting solution was stirred at RT for 13 h, quenched with water and extracted with EtOAc. The combined organics were washed further with water and brine, dried (Na$_2$SO$_4$), filtered and the filtrate concentrated in vacuo. Purification by preparative HPLC afforded the title compound (25 mg, 67% yield). LC-MS: 455 (M+H)$^+$.

Example 104: (cis/trans)-4-Fluoro-3-((4-(piperidine-1-carbonyl)cyclohexyl)thio)-N-(3,4,5-trifluorophenyl)benzamide

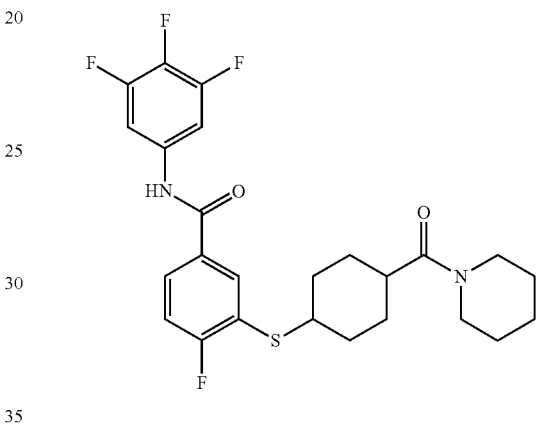

Prepared in an analogous manner to Example 103 but using piperidine. LC-MS: 495 (M+H)$^+$.

Example 105: (±)-2-(3-((5-((3,4-Difluorophenyl)carbamoyl)-2-fluorophenyl)thio)cyclopentyl)acetic Acid

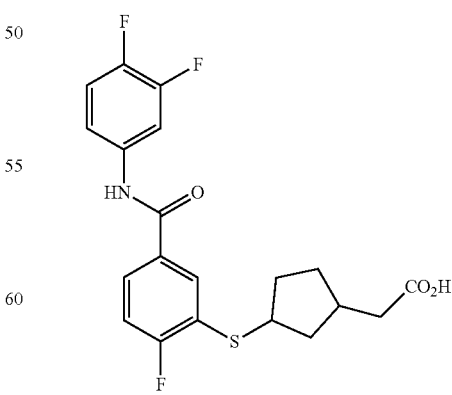

Prepared in an analogous manner to Example 102 but using 3,4-difluoroaniline in step 4. LC-MS: 410 (M+H)$^+$.

113

Example 106: (cis/trans)-2-(4-((5-((3-Chloro-4-fluorophenyl)carbamoyl)-2-fluorophenyl)thio)cyclohexyl)acetic Acid

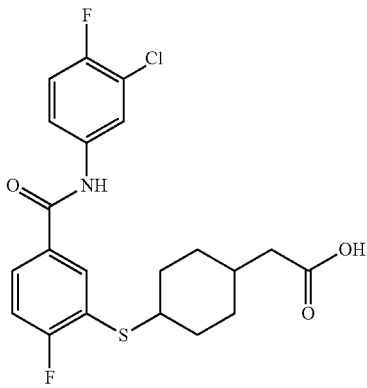 [SMILES: O=C(O)CC1CCC(Sc2cc(C(=O)Nc3ccc(F)c(Cl)c3)ccc2F)CC1]

Step 1;

To a solution of methyl 2-(4-hydroxycyclohexyl)acetate (1.00 g, 5.81 mmol) in DCM (20 mL) at 0° C. was added TEA (1.21 mL, 8.72 mmol), dimethylaminopyridine (0.035 g, 0.29 mmol), and 4-methylbenzene-1-sulfonyl chloride (1.22 g, 6.39 mmol). The resulting mixture was allowed to slowly warm to RT and stirred for 48 h. The reaction was evaporated then diluted with EtOAc and a 20% aq. solution of citric acid monohydrate added. The organics were separated, washed with water and concentrated in vacuo. The resulting crude material was purified on silica gel eluting with a solvent gradient of 0% to 50% EtOAc in hexanes to afford pure methyl 2-(4-(tosyloxy)cyclohexyl)acetate.

Step 2;

4-Fluoro-3-mercaptobenzoic acid (0.40 g, 2.32 mmol, intermediate W) and DMF (23 mL) were stirred at 0° C. while purging with subsurface nitrogen. To the resulting cold solution was added $Cs_2CO_3$ (1.51 g, 8.72 mmol) and methyl 2-(4-hydroxycyclohexyl)acetate (0.83 g, 2.55 mmol). The ice bath was removed and the reaction was stirred at 60° C. for 16 h. The reaction was diluted with EtOAc and a 20% aq. solution of citric acid monohydrate. The organics were separated, washed with 10% aq. solution of citric acid monohydrate, twice with water, concentrated in vacuo, and co-evaporated with heptanes. The resulting crude material was purified on silica gel eluting with a solvent gradient of 10% to 70% acetone in hexanes to afford pure 4-fluoro-3-((4-(2-methoxy-2-oxoethyl)cyclohexyl)thio)benzoic acid.

Step 3;

To a stirring solution of 4-fluoro-3-((4-(2-methoxy-2-oxoethyl)cyclohexyl)thio)benzoic acid (0.19 g, 0.58 mmol) in anhydrous DMF (6 mL) was added HATU (0.27 g, 0.70 mmol), 3-chloro-4-fluoroaniline (0.093 g, 0.64 mmol), DIPEA (0.31 mL, 1.74 mmol) and a catalytic amount of DMAP. The resulting mixture was stirred at rt for 16 h. The reaction was diluted with EtOAc and 0.5 M HCl. The organics were then washed once more with 0.5 M HCl, twice with water, concentrated in vacuo and co-evaporated with EtOAc. The resulting crude material was purified on silica gel eluting with a solvent gradient of 0% to 40% EtOAc in hexanes to afford methyl 2-(4-((5-((3-chloro-4-fluorophenyl)carbamoyl)-2-fluorophenyl)thio)cyclohexyl)acetate.

114

Step 4;

Methyl 2-(4-((5-((3-chloro-4-fluorophenyl)carbamoyl)-2-fluorophenyl)thio)cyclohexyl)acetate (0.16 g, 0.35 mmol), THF (4 mL), MeOH (4 mL), 1 M LiOH (2.82 mL, 2.82 mmol) and water (1.2 mL) were stirred at RT for 16 h. The reaction was concentrated and diluted with EtOAc and a 20% aq. solution of citric acid monohydrate. The organics were separated, washed three times with water and concentrated in vacuo. The resulting solid afforded the title compound in pure form. LC-MS: 440 (M+H)⁺.

Example 107: (cis/trans)-2-(4-((5-((3,4,5-trifluorophenyl)carbamoyl)-2-fluorophenyl)thio)cyclohexyl)acetic Acid

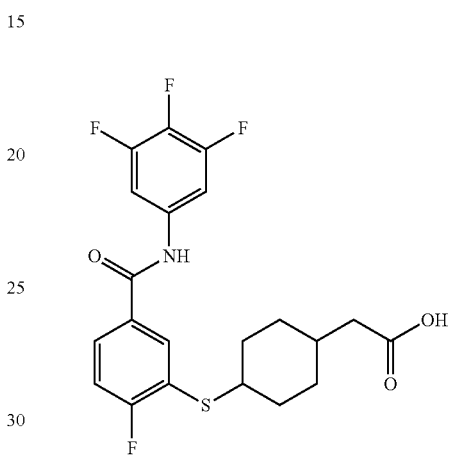

The title compound was prepared in an analogous manner to Example 106 using 3,4,5-trifluoroaniline in step 3. LC-MS: 442 (M+H)⁺.

Example 108: (cis/trans)-4-Fluoro-3-((4-(piperazine-1-carbonyl)cyclohexyl)thio)-N-(3,4,5-trifluorophenyl)benzamide

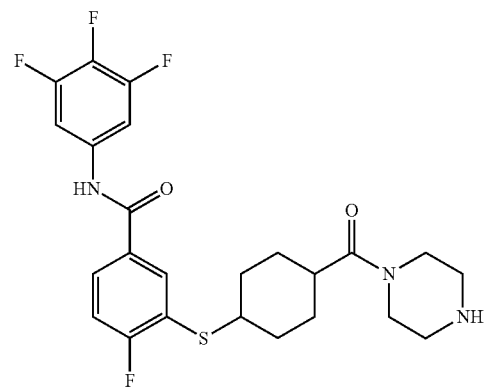 [SMILES: O=C(Nc1cc(F)c(F)c(F)c1)c1ccc(F)c(SC2CCC(C(=O)N3CCNCC3)CC2)c1]

Step 1:

To a DMF (5 mL) solution of Example 62 (35 mg, 0.082 mmol) was added diisopropylethylamine (0.022 mL, 0.123 mmol) and tert-butyl-1-piperazine-carboxylate (15 mg, 0.082 mmol). The mixture was stirred at RT for 1 hour before HATU (37 mg, 0.0984 mmol) was added. The resulting solution was stirred at RT for 13 h, quenched with water and extracted with EtOAc. The combined organics were washed further with water and brine, dried over Na₂SO₄, filtered and the filtrate concentrated in vacuo. Purification by preparative HPLC to afford tert-butyl 4-(4-((2-fluoro-5-((3,4,5-trifluorophenyl)carbamoyl)phenyl)thio)cyclohexanecarbonyl)piperazine-1-carboxylate (20 mg, 42% yield). LC-MS: 455 (M+H)⁺.

Step 2:
To a DCM (5 mL) solution of the amide (20 mg, 0.033) trifluoroacetic acid (1 mL) was added and stirred at RT for 2 h. The resulting solution was concentrated in vacuo and then diluted with EtOAc and washed with sat. NaHCO₃ solution. The combined organics were washed further with water and brine, dried over Na₂SO₄, filtered and the filtrate concentrated in vacuo to afford the title compound as a white solid (15 mg, 94% yield). LC-MS: 496 (M+H)⁺.

Example 109: (cis/trans)-4-(((5-((3-Chloro-4-fluorophenyl)carbamoyl)-2-fluorophenyl)thio)methyl)cyclohexanecarboxylic Acid

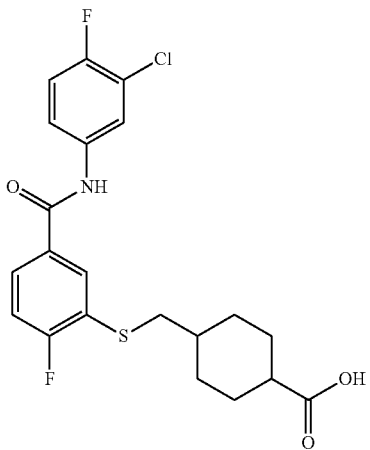 [SMILES: O=C(Nc1ccc(F)c(Cl)c1)c1ccc(F)c(SCC2CCC(C(=O)O)CC2)c1]

The title compound was prepared in an analogous manner to Example 106 using methyl 4-(hydroxymethyl)cyclohexanecarboxylate in step 1. LC-MS: 440 (M+H)⁺.

Example 110: (cis/trans)-4-(((5-((3,4,5-trifluorophenyl)carbamoyl)-2-fluorophenyl)thio)methyl)cyclohexanecarboxylic Acid

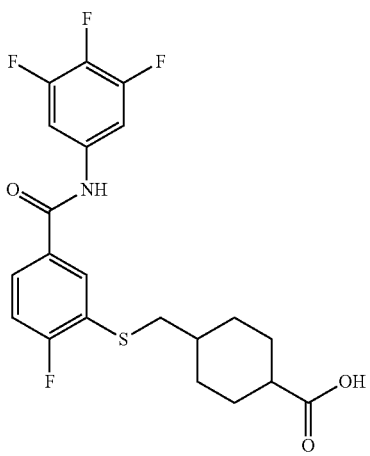 [SMILES: O=C(Nc1cc(F)c(F)c(F)c1)c1ccc(F)c(SCC2CCC(C(=O)O)CC2)c1]

The title compound was prepared in an analogous manner to Example 106 using methyl 4-(hydroxymethyl)cyclohexanecarboxylate in step 1 and 3,4,5-trifluoroaniline in step 3. LC-MS: 442 (M+H)⁺.

Example 111: (cis/trans)-4-((2-Fluoro-5-((3,4,5-trifluorophenyl)carbamoyl)phenyl)thio)-1-hydroxycyclohexanecarboxylic Acid

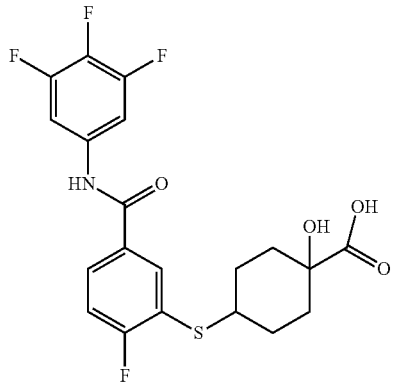 [SMILES: O=C(Nc1cc(F)c(F)c(F)c1)c1ccc(F)c(SC2CCC(O)(C(=O)O)CC2)c1]

Step 1:
To a DMSO solution (3.0 mL) of intermediate E (4-fluoro-3-mercapto-N-(3,4,5-trifluorophenyl)benzamide) (100.0 mg, 0.33 mmol) and methyl 1-hydroxy-4-(tosyloxy)cyclohexanecarboxylate (110 mg, 0.33 mmol) was added anhydrous cesium carbonate (325 mg, 1.0 mmol). The resulting solution was de-oxygenated via sub-surface purging with nitrogen for 5 min., and the reaction vessel was then sealed and heated at 60° C. overnight. After cooling to RT, the solution was acidified with 0.5 N HCl and extracted with EtOAc. The organic phase was washed with water and brine, dried over anhydrous sodium sulfate, filtered and concentrated in vacuo to afford the crude ester, methyl 4-((2-fluoro-5-((3,4,5-trifluorophenyl)carbamoyl)phenyl)thio)-1-hydroxycyclohexanecarboxylate. LC-MS: 456 (M–H)⁻.

Step 2:
To a THF/MeOH (3 mL/3 mL) solution of the crude residue in step 1, methyl 4-((2-fluoro-5-((3,4,5-trifluorophenyl)carbamoyl)phenyl)thio)-1-hydroxycyclohexanecarboxylate was added 2N LiOH (3 mL). The resulting mixture was stirred at RT for 13 h after which was diluted with EtOAc and washed sequentially with 1N HCl, water and brine and the volatiles removed in vacuo. The resulting mixture was subjected to purification by way of preparative HPLC to afford the title compound as an-off-white (25.0 mg, 17% overall yield over 2 steps). LC-MS: 442 (M–H)⁻.

Example 112A: cis-4-((2-Fluoro-5-((3,4,5-trifluorophenyl)carbamoyl)phenyl)thio)cyclohexanecarboxylic Acid

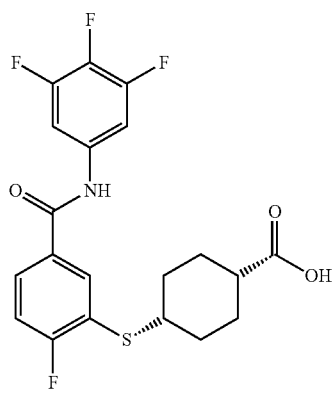

Prepared in an analogous manner to Example 111, but using trans-ethyl 4-((tosylsulfonyl)oxy)cyclohexanecarboxylate as the starting material.). LC-MS: 428 (M–H)⁻.

Example 112B: trans-4-((2-Fluoro-5-((3,4,5-trifluorophenyl)carbamoyl)phenyl)thio)cyclohexanecarboxylic Acid

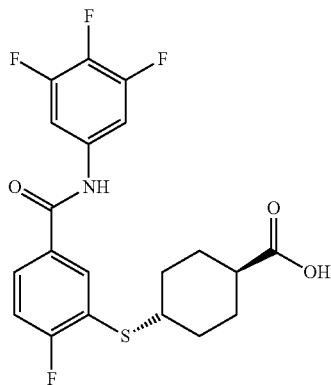

Prepared in an analogous manner to Example 111, but using cis-ethyl 4-((tosylsulfonyl)oxy)cyclohexanecarboxylate as the starting material). LC-MS: 428 (M–H)⁻.

Example 113: (±)-3-((2-Fluoro-5-((3,4,5-trifluorophenyl)carbamoyl)phenyl)thio)bicyclo[4.1.0]heptane-7-carboxylic Acid

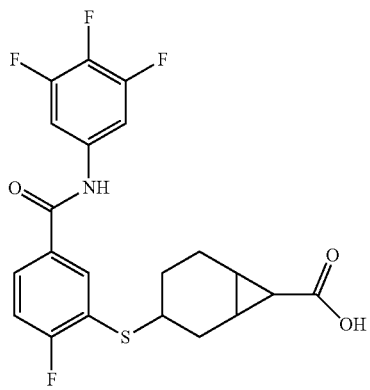 [SMILES: O=C(Nc1cc(F)c(F)c(F)c1)c1ccc(F)c(SC2CCC3C(C2)C3C(=O)O)c1]

Step 1;
To a solution of 9-BBN (0.5 M solution in THF, 40.00 mL, 20.00 mmol) at 0° C. was slowly added cyclohexa-1,4-diene (1.88 mL, 20.00 mmol). The resulting mixture was allowed to slowly warm to RT and stirred 16 h. To the stirring solution at RT, was added 3 M NaOH (6 mL) followed by dropwise addition of a 30% aq. solution of hydrogen peroxide. The reaction mixture was then refluxed for 1 hr then cooled to RT and diluted with Et₂O and brine. The organics were separated, washed with water and concentrated in vacuo. The resulting crude material was purified on silica gel eluting with a solvent gradient of 0% to 60% EtOAc in hexanes to afford cyclohex-3-enol.

Step 2;
Cyclohex-3-enol (0.90 g, 9.17 mmol) in DCM (20 mL) was stirred at 0° C., and TEA (1.53 mL, 11.00 mmol) and dimethylaminopyridine (1.06 g, 8.71 mmol) added. The resulting mixture was stirred cold for 5 minutes, then tert-butylchlorodimethylsilane (1.38 g, 9.17 mmol) was added. The solution was slowly allowed to warm to RT and stirred for 16 h. The reaction was evaporated then diluted with Et₂O and 1 M HCl. The organics were separated, washed once more with 1 M HCl, water, and dried over Na₂SO₄, filtered and concentrated in vacuo The resulting crude oil containing tert-butyl(cyclohex-3-en-1-yloxy)dimethylsilane was carried on to the next step without further purification.

Step 3;
To a stirring solution of tert-butyl(cyclohex-3-en-1-yloxy)dimethylsilane (1.00 g, 4.71 mmol) in DCM (40 mL) was added di-rhodium tetraacetate (0.042 g, 0.094 mmol) followed by very slow addition (over 6 h via syringe pump) of ethyl 2-diazoacetate (87% solution in DCM, 0.69 mL, 5.65 mmol). The resulting mixture was stirred at RT for 16 h. The reaction was filtered through paper and concentrated in vacuo. The resulting crude material was purified on silica gel eluting with a solvent gradient of 0% to 40% EtOAc in hexanes to afford ethyl 3-((tert-butyldimethylsilyl)oxy)bicyclo[4.1.0]heptane-7-carboxylate.

Step 4;
To a solution of ethyl 3-((tert-butyldimethylsilyl)oxy)bicyclo[4.1.0]heptane-7-carboxylate (0.80 g, 2.68 mmol) in THF (30 mL) was added TBAF (1.0 M solution in THF; 5.36 mL, 5.36 mmol). The solution was then stirred at RT for 48 h. The reaction was concentrated and diluted with EtOAc and water. The organics were washed once more with water, concentrated in vacuo, and co-evaporated with EtOAc. The resulting crude material containing ethyl 3-hydroxybicyclo[4.1.0]heptane-7-carboxylate was used without further purification.

Step 5;
The title compound was prepared in an analogous manner to Example 106 using ethyl 3-hydroxybicyclo[4.1.0]heptane-7-carboxylate in step 1. LC-MS: 440 (M+H)⁺.

Example 114: (cis/trans)-3-((4-(((Cyclopropylsulfonyl)carbamoyl)cyclohexyl)thio)-4-fluoro-N-(3,4,5-trifluorophenyl)benzamide

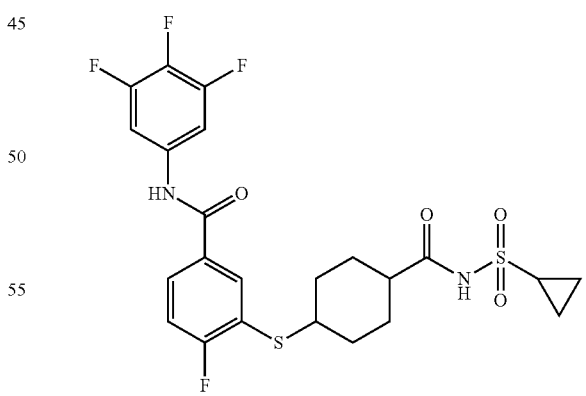

To a DCM (10 mL) solution of Example 62 (34 mg, 0.086 mmol), cyclopropyl sulfonamide (14 mg, 0.119 mmol), DMAP (15 mg, 0.119 mmol) and EDCI (23 mg, 0.119 mmol) were added and stirred at RT for 16 h. The reaction mixture was concentrated in vacuo and the residue purified by preparative HPLC to afford the title compound (25 mg, 45% yield). LC-MS: 531 (M+H)⁺.

Example 115: (cis/trans)-3-((4-(Ethylcarbamoyl)cyclohexyl)thio)-4-fluoro-N-(3,4,5-trifluorophenyl)benzamide

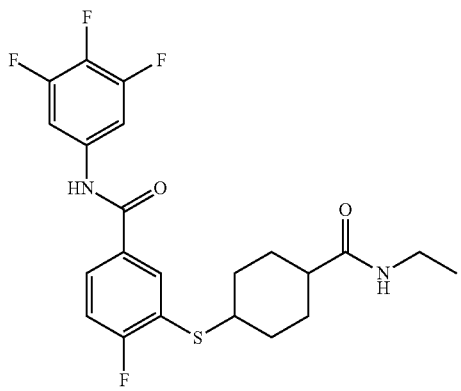 [SMILES: CCNC(=O)C1CCC(Sc2cc(C(=O)Nc3cc(F)c(F)c(F)c3)ccc2F)CC1]

Prepared in an analogous manner to Example 104 but using ethylamine. LC-MS: 455 (M+H)+.

Example 116: (cis/trans)-4-Fluoro-3-((4-(morpholine-4-carbonyl)cyclohexyl)thio)-N-(3,4,5-trifluorophenyl)benzamide

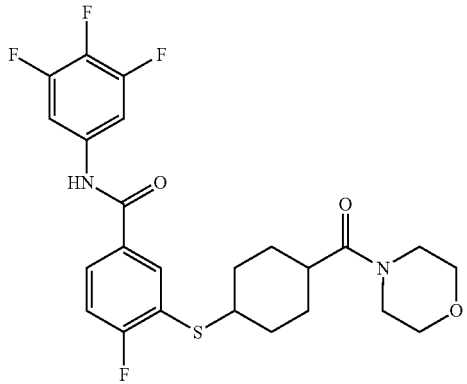 [SMILES: O=C(Nc1cc(F)c(F)c(F)c1)c1ccc(F)c(SC2CCC(C(=O)N3CCOCC3)CC2)c1]

Prepared in an analogous manner to Example 104 but using morpholine. LC-MS: 497 (M+H)+.

Example 117: (cis/trans)-3-((4-(2,6-Diazaspiro[3.3]heptane-2-carbonyl)cyclohexyl)thio)-4-fluoro-N-(3,4,5-trifluorophenyl)benzamide

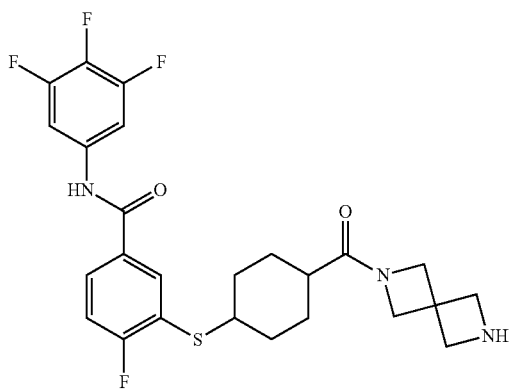 [SMILES: O=C(Nc1cc(F)c(F)c(F)c1)c1ccc(F)c(SC2CCC(C(=O)N3CC4(CNC4)C3)CC2)c1]

Prepared in an analogous manner to Example 10 but using instead tert-butyl 2,6-diazaspiro[3.3]heptane-2-carboxylate in step 1. LC-MS: 508 (M+H)+.

Example 118: (cis/trans)-1-Ethyl-4-((2-fluoro-5-((3,4,5-trifluorophenyl)carbamoyl)phenyl)thio)cyclohexanecarboxylic Acid

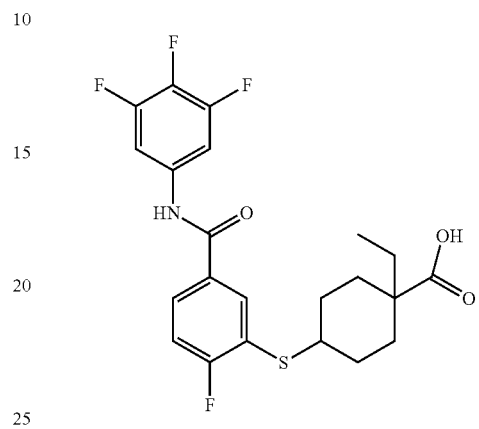

Step 1:
Prepared in an analogous manner to Example 111 (Step 1), but using ethyl 1-ethyl-4-(tosyloxy)cyclohexanecarboxylate to afford the intermediate ester, ethyl-(1-ethyl-4-((2-fluoro-5-((3,4,5-trifluorophenyl)carbamoyl)phenyl)thio)cyclohexanecarboxylate). LC-MS: 484 (M+H)+.

Step 2:
To a 1,4-dioxane/MeOH (0.5 mL/0.5 mL) solution of the crude residue in step 1, ethyl-(1-ethyl-4-((2-fluoro-5-((3,4,5-trifluorophenyl)carbamoyl)phenyl)thio)cyclohexanecarboxylate (36.0 mg, 0.074 mmol) was added 12.5N aqueous NaOH solution (3 mL, 37.5 mmol). The reaction solution was stirred at 50° C. for 16 h, cooled to RT, and acidified with 1 N HCl then extracted with EtOAc. The organic phases were washed with water and brine, dried over anhydrous sodium sulfate, filtered and concentrated in vacuo and purified by HPLC to afford the title compound as an off-white solid (10.1 mg, 30% Yield). LC-MS: 456 (M+H)+.

Example 119: (cis/trans)-4-((5-((3-Chloro-4-fluorophenyl)carbamoyl)-2-fluorophenyl)thio)-1-methylcyclohexanecarboxylic Acid

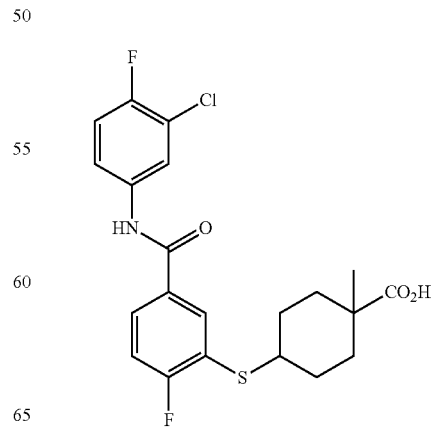

Step 1:
To a MeOH (40 mL) solution of methyl 1-methyl-4-oxocyclohexanecarboxylate (1.38 g, 8.11 mmol), cooled to 0° C. was added NaBH$_4$ (450 mg, 12.16 mmol). The resulting mixture was allowed to warm to RT for 13 h. The reaction mixture was quenched with 1N HCl and extracted with EtOAc twice. The combined organics were then washed further with brine, dried over Na$_2$SO$_4$, filtered and the filtrate concentrated in vacuo. No further purification was necessary to afford methyl 4-hydroxy-1-methylcyclohexanecarboxylate.

Step 2:
To a DCM (45 mL) solution of the alcohol (610 mg, 3.55 mmol) was added triethylamine (0.736 mL, 5.32 mmol). The solution was cooled to 0° C. before methanesulfonyl chloride (0.410 mL, 5.32 mmol) was added dropwise. The resulting mixture was allowed to warm to RT over 13 h. The reaction was diluted with DCM and washed with water, then dried over Na$_2$SO$_4$, filtered and the filtrate concentrated in vacuo. No further purification was necessary to afford methyl 1-methyl-4-((methylsulfonyl)oxy)cyclohexanecarboxylate.

Step 3:
To an acetone (80 mL) solution of the mesylate (812 mg, 3.24 mmol), sodium iodide (4.8 g, 32.4 mmol) was added and the resulting solution stirred at 80° C. in the dark for 16 h. The volatiles were then evaporated in vacuo and then partitioned with EtOAc and water. The combined organics were washed further with 10% aq. Na$_2$S$_2$O$_3$ and brine, then dried over Na$_2$SO$_4$, filtered and the filtrate concentrated in vacuo. No further purification was necessary to afford methyl 4-iodo-1-methylcyclohexanecarboxylate.

Step 4:
To a DMSO (15 mL) solution of 4-fluoro-3-mercaptobenzoic acid (55 mg, 0.319 mmol), methyl 4-iodo-1-methylcyclohexanecarboxylate (111 mg, 0.382 mmol) and cesium carbonate (156 mg, 0.479 mmol) were added. The resulting suspension was then sealed and heated at 60° C. for 13 h. After cooling to RT, the reaction mixture was diluted with ether and washed sequentially with 1N HCl, water and brine. The organic phase was then dried over Na$_2$SO$_4$, filtered and the filtrate concentrated in vacuo. Purification by way of column chromatography (SiO$_2$, 0-60% EtOAc/hexanes) afforded 4-fluoro-3-((4-(methoxycarbonyl)-4-methylcyclohexyl)thio)benzoic acid.

Step 5:
To a DMF (5 mL) solution of the benzoic acid (30 mg, 0.0920 mmol) was added diisopropylethylamine (0.020 mL, 0.138 mmol) and 3-chloro-4-fluoroaniline (13 mg, 0.0920 mmol). The reaction mixture was stirred at RT for 1 hour before HATU (42 mg, 0.110 mmol) was added. The resulting solution was stirred at RT overnight, quenched with water and extracted with EtOAc. The combined organics were washed further with water and brine, dried over Na$_2$SO$_4$, filtered and the filtrate concentrated in vacuo. Purification by way of column chromatography (SiO$_2$, 0-100% EtOAc/hexanes) afforded methyl 4-((5-((3-chloro-4-fluorophenyl)carbamoyl)-2-fluorophenyl)thio)-1-methylcyclohexanecarboxylate. (30 mg, 62% yield).

Step 6:
To a THF/MeOH (3 mL/3 mL) solution of the ester (30 mg, 0.066 mmol) was added 2N LiOH (2 mL). The resulting mixture was stirred at RT for 13 h after which was diluted with EtOAc and washed sequentially with 1N HCl, water and brine and the volatiles removed in vacuo. The resulting mixture was subjected to purification by preparative HPLC to afford the title compound (20 mg, 68% yield). LC-MS: 440 (M+H)$^+$.

Example 120: (±)-3-((2-Fluoro-5-((3,4,5-trifluorophenyl)carbamoyl)phenyl)thio)-1-methylcyclopentanecarboxylic Acid

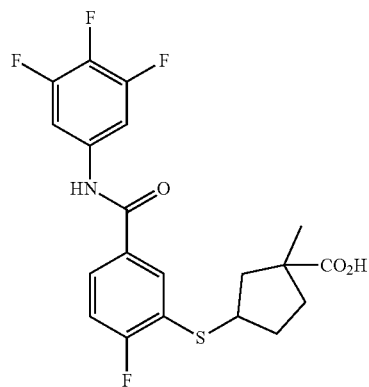 [SMILES: CC1(C(=O)O)CCC(Sc2cc(C(=O)Nc3cc(F)c(F)c(F)c3)ccc2F)C1]

Step 1:
To a nitrogen flushed vessel containing NaH (158 mg, 6.59 mmol), THF (6 mL) was added followed by the dropwise addition of methyl 3-hydroxycyclopentanecarboxylate (950 mg, 6.59 mmol). The resulting suspension was allowed to stir at 0° C. for 35 min. and then at RT for 45 min. In a separate round bottom flask flushed with nitrogen, diisopropylamine 1.1 mL, 7.91 mmol) in THF (10 mL) was cooled to −78° C. before n-BuLi (2.5 M in hexanes, 3.1 mL, 7.91 mmol) was added dropwise over 5 min. The resulting solution was allowed to stir at −78° C. for 30 min. and then at 0° C. for 30 min. The LDA thus generated was then added dropwise to the sodium alkoxide suspension at −78° C. Finally, methyl iodide (0.492 mL, 7.91 mmol) was added and stirred at 0° C. for 15 min and then at RT for 2.5 h. The crude mixture was quenched with sat. NH$_4$Cl solution and extracted in ether. The combined organics were then washed further with brine, dried over Na$_2$SO$_4$, filtered and the filtrate concentrated in vacuo. Purification by way of column chromatography (SiO$_2$, 0-100% EtOAc/hexanes) afforded methyl 3-hydroxy-1-methylcyclopentanecarboxylate (200 mg, 20% yield).

Step 2:
To a pyridine (10 mL) solution of the alcohol (102 mg, 0.645 mmol) was added p-toluenesulfonyl chloride (184 mg, 1.2 mmol) as a solution in pyridine (5 mL) dropwise. The resulting mixture was allowed to warm to RT over 13 h. The reaction was diluted with DCM and washed with sat. NaHCO$_3$, solution, water, and brine. The separated organics were then dried over Na$_2$SO$_4$, filtered and the filtrate concentrated in vacuo. No further purification was necessary to afford methyl 1-methyl-3-(tosyloxy)cyclopentanecarboxylate.

Step 3:
To a DMSO (5 mL) solution of Intermediate E (67 mg, 0.222 mmol), methyl 1-methyl-3-(tosyloxy)cyclopentanecarboxylate (100 mg, 0.333 mmol) and cesium carbonate (144 mg, 0.444 mmol) were added. The resulting suspension was then sealed and heated at 60° C. for 16 h. After cooling to RT, the reaction mixture was diluted with ether and washed sequentially with water and brine. The organic extract was then dried over Na$_2$SO$_4$, filtered and the filtrate concentrated in vacuo. Purification by preparative HPLC afforded methyl 3-((2-fluoro-5-((3,4,5-trifluorophenyl)carbamoyl)phenyl)thio)-1-methylcyclopentanecarboxylate (70 mg, 72% yield).

Step 5:

To a THF/MeOH (3 mL/3 mL) solution of the ester (70 mg, 0.158 mmol) was added 2N LiOH (2 mL). The resulting mixture was stirred at RT for 13 h after which was diluted with EtOAc and washed sequentially with 1N HCl, water and brine and the volatiles removed in vacuo. The resulting mixture was subjected to purification by preparative HPLC to afford the title compound (40 mg, 60% yield). LC-MS: 428 (M+H)$^+$.

Example 121A: (±)-(1S,3R)-3-((5-((3-Chloro-4-fluorophenyl)carbamoyl)-2-fluorophenyl)thio)cyclohexanecarboxylic Acid

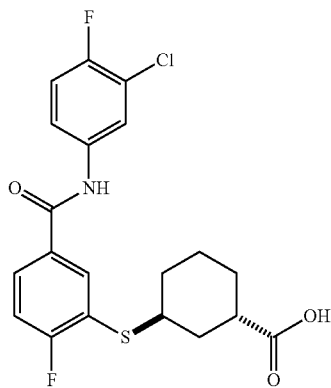

Step 1;

To a solution of 3-hydroxycyclohexanecarboxylic acid (1.25 g, 8.67 mmol) in MeOH (20 mL) at RT was added thionyl chloride (1.26 mL, 17.34 mmol). The resulting mixture was at 70° C. for 16 h. The reaction was cooled to RT, evaporated, and sequentially co-evaporated once with MeOH and twice with EtOAc to afford pure methyl 3-hydroxycyclohexanecarboxylate.

Step 2;

The title compound was prepared in an analogous manner to Example 106 using methyl 3-hydroxycyclohexanecarboxylate in step 1 and chromatographic separation of the diastereoisomers. LC-MS: 426 (M+H)$^+$.

Example 121B: (±)-(1R,3R)-3-((5-((3-Chloro-4-fluorophenyl)carbamoyl)-2-fluorophenyl)thio)cyclohexanecarboxylic Acid

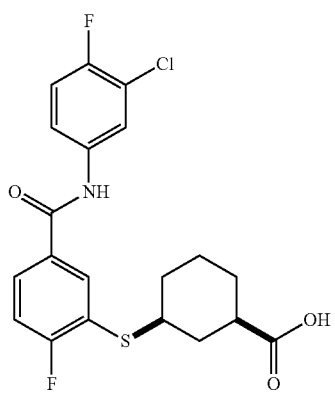

The title compound was prepared in an analogous manner to Example 106 using methyl 3-hydroxycyclohexanecarboxylate in step 1 and chromatographic separation of diastereoisomers at step 3. LC-MS: 426 (M+H)$^+$.

Example 122A: (±)-(1S,3R)-3-((2-Fluoro-5-((3,4,5-trifluorophenyl)carbamoyl)phenyl)thio)cyclohexanecarboxylic Acid

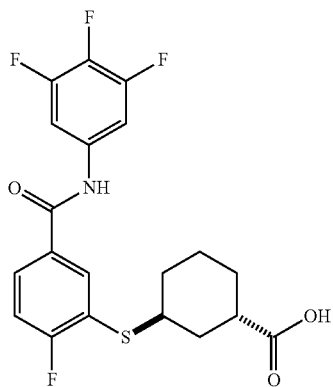

The title compound was prepared in an analogous manner to Example 106 using methyl 3-hydroxycyclohexanecarboxylate in step 1 and 3,4,5-trifluoroaniline in step 3. Chromatographic separation of diastereoisomers was achieved at step 3. LC-MS: 426 (M+H)$^+$.

Example 122B: (±)-(1R,3R)-3-((2-Fluoro-5-((3,4,5-trifluorophenyl)carbamoyl)phenyl)thio)cyclohexanecarboxylic Acid

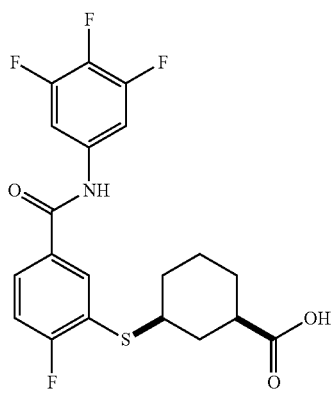

The title compound was prepared in an analogous manner to Example 106 using methyl 3-hydroxycyclohexanecarboxylate in step 1 and 3,4,5-trifluoroaniline in step 3. Chromatographic separation of the diastereoisomers was achieved at step 3. LC-MS: 426 (M+H)$^+$.

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tethrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention may exist as tautomers. All tautomers are included within the scope of the compounds presented herein.

Materials:

Unless otherwise noted, all starting materials and resins were obtained from commercial suppliers and used without purification.

Example: Inhibition of HBV Replication Dot-Blot Assay

Compounds active in the HBV assembly assay are tested for their activity and toxicity in cellular assay. In the first anti-viral assay, the ability of compounds to inhibit HBV replication in an HBV-producing hepatoma cell line using the dot-blot method is evaluated.

Briefly, confluent monolayers of HepG2-2.2.15 cells are incubated with complete medium containing various concentrations of a test compound. Three days later, the culture medium is replaced with fresh medium containing the appropriately diluted test compound. Six days following the initial administration of the test compound, the cell culture supernatant is collected, and cell lysis is performed. The samples are applied onto Nylos membranes and DNA is immobilized to the membrane by UV cross-linking. After pre-hybridization, the HBV probe is added and the hybridization is performed overnight. The membranes are exposed to the KODAK films; antiviral activity is calculated from the reduction in HBV DNA levels ($EC_{50}$). The $EC_{50}$ for antiviral activity is calculated from the dose response curves of active compounds. Assay performance over time is monitored by the use of the standard positive control compounds ETV, BAY 41-4109, and HAP-1.

Compound cytotoxicity ($TC_{50}$) is measured in this same HepG2-2.2.15 cell line using a CELLTITER BLUE-based cytotoxicity assay employed as recommended by manufacturer (Promega). To confirm and expand these results, a second antiviral assay is carried out on active compounds using the stable HBV cell line HepG2.2.15 and measuring anti-HBV potency by real-time PCR and cytotoxicity by CELLTITER BLUE. In this assay, 24 hours after cell seeding, HepG2-2.2.15 cells are incubated with complete medium containing various concentrations of a test compound with BAY 41-4109 and HAP-1 used as positive controls. After three days, the culture medium is replaced with fresh medium containing the appropriately diluted test compound. The cell culture is collected six days following the initial administration of the test compound, followed by HBV DNA extraction using QIAamp 96 DNA Blood Kit (Qiagen). The extracted HBV DNA is diluted and analyzed by Real-Time PCR. A standard curve is generated by plotting Ct value vs the amount of HBV plasmid standard. Cytotoxicity is determined similarly to the above described method by applying a dye uptake method (CELLTITER BLUE kit, Promega).

Selected compounds are tested for their activity and toxicity in cellular assay. In the first anti-viral assay, the ability of compounds to inhibit HBV replication in an HBV-producing hepatoma cell line using the dot-blot method is evaluated.

Confluent monolayers of HepG2-2.2.15 cells are incubated with complete medium containing various concentrations of a test compound. Three days later, the culture medium is replaced with fresh medium containing the appropriately diluted test compound. Six days following the initial administration of the test compound, the cell culture supernatant is collected, and cell lysis was performed. The samples are applied onto Nylos membranes and DNA is immobilized to the membrane by UV cross-linking. After pre-hybridization, the HBV probe is added and the hybridization is performed overnight. The membranes are exposed to the KODAK films; antiviral activity is calculated from the reduction in HBV DNA levels ($EC_{50}$). The $EC_{50}$ for antiviral activity is calculated from the dose response curves of active compounds. Assay performance over time is monitored by the use of the standard positive control compounds ETV, BAY 41-4109, and HAP-1. Results for selected compounds of the invention are illustrated in Table 2.

Cytotoxity ($CC_{50}$) is measured in this same HepG2-2.2.15 cell line using a CELLTITER BLUE-based cytotoxicity assay employed as recommended by the manufacturer (Promega).

Example: HBV Replication Inhibition Assay

HBV replication inhibition by the compounds of this invention could be determined in cells infected or transfected with HBV, or cells with stably integrated HBV, such as HepG2.2.15 cells (Sells et al. 1987). In this example, HepG2.2.15 cells are maintained in cell culture medium containing 10% fetal bovine serum (FBS), Geneticin, L-glutamine, penicillin and streptomycin. HepG2.2.15 cells could be seeded in 96-well plates at a density of 40,000 cells/well and be treated with serially diluted compounds at a final DMSO concentration of 0.5% either alone or in combination by adding drugs in a checker box format. Cells are incubated with compounds for three days, after which medium is removed and fresh medium containing compounds is added to cells and incubated for another three days. At day 6, supernatant is removed and treated with DNase at 37° C. for 60 minutes, followed by enzyme inactivation at 75° C. for 15 minutes. Encapsidated HBV DNA is released from the virions and covalently linked HBV polymerase by incubating in lysis buffer (Affymetrix QS0010) containing 2.5 µg proteinase K at 50° C. for 40 minutes. HBV DNA is denatured by addition of 0.2 M NaOH and detected using a branched DNA (bDNA) QuantiGene assay kit according to manufacturer recommendation (Affymetrix).

HBV DNA levels could also be quantified using qPCR, based on amplification of encapsidated HBV DNA extraction with QUICKEXTRACT Solution (Epicentre Biotechnologies) and amplification of HBV DNA using HBV specific PCR probes that can hybridize to HBV DNA and a fluorescently labeled probe for quantitation. In addition, cell viability of HepG2.2.15 cells incubated with test compounds alone or in combination is determined by using CELLTITER-GLO reagent according to the manufacturer protocol (Promega). The mean background signal from wells containing only culture medium is subtracted from all other samples, and percent inhibition at each compound concentration is calculated by normalizing to signals from HepG2.2.15 cells treated with 0.5% DMSO using equation E1.

$$\% \text{ inhibition} = (DMSOave - Xi)/DMSOave \times 100\% \quad \text{E1:}$$

wherein DMSOave is the mean signal calculated from the wells that are treated with DMSO control (0% inhibition control) and Xi is the signal measured from the individual wells. EC50 values, effective concentrations that achieved 50% inhibitory effect, are determined by non-linear fitting using Graphpad Prism software (San Diego, Calif.) and equation E2.

$$Y = Ymin + (Ymax - Ymin)/(1 + 10(\text{Log } EC50 - X) \times \text{Hill-Slope}) \quad \text{E2:}$$

wherein Y represents percent inhibition values and X represents the logarithm of compound concentrations.

Selected compounds of the invention were assayed in the HBV replication assay, as described above and a representative group of these active compounds is shown in Table 3.

TABLE 2

"Activity" represents activity in Dot-Blot assay

| Example # | Activity |
|---|---|
| 2 | + |
| 3 | + |
| 4 | + |
| 5 | + |
| 7 | + |
| 8 | + |
| 9 | + |
| 10 | + |
| 12 | + |
| 13 | + |
| 14A | + |
| 14B | + |
| 15 | + |
| 17 | + |
| 18 | + |
| 19 | + |
| 20 | + |
| 21 | + |
| 22 | + |
| 23 | + |
| 24 | + |
| 25 | + |
| 26 | + |
| 27 | + |
| 32 | + |
| 33 | + |
| 34 | + |
| 35 | + |
| 36 | + |
| 37 | + |
| 46 | + |

TABLE 2-continued

"Activity" represents activity in Dot-Blot assay

| Example # | Activity |
|---|---|
| 47 | + |
| 48 | + |
| 51 | + |
| 52 | + |
| 58 | + |
| 59 | + |
| 60 | + |
| 61 | + |
| 62 | + |
| 63 | + |
| 64 | + |
| 65 | + |
| 69 | + |
| 70 | + |
| 72 | + |
| 75 | + |
| 77 | + |
| 80 | + |
| 81 | + |
| 84 | + |
| 87 | + |
| 89 | + |
| 93 | + |
| 95 | + |
| 98 | + |
| 99 | + |
| 100 | + |
| 101 | + |
| 102 | + |
| 103 | + |
| 104 | + |
| 105 | + |
| 106 | + |
| 107 | + |
| 108 | + |
| 109 | + |
| 110 | + |

('+' indicates $EC_{50} < 10$ μM)

TABLE 3

HBV Replication Inhibition

| Example # | Extra HBV DNA (μM) |
|---|---|
| 2 | 0.138 |
| 4 | 0.22 |
| 10 | 0.09 |
| 18 | 0.57 |
| 24 | 0.042 |
| 32 | 0.41 |
| 33 | 0.62 |
| 35 | 1.21 |
| 36 | 1.34 |
| 37 | 1.07 |
| 38 | 1.27 |
| 39A | 1.29 |
| 39B | 1.29 |
| 40 | 0.76 |
| 62 | 0.71 |
| 63 | 1.6 |
| 98 | 1.3 |
| 99 | 4 |
| 100 | 1.7 |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.
The invention claimed is:
1. A compound selected from the group consisting of:
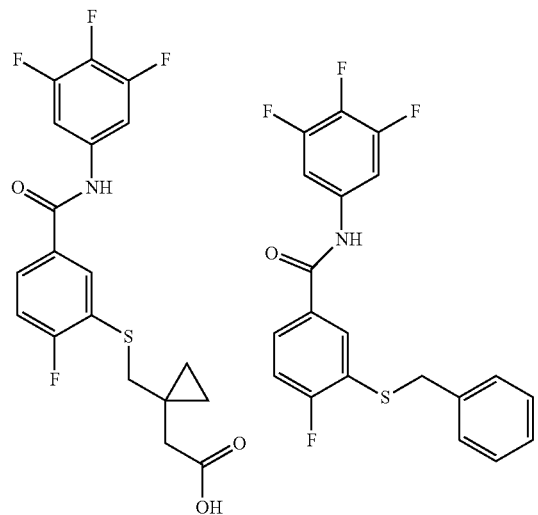
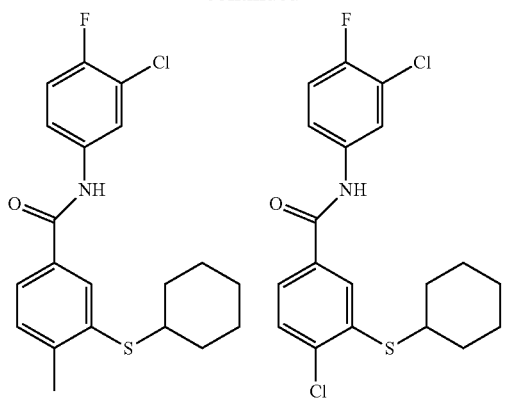
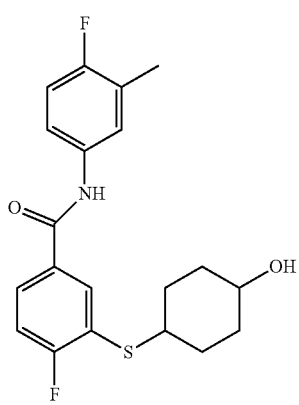

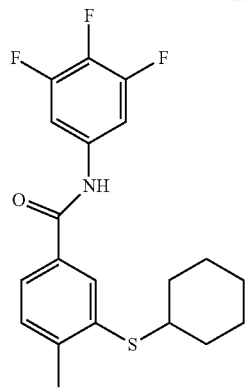
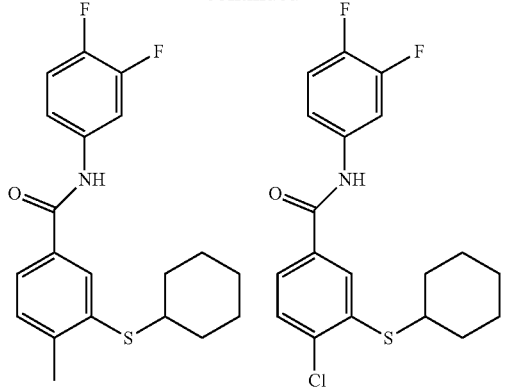
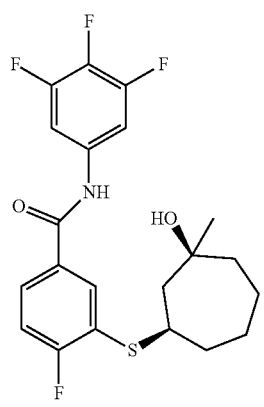
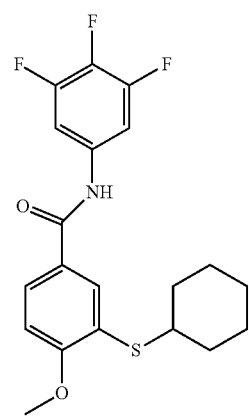
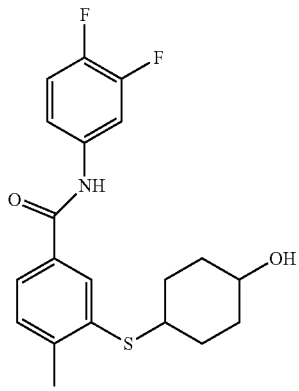
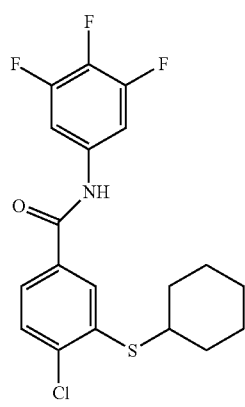
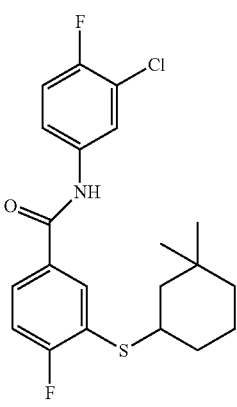
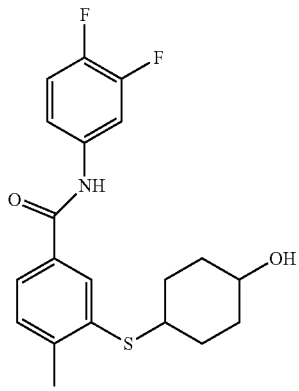
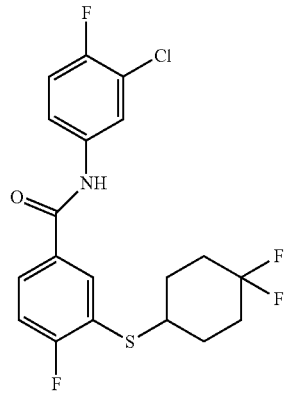
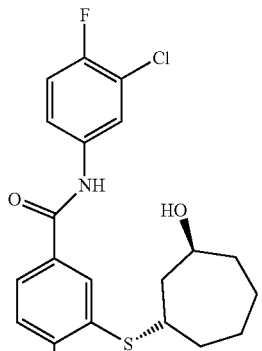
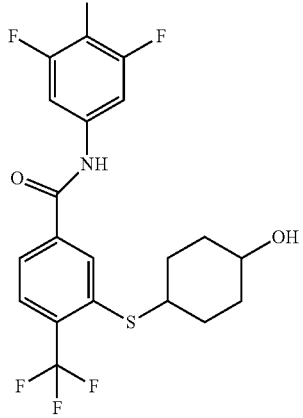

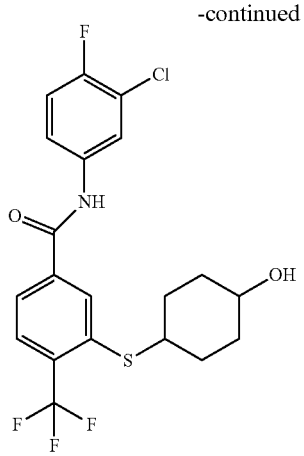
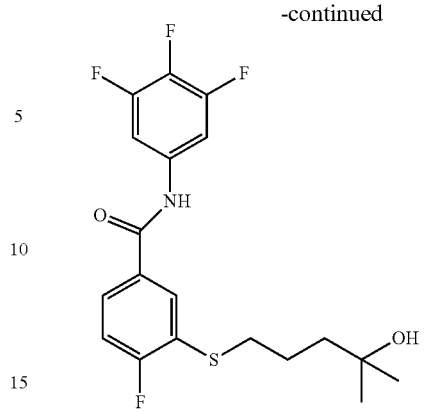
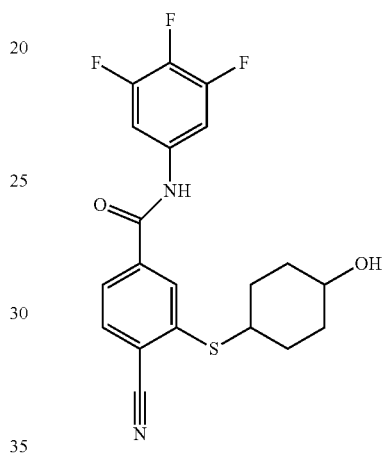
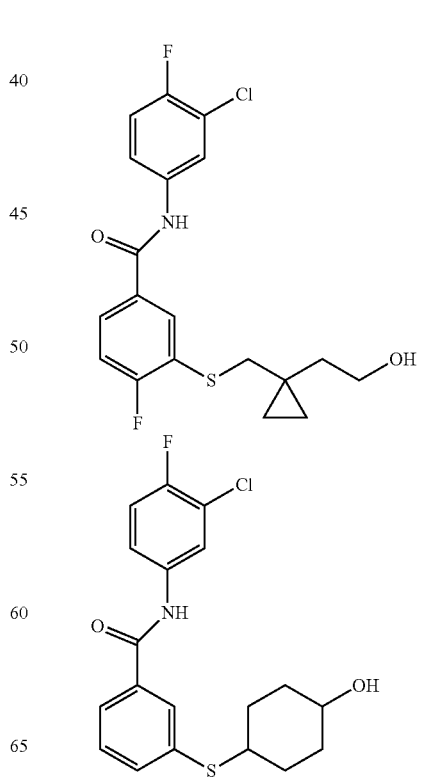

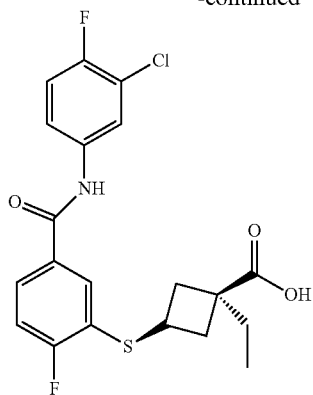
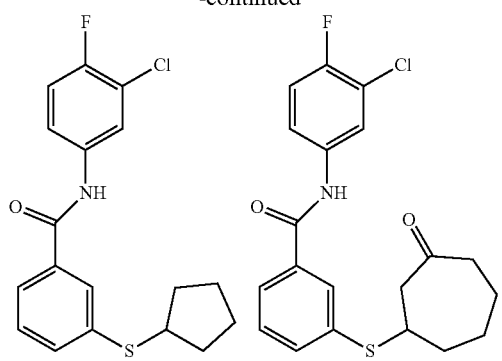
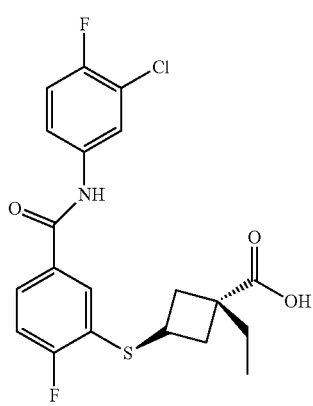
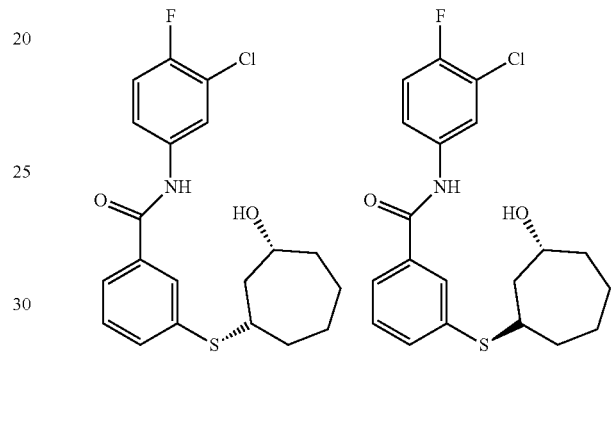
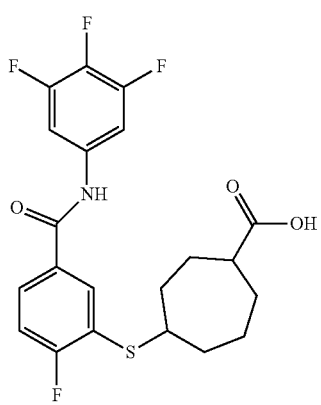
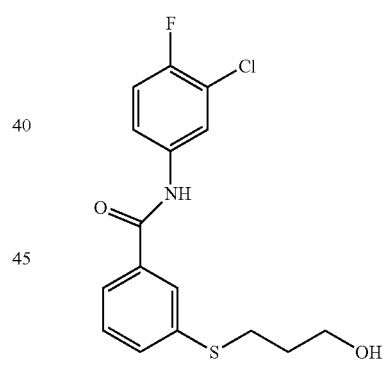
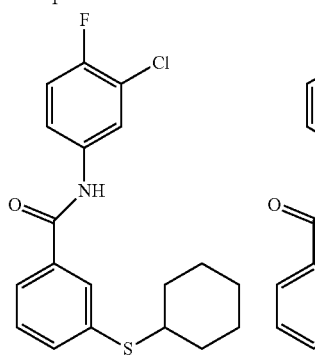
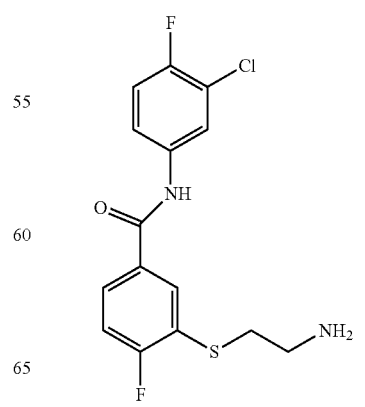

137
-continued
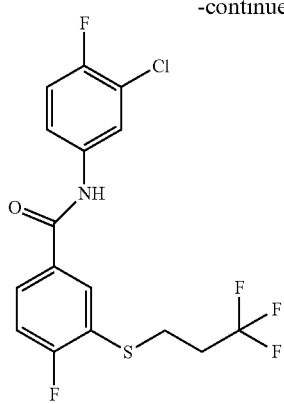
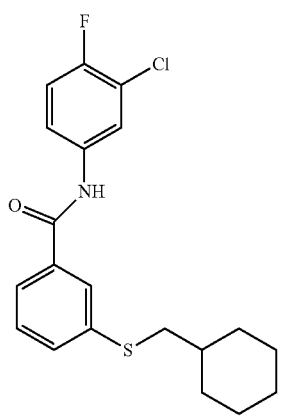
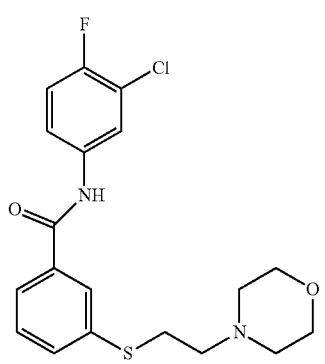
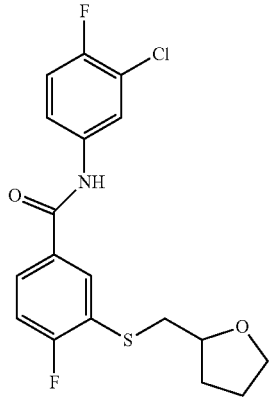
138
-continued
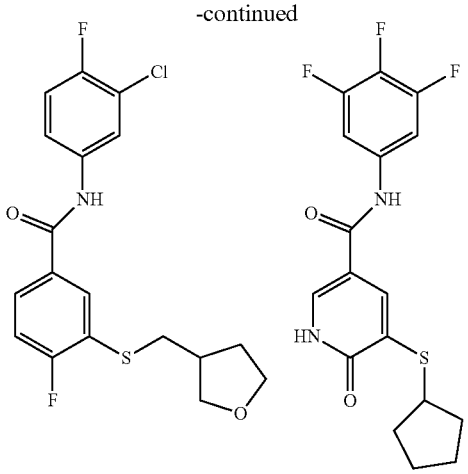
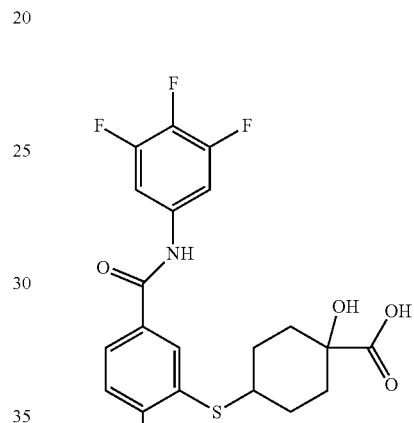
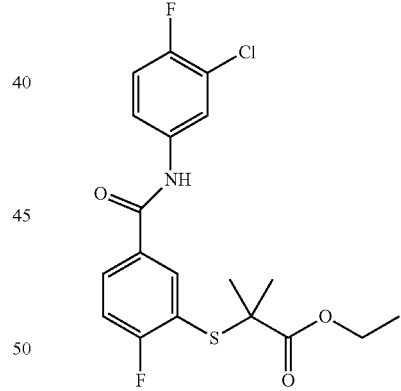
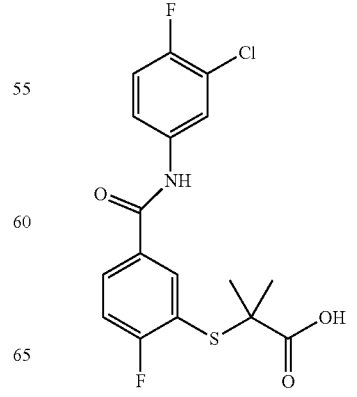

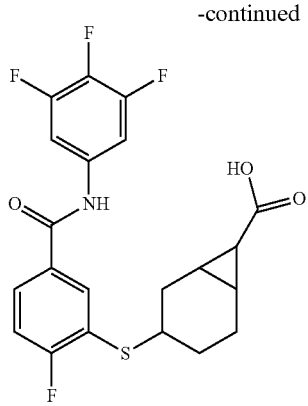
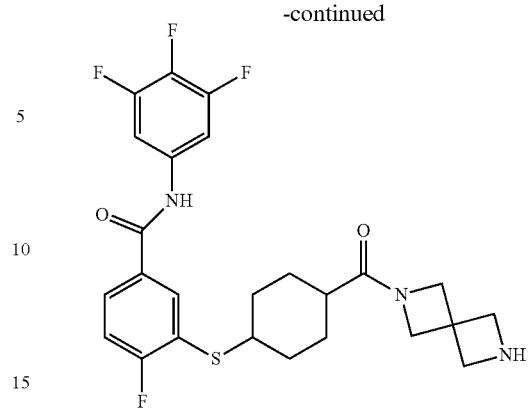
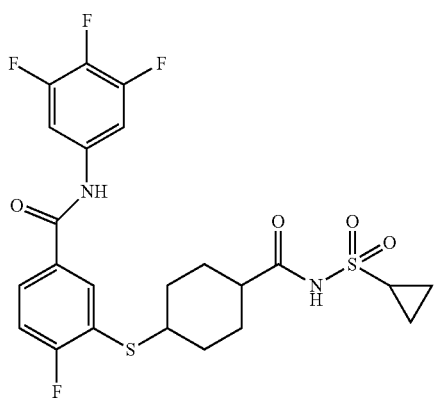
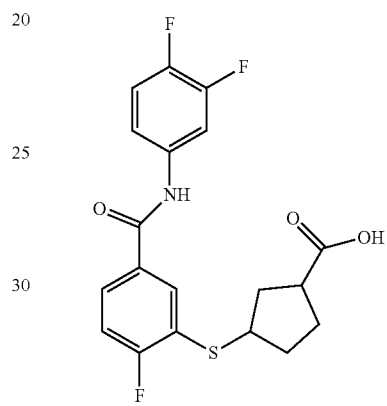
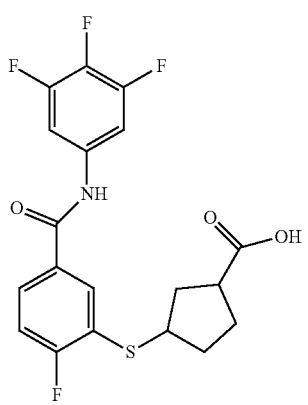
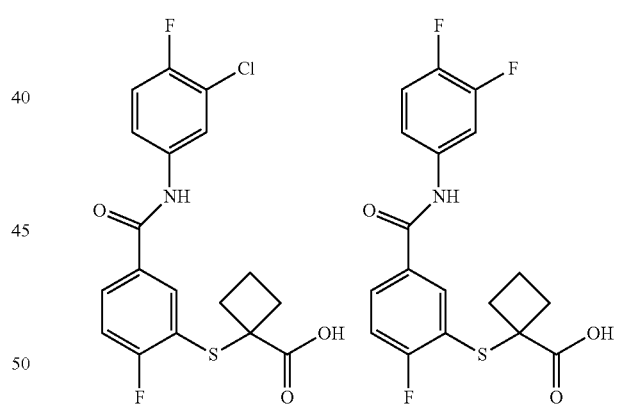
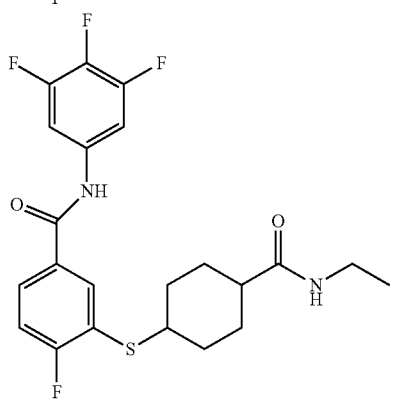
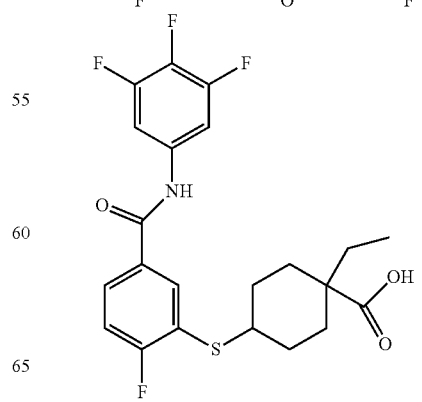

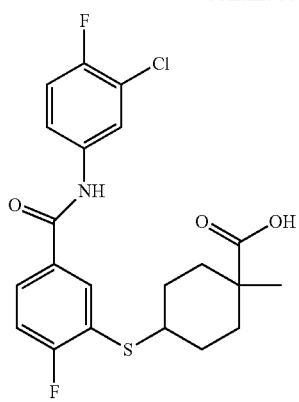

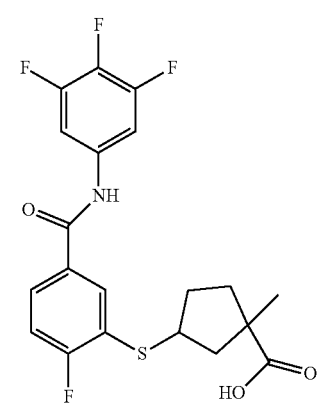

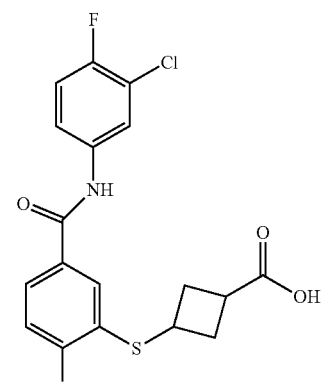

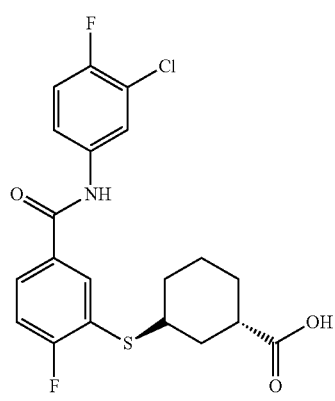

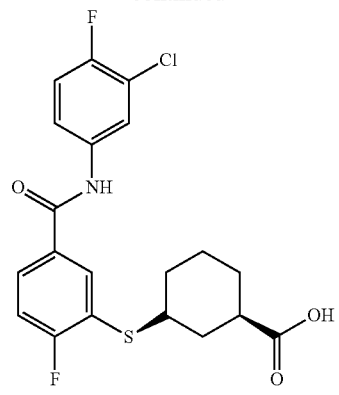

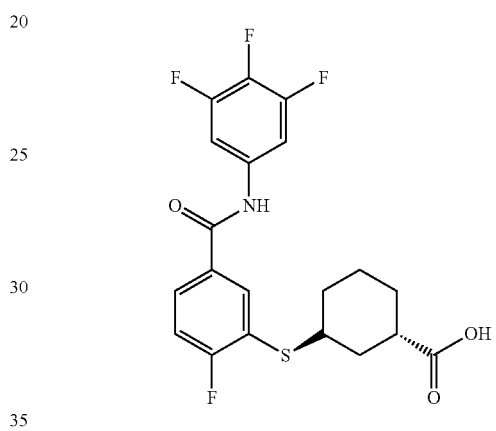

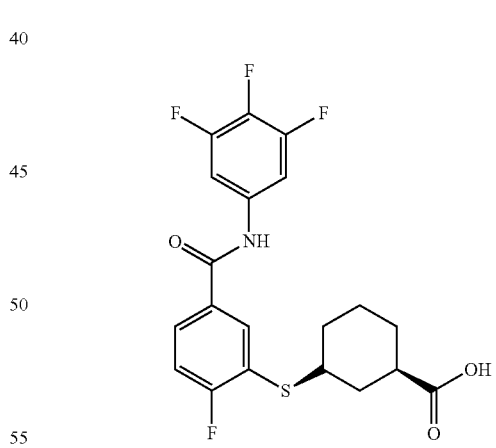

or a pharmaceutically acceptable salt thereof.

2. A composition comprising a compound according to claim 1, or a pharmaceutically acceptable salt thereof, further comprising at least one pharmaceutically acceptable carrier.

3. A method of treating an HBV infection in an individual in need thereof, comprising administering to the individual a therapeutically effective amount of a compound according to claim 1.

4. The method of claim 3, further comprising administering to the individual at least one additional therapeutic agent selected from the group consisting of an HBV vaccine, HBV polymerase inhibitor, interferon, pegylated interferon, viral entry inhibitor, viral maturation inhibitor, BAY 41-4109, reverse transcriptase inhibitor, a TLR-agonist, AT-61 ((E)-N-(1-chloro-3-oxo-1-phenyl-3-(piperidin-1-yl)prop-1-en-2-yl)benzamide), and AT-130 ((E)-N-(1-bromo-1-(2-methoxyphenyl)-3-oxo-3-(piperidin-1-yl)prop-1-en-2-yl)-4-nitrobenzamide), and a combination thereof.

5. The method of claim 4, wherein the pegylated interferon is pegylated interferon alpha (IFN-α), pegylated interferon lambda (IFN-λ), or pegylated interferon gamma (IFN-γ).

6. The method of claim 4, wherein the reverse transcriptase inhibitor is at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, cidofovir, Efavirenz, Nevirapine, Delavirdine, or Etravirine.

7. The method of claim 4, wherein the TLR-agonist is selected from the group consisting of SM360320 (9-benzyl-8-hydroxy-2-(2-methoxy-ethoxy)adenine) and AZD 8848 (methyl [3-({[3-(6-amino-2-butoxy-8-oxo-7,8-dihydro-9H-purin-9-yl)propyl][3-(4-morpholinyl) propyl]amino}methyl)phenyl]acetate).

8. The compound of claim 1, wherein the compound is:

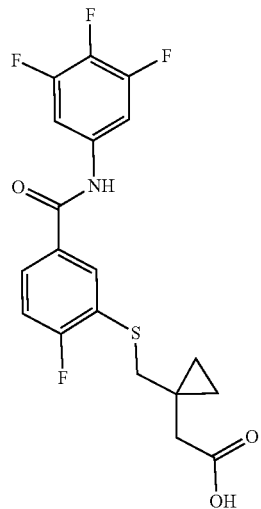 [SMILES: O=C(O)CC1(CSc2cc(C(=O)Nc3cc(F)c(F)c(F)c3)ccc2F)CC1]

or a pharmaceutically acceptable salt thereof.

* * * * *